United States Patent
Castelhano et al.

(10) Patent No.: US 7,504,407 B2
(45) Date of Patent: Mar. 17, 2009

(54) COMPOUNDS SPECIFIC TO ADENOSINE $A_1$ AND $A_3$ RECEPTORS AND USES THEREOF

(75) Inventors: Arlindo L. Castelhano, New City, NY (US); Bryan McKibben, Hopwell Junction, NY (US); Douglas S. Werner, Northport, NY (US); David Witter, Putnam Valley, NY (US)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

(21) Appl. No.: 10/497,451

(22) PCT Filed: Nov. 27, 2002

(86) PCT No.: PCT/US02/38055

§ 371 (c)(1),
(2), (4) Date: Dec. 13, 2004

(87) PCT Pub. No.: WO03/048120

PCT Pub. Date: Jun. 12, 2003

(65) Prior Publication Data

US 2005/0090513 A1   Apr. 28, 2005

Related U.S. Application Data

(60) Provisional application No. 60/337,274, filed on Nov. 30, 2001, provisional application No. 60/335,273, filed on Nov. 30, 2001.

(51) Int. Cl.
| | |
|---|---|
| C07D 487/04 | (2006.01) |
| C07D 519/00 | (2006.01) |
| A61K 31/519 | (2006.01) |
| A61P 11/06 | (2006.01) |
| A61P 27/06 | (2006.01) |
| A61P 27/02 | (2006.01) |
| A61P 11/08 | (2006.01) |

(52) U.S. Cl. .................... 514/265.1; 544/280
(58) Field of Classification Search ........... 544/280; 514/265.1
See application file for complete search history.

(56) References Cited

U.S. PATENT DOCUMENTS

| 3,037,980 A | 6/1962 | Hitchings et al. |
| 3,910,913 A | 10/1975 | Kim et al. |
| 5,208,240 A | 5/1993 | Peet et al. |
| 5,296,484 A | 3/1994 | Coghlan et al. |
| 5,409,930 A | 4/1995 | Spada et al. |
| 5,516,894 A | 5/1996 | Reppert |
| 5,580,870 A | 12/1996 | Barker et al. |
| 5,639,913 A | 6/1997 | Lidor et al. |
| 5,646,130 A | 7/1997 | Shi |
| 5,646,156 A | 7/1997 | Jacobson et al. |
| 5,681,941 A | 10/1997 | Cook et al. |
| 5,710,158 A | 1/1998 | Myers et al. |
| 5,714,493 A | 2/1998 | Myers et al. |
| 5,721,237 A | 2/1998 | Myers et al. |
| 5,747,498 A | 5/1998 | Schnur et al. |
| 5,780,450 A | 7/1998 | Shade |
| 5,780,481 A | 7/1998 | Jacobson et al. |
| 5,834,609 A | 11/1998 | Horne et al. |
| 5,877,180 A | 3/1999 | Linden et al. |
| 5,877,218 A | 3/1999 | Herzig et al. |
| 5,877,221 A | 3/1999 | Cohen et al. |
| 5,880,159 A | 3/1999 | Herzig et al. |
| 5,889,026 A | 3/1999 | Alanine |
| 5,914,349 A | 6/1999 | Cohen et al. |
| 5,935,964 A | 8/1999 | Baraldi et al. |
| 5,962,458 A | 10/1999 | Lohmann et al. |

(Continued)

FOREIGN PATENT DOCUMENTS

DE   3145287 A1   5/1993

(Continued)

OTHER PUBLICATIONS

Muller, C. E. et al., J. Med. Chem. 2002; 45(16); 3440-3450.*

(Continued)

Primary Examiner—Mark L Berch
(74) Attorney, Agent, or Firm—John P. White; Cooper & Dunham LLP

(57) ABSTRACT

This invention pertains to compounds having the structure:

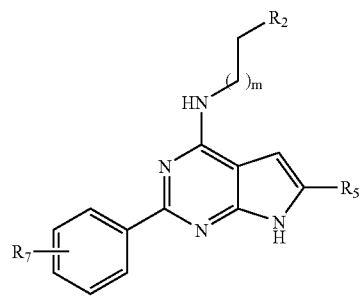

wherein
  m is 0, 1, 2, or 3;
  $R_2$ is a substituted or unsubstituted imidazole or pyrazole wherein the point of attachment of $R_2$ to the alkyl chain is not N;
  $R_5$ is a hydrogen atom or a substituted or unsubstituted alkyl, aryl, or alkylaryl moiety; and
  $R_7$ is a halogen atom, $C_1$-$C_4$ alkyl, OH, O-alkyl($C_1$-$C_4$), $NH_2$, or NH-alkyl($C_1$-$C_4$), which specifically inhibit the adenosine A1 and A3 receptors and the use of these compounds to treat a disease associated with A3 adenosine receptor in a subject, comprising administering to the subject a therapeutically effective amount of the compound.

12 Claims, No Drawings

U.S. PATENT DOCUMENTS

| | | | |
|---|---|---|---|
| 5,994,408 A | 11/1999 | Cohen et al. | |
| 6,103,899 A | 8/2000 | Horne et al. | |
| 6,117,878 A | 9/2000 | Linden | |
| 6,465,456 B2 | 10/2002 | Springer et al. | |
| 6,664,252 B2 * | 12/2003 | Castelhano et al. | 514/228.5 |
| 6,673,802 B2 * | 1/2004 | Castelhano et al. | 514/263.2 |
| 6,680,322 B2 * | 1/2004 | Castelhano et al. | 514/252.02 |
| 6,680,324 B2 * | 1/2004 | Castelhano et al. | 514/265.1 |
| 6,686,366 B1 * | 2/2004 | Castelhano et al. | 514/264.1 |
| 6,800,633 B2 * | 10/2004 | Castelhano et al. | 514/265.1 |
| 6,878,716 B1 * | 4/2005 | Castelhano et al. | 514/264.1 |
| 6,916,804 B2 | 7/2005 | Castelhano et al. | |
| 7,160,890 B2 | 1/2007 | Castelhano et al. | |
| 7,202,252 B2 | 4/2007 | Wilson et al. | |
| 7,429,574 B2 * | 9/2008 | Castelhano et al. | 514/81 |
| 2002/0058667 A1 | 5/2002 | Castelhano et al. | |
| 2002/0094974 A1 | 7/2002 | Castelhano et al. | |
| 2003/0139427 A1 | 7/2003 | Castelhano et al. | |
| 2003/0229067 A1 * | 12/2003 | Castelhano et al. | 514/210.21 |
| 2004/0082598 A1 * | 4/2004 | Castelhano et al. | 514/265.1 |
| 2004/0082599 A1 * | 4/2004 | Castelhano et al. | 514/265.1 |
| 2005/0043332 A1 * | 2/2005 | Castelhano et al. | 514/265.1 |
| 2005/0119271 A1 | 6/2005 | Castelhano et al. | |
| 2008/0070936 A1 | 3/2008 | Castelhano et al. | |

FOREIGN PATENT DOCUMENTS

| | | |
|---|---|---|
| EP | 322242 A2 | 6/1989 |
| EP | 0514540 A1 | 11/1992 |
| EP | 0682027 A1 | 11/1995 |
| EP | 729758 A2 | 4/1996 |
| EP | 0729758 A2 | 9/1996 |
| EP | 0773023 A1 | 5/1997 |
| EP | 1246623 B1 | 8/2003 |
| GB | 915303 | 1/1963 |
| IN | 157280 | 2/1986 |
| JP | 09291089 | 11/1997 |
| WO | 9320078 | 10/1993 |
| WO | 9413676 | 6/1994 |
| WO | 9417090 | 8/1994 |
| WO | 9419349 | 9/1994 |
| WO | 9424136 | 10/1994 |
| WO | 9511681 | 5/1995 |
| WO | 9518617 | 7/1995 |
| WO | 9519774 | 7/1995 |
| WO | 9519970 | 7/1995 |
| WO | 9520597 | 8/1995 |
| WO | 9619478 | 6/1996 |
| WO | 9702266 | 1/1997 |
| WO | 9705138 | 2/1997 |
| WO | 9733879 | 9/1997 |
| WO | 9747601 | 12/1997 |
| WO | 9807726 | 2/1998 |
| WO | 9808382 | 3/1998 |
| WO | 9822465 | 5/1998 |
| WO | 9829397 | 7/1998 |
| WO | 9857651 | 12/1998 |
| WO | 9906053 | 2/1999 |
| WO | 9908460 | 2/1999 |
| WO | 9933815 | 7/1999 |
| WO | 9942093 | 8/1999 |
| WO | 9962518 | 12/1999 |
| WO | 9964407 | 12/1999 |
| WO | 0003741 | 1/2000 |
| WO | WO 0139777 | 6/2001 |
| WO | 02057267 | 7/2002 |
| WO | 03048120 | 6/2003 |
| WO | 03053361 | 7/2003 |
| WO | 03053366 | 7/2003 |

OTHER PUBLICATIONS

Ezeamuzie, British J. Pharm. 127: 188-194 (1999).*
Priego, E.-M. et al, J. Med. Chem. 2002; 45(16); 3337-3344.*
International Search Report for International Application No. PCT/US02/38055 dated Jun. 10, 2003 (Exhibit 4).
Baraldi P.G. (2003) "Recent developments in the field of A2A and A3 adenosine receptor antagonists" Eur. J. Med. Chem. 38(4) 367.
Borman, S. (2001) "A3 Receptors" C&EN, 79(7), 37.
Fishman P (2003) "Pharmacology and therapeutic applications of A3 receptor subtype" Curr. Top. Med. Chem. 3(4) 463-9.
Mitchell, C.H. (1999) "A3 adenosine receptors regulate C1-channels of nonpigmented ciliary epithelial cells" Am. J. Physiol. 276, C659-C666.
Muller C.E. (2001) "A3 Adenosine Receptor Antagonists" Mini Reviews in Med. Chem. 1(4) 339.
Nyce J.W. (1997) "DNA antisense therapy for asthma in an animal model" 385: 721. Walker (1997) Am. J. Respir. Cell Mol. Biol. 161: 531.
Abbracchio M., et al., (1997) "Modulation of Apoptosis by Nervous System: a Possible Role for the $A_3$ Receptor", Ann. NY. Acad. Sci., 825: 11-22.
Abbracchio M., et al., (1999) "Brain Adenosine Receptors as Targets for Therapeutic Intervention in Neurodegenerative Diseases", Ann. NY. Acad. Sci, 890: 79-92.
Aoyama S. et al. (2000) "Rescue of Locomotor Impairment in Dopamine D2 Receptor-Deficient Mice by an Adenosine A2a Receptor Antagonist" J. Neuroscience 20(15):5848-5852.
Avila, M.Y. (2001) "A1-A2a and A3-Subtype Adenosine receptors Modulate Intraocular Pressure in the Mouse" J. of Pharmacol. 241-245.
Banker, G.S. et al., Modern Pharmaceutics, $3^{rd}$ ed., Marcel Dekker, New York, 1996, p. 596.
Baraldi, P.G. et al. (1996) "Pyrazolo [4,3-e]-1,2,4 triazolo [1,5-c]pyrimidine Derivatives: Potent and Selective A2a Adenosine Antagonists" J. Med. Chem. 39:1164-1171.
Baraldi P., et al., (2000) "New potent and selective human adenosine $A_3$ receptor antagonists", Tips, 21: 456-459.
Baraldi et al. "Pyrazolo-triazolo-pyrimidine derivatives as adenosine receptor antagonists: a possible template for adenosine receptor subtypes", Curr. Pharm. Design 8: 2299-2332, 2002.
Baraldi, P.G. et al., (1999) "A1 and A3 adenosine receptor agonists: an overview." Expert Opinion on Therapeutic Patents, 9(5):515-527.
Baraldi, P.G. et al., (2004) "Allosteric modulators for the A1 adenosine receptor." Expert Opinion on Therapeutic Patents, 14(1):71-79.
Barrett, R.J. (1996) "Realizing the Potential of Adenosine-Receptor-Based Therapeutics" Proc. West. Pharmacol. Soc. 39: 61-66.
Barrett, R.J. et al., "N-0861 selectively antagonizes adenosine A1 receptors in vivo" European J. Pharmacology (1992) 216: 9-16.
Blazynski C., (1990) "Discrete Distributions of Adenosine Receptors in Mammalian Retina", Journal of Neurochemistry, 53: 648-655.
Braas K.M., et al., (1987) "Endogenous adenosine and adenosine receptors localized to ganglion cells of the retina", Proceedings of the National Academy of Science, 84: 3906-3910.
Bradford M. M., (1976) "A Rapid and Sensitive Method for the Quantitation of Microgram Quantities of Protein Utilizing the Principle of Protein-Dye Binding", Anal. Biochem., 72: 248.
Brand A., et al., (2001) "Adenosine A1 and A3 receptors mediate inhibition of synaptic transmission in rat cortical neurons", Neuropharmacology, 40: 85-95.
Bremer et al. (2002) "Therapy of Crohn's Disease in Childhood", Expert Opin. Pharmacother. 3(7): 809-825.
Broach, J. R., et al., (1983) "Vectors for high level, inducible expression of cloned genes in yeast", Inouye (ed)., Experimental Manipulation of Gene Expression. Academic Press, New York, 83-117.
Bundy, G.L. et al. (1995) "Synthesis of Novel 2,4-Diaminopyrrolo-[2,3-d]pyrimidines with Antioxidant, Neuroprotective, and Antiasthma Activity" J. Med. Chem. 38:4161-4163.

Campbell, R.M. et al., "Selective $A_1$-Adenosine Receptor Antagonists Identified Using Yeast *Saccharomyces Cerevisiae* Functional Assays" *Bioorg. & Med. Chem. Lett.* (1999) 9(16): 2413-2418.

Casavola V., et al., (1998) "Adenosine A3 receptor activation increases cystolic calcium concentration via calcium influx in A6 cells", *Drug Development Research*, 43 (1): 62.

Cheng, Y. and Prusoff, W. H. (1973) "Relationship Between The Inhibition Constant ($K_i$) And The Concentration Of Inhibitor Which Causes 50 Per Cent Inhibition ($I_{50}$) Of An Enzymatic Reaction", *Biochem. Pharmacol.*, 22: 3099-3109.

Christianson, T. W. et al., (1992) "Multifunctional yeast high-copy-number shuttle vectors", *Gene*, 110: 119-122.

Christofi, F.L. et al. (2001), "Differential Gene Expression of Adenosine A1, A2a, A2b, and A3 Receptors in the Human Enteric Nervous System", J. Comp. Neurol. 439(1): 46-64.

Coney, A.M. et al. (1998) "Role of Adenosine and its Receptors in the Vasodilation Induced in the Cerebral Cortex of the Rat by Systemic Hypoxia" *J. Physiol.* 509:507-518.

Cooper. J.A. (1995) "Adenosine Receptor-induced Cyclic AMP Generation and Inhibtion of 5-hydroxytryptamine release in Human Platelets" *Br. J. Clin. Pharmacol.* 40:43-50.

Corset, V. et al. (2000), "Netrin-1-mediated axon outgrowth and cAMP production requires interaction with adenosine A2b receptor", Nature, 407 (6805): 747-750.

Faivre, K. et al. (2001) "Suppression of Cellular Invasion by Activated G-Protein Subunits $G\alpha o$, $G\alpha i1$, and $G\alpha i3$ and Sequestration of $G\beta\gamma$", Mol. Pharmacol. 60: 363-372.

Feoktistov, I. and Biaggioni, I., (1997) "Adenosine A2B Receptors", Pharmacol. Rev. 49(4): 381-402.

Feoktistov, I. et al., (2002) "Differential Expression of Adenosine Receptors in Human Endothelial Cells", Circulation Research 90: 531-538.

Feoktistove, I. et al., (1998) "Adenosine A2B receptors: a novel therapeutic target in asthma?", TiPS 19: 148-153.

Fozard J., et al., (1996) "Mast cell degranulation following adenosine A3 receptor activation in rats", European Journal of Pharmacology, 298: 293-297.

Franco M., et al., (1999) "Adenosine Regulates Renal Nitric Oxide Production in Hypothyroid Rats", Journal of the American Society of Nephrology, 1681-1688.

Gao, Z. et al., "A2B Adenosine and P2Y2 Receptors Stimulate Mitogen-activated Protein Kinase in Human Embryonic Kidney-293 Cells" J. Bio. Chem. (1999) 274(9): 5972-5980.

Gao, E. et al., "Adenosine A1 Receptor Antagonist Prolongs Survival in the Hypoxic Rat" *J. Cardiovascular Pharm.* (2001) 38: 384-394.

Ghiardi, G.J. et al. (1999) "The Purine Nucleoside Adenosine in Retinal Ischemia-Reperfusion Injury" *Vision Research* 39:2519-2535.

Grant, M.B. et al., (2001) "Proliferation, Migration, and ERK Activation in Human Retinal Endothelial Cells through A2B Adenosine Receptor Stimulation", Invest. Opthalmol. Vis. Sci. 42(9): 2068-2073.

Guerra L., et al., (1998) "Adenosine A3 receptor activation increases cytosolic calcium influx in A6 cells", *Nephrology Dialysis Transplantation*, 13 (6): A5.

Guo, Y. et al., (2001) "Targeted deletion of A3 adenosine receptor confers resistance to myocardial ischemic injury and does not prevent early preconditioning." *J Mol Cell Cardiol*, 33:825-830.

Hart, H. et al., Organic Chemistry, A Short Course, (Houghton Mifflin: 1995), p. 121.

Haynes, J. Jr. et al., (1999) "5-(N-ethylcarboxamido) adenosine desensitizes the A2b-adenosine receptor in lung circulation", Am. J. Physiol. 276(6): H1877-H1883.

Herndon, J.L. et al., (1992) Herndon, J.L. et al., "Ketanserin Analogs: Structure-Affinity Relationships for 5-HT2 and 5-HT1C Serotonin Receptor Binding", J. Med. Chem. 35(26): 4903-4910.

Iwamura, H. et al. (1996) "Quantitative Aspects of the Receptor Binding of Cytokinin Agonists and Antagonists" *J. Med. Chem.*, 26: 838-844.

Jacobson K.A., et al., (1997) "Pharmacological Characterization of Novel A3 Adenosine Receptor-selective Antagonists", *Neuropharmacology*, 36 (9): 1157-1165.

Jacobson K.A., et al., (1998) "Adenosine A3 receptors: novel ligands and paradoxical effects", *Tips*, 19:184-191.

Jorgensen, A. et al. (1985) "Synthesis of 7H-Pyrrolo[2,3-d]pyrimidin-4-amines" *Liebigs, Ann. Chem.*, pp. 142-148.

Kaiser, S.M. and R.J. Quinn (1999) "Adenosine receptors as potential therapeutic targets" Drug Discovery Today 4(12): 542-551.

Kanda, T. et al. (1998) "Adenosine A2a Receptors Modify Motor Function in MPTP-treated Common Marmosets" Neuroreport 9:2857-2860.

Kanda, T. et al. (2000) "Combined Use of the Adenosine A2a Antagonist KW-6002 with L-DOPA or with Selective D1 or D2 Dopamine Agonists Incrases Antiparkinsonian Activity but not Dyskensia in MPTP-Treated Monkeys" Experimental Neurology 162:321-327.

Kang, Y. et al., (1990) "Effects of Expression of Mammalian $G\alpha$ and Hybrid Mammalian-Yeast $G\alpha$ Proteins on the Yeast Pheromone Response Signal Transduction Pathway", Mol. Cell. Biol., 10: 2582-2590.

Kiichiro, K. et al. "Synthesis of pyrazinecarboxylic acid derivs.—(II) derivs. of 3-aminopyrazinecarboxylic acid" Chem. Abstracts 56:8713.

Kiichiro, K. et al. "Synthesis of pyrazinecarboxylic acid derivs.—(II) derivs. of 3-aminopyrazinecarboxylic acid" (1961) Yakugaku Zasshi 81: 1650-1653 (Abstract only).

Kiritsy, J.A. et al., (1978) "Synthesis and Quantitative Structure-Activity Relationships of Some Antibacterial 3-Formylrifamycin SV N-(4-Substituted phenyl) piperazinoacethydrazones" J. Med. Chem. 21(12): 1301-1307.

Klumpp, D.A. et al., (1999) "Synthesis of Aryl-Substituted Piperidines by Superacid Activation of Piperidones" J. Org. Chem. 64(18): 6702-6705.

Knutsen, L.J.S. et al. (2001) *Curr. Opin. Invest. Drugs* 2(5):668-673.

Kopf, S.R. et al. (1999) "Adenosine and Memory Storage: Effect of A1 and A2 Receptor Antagonists" *Psychopharmacology* 146:214-219.

Lee T., et al., (1999) "Protective effects of renal ischemic preconditioning and adenosine pretreatment: role of A1 and A3 receptors", $72^{nd}$ *Scientific Sessions of the American Heart Association*, Atlanta, GA, p. 197.

Lee T., et al., (2000) "Protective effects of renal ischemic preconditioning and adenosine pretreatment: role of A1 and A3 receptors", *Am. J. Physiol. Renal Physiol.*, 278: F380-F387.

Li, J.M. et al., (1998) "Adenosine A2a Receptors Incrase Arterial Endothelial Cell Nitric Oxide" *J. Surg. Res.* 80:357-364.

Linden, J. et al., (1998) "The Structure and Function of A1 and A2B Adenosine Receptors" Life Sciences 62(17-18): 1519-1524.

Marx, D. et al. (2001) "Therapy of Bronchial Asthma with Adenosine Receptor Agonists or Antagonists" *Drug News Perspect*. 14(2): 89-100.

Mautner, H.G., (1961) "Potential Deoxyribonucleic Acid Crosslonking Agents. 8,8'-Bispurines", *J. Org. Chem.* 26(6):1914-1917.

Meade et al., PubMed Abstract (Life Sci. 69(11):1225-40) Aug. 2001.

Mitchell, C.H. et al., "Adenosine A3 Receptor Activation Reduces Cell Volume and Activates $Cl^-$ Current in Human Ciliary Epithelial Cells", *FASEB J*, A134 (Abstract only).

Mirabet, M. et al., (1999) "Expression of A2B adenosine receptors in human lymphocytes: their role in T cell activation" J. Cell. Sci. 112(4): 491-502.

Montesinos, M.C. et al. (2002) "Adenosine Promotes Wounds Healings and Mediates Angiogenesis in Response to Tissue Injury Via Occupancy of A2a Receptors" *American Journal of Pathology* 160(6):2009-2018.

Muller, C. E. and Stein, B. (1996) "Adenosine Receptor Antagonist: Structure and Potential Therapeutic Applications", Current Pharmaceutical Design, 2: 501-530.

Muller, C. E. et al. (1990) "7-Deaza-2-phenyladenines: Structure-Activity Relationships of Potent A1 Selective Adenosine Receptor Antagonists" J. Med. Chem., 33: 2822-2828.

Muller, C. E. (1997) "A1-Adenosine Receptor Antagonists", Exp. Opin. Ther. Patents 7(5): 419-440.

Muller, C. E., et al., (1997) "Synthesis and Structure-Activity Relationships of 3,7-Dimethyl-1-propargylxanthine Derivatives, $A_{2A}$-Selective Adenosine Receptor Antagonists", *J. Med. Chem.*, 40: 4396-4405.

Muller, E. C. et al. (1996) "Chiral Pyrrolo[2,3-d]pyrimidine and Pyrimido[4,5,-b]indole Derivatives: Structure-Activity Relationships of Potent, Highly Steroselective $A_1$-Adenosine Receptor Antaogonist" *J. Med. Chem.*, 39: 2482-2491.

Nagarathnam, D. et al., (1998) "Design and Synthesis of Novel α1a Adrenoceptor-Selective Dihydropyridine Antagonists for the Treatment of Benign Prostatic Hyperplasia", J. Med. Chem. 41(26): 5320-5333.

Nishiyama, A. et al. (2001) "Interactions of Adenosine A1 and A2 a Receptors on Renal Microvascular Reactivity" *Am. J. Physiol. Renal Physiol.* 280:F406-F414.

Nishiyama, A. et al., "Adenosine A1 Receptor Antagonist KW-3902 Prevents Hypoxia-Induced Renal Vasoconstriction" J. Pharm. Exp. Ther. (1999), 291: 988-993.

Nyce J.W. (1997) "DNA Antisense thrapy for asthma in an animal model" 385: 721. Walker (1997) Am. J. Respir. Cell Mol. Biol. 161: 531.

Ohana G., et al., (2001) "Differential Effect of Adenosine on Tumor and Normal Cell Growth: Focus on the A3 Adenosine Receptor", *Journal of Cellular Physiology*, 186: 19-23.

Phillips, J.W. (1995) The Effects of Selective A1 and A2a Adenosine Receptor Antagonists on Cerebral Ischemic Injury in the Gerbil.

Pichler, H. et al. "Synthesis von 7-unsubstituierten *7H*-Pyrrolo [2,3-d] -pyrimidinen" *Liebigs Ann. Chemie.* 9:1485-1505.

Polosa (2002) "Adenosine-receptor subtypes: their relevance to adenosine-mediated responses in asthma and chronic obstructive pulmonary disease", Eur. Respir. Journal 20,488-496.

Ralevic, V. And Burnstock, G., (1998) "Receptors for Purines and Pyrimidines", Pharmacol. Rev. 50(3): 413-492.

Regnauld, K. et al., (2002) "G-protein αolf subunit promotes cellular invasion, survival, and neuroendocrine differentiation in digestive and urogenital epithelial cells", Oncogene 21(25): 4020-4031.

Regulation of Downstream Effectors By GPCRs, (1999) FASEB J., Abstracts 147.1-147.6.

Reshkin J., et al., (2000) "Activation of A3 Adenosine Receptor Induces Calcium Entry and Chloride Secretion in A6 Cells", *J. Membrane Biol.*, 178: 103-113.

Robinson, "Medical Therapy of Inflammatory Bowel Disease for the 21st Century", Eur J Surg. Suppl 582:90-98, 1998.

Sawynok J., et al., (1997) "Adenosine A3 receptor activation produces nociceptive behaviour and edema by release of histamine and 5-hydroxytryptamine", *European Journal of Pharmacology*, 333: 1-7.

Seela, F., and Lupke, U., (1977) *U. Chem. Ber.*, 110:1462-1469.

Shan, Daxian et al., *J. Pharmaceutical Sci.*, (1997) 86:765-767.

Shiozaki, S. et al. (1999) "Actions of Adenosine A2a Receptor Antagonist KW-6002 on Drug-induced Catalepsy and hypokinesia Caused by Reserpine of MPTP" *Psychopharmacology* 147:90-95.

Simone, Oncology: Introduction Cecil Textbook of Medicine, 20th Edition, vol. 1, pp. 1004-1010, 1996.

Singh et al., "Immune therapy in inflammatory bowel disease and models of colitis", British Journal of Surgery, 88: 1558-1569, 2001.

Strohmeier, G. R. et al., (1995) "The A2b Adenosine Receptor Mediates cAMP Responses to Adenosine Receptor Agonists in Human Intestinal Epithelia", J. Bio. Chem., 270: 2387-2394.

Svenningsson, P. et al. (1999) "Distribution, Biochemistry and Function of Striatal Adenosien A2a Receptors" *Prog. Neurobiol.* 59(4):355-396.

Szkotak, A.J. et al., "Regulation of $K^+$ current in human airway epithelial cells by exogenous and autocrine adenosine" *Am. J. Physiol. Cell Physiol.* (2001), 281: C1991-C2002.

Taomoto, M. ety al. (2000) "Localization of Adenosine A2 Receptor in Retinal Development and Oxygen-Induced Retinopathy" *Investigative Ophthalmology & Visual Science* 41(1):230-243.

Van Niel, M.B. et al., "Fluorianation of 3-(3-(Piperidin-1-yl)propyl)indoles and 3-(3-(Piperazin-1-yl)propyl)indoles Gives Selective Human 5-Htid Receptor Ligands with Improved Pharmokinetic Profiles" J. Med. Chem. (1999) 42(12): 2087-2104.

Varani, K. et al. (1998) "[$^3$H]-SCH 58261 Labelling of Functional A2a Adenosine Receptors in Human Neutrophil Membranes" *Br. J. Pharmacol.* 123:1723-1731.

Venugopalan, B. et al. (1998) "Synthesis of 6,7-Dimethoxypyrimido[4,5-b]-indoles as Potential Antihypertensive Agents" *J. Heterocyclic Chem.*, 25: 1663-1669.

Von Lubitz D., et al., (1999) "Stimulation of Adenosine A3 Receptors in Cerebral Ischemia", *Ann. NY. Acad. Sci.*, 890: 93-106.

Von Lubitz, D., et al., (1999) "Chronic administration of adenosine A3 receptor agonist and cerebral ischemia: neuronal and glial effects", European Journal of Pharmacology, 367: 157-163.

Welch, W.J. "Adenosine type 1 receptor antagonists in fluid retaining disorders" *Expert Opin. Investig. Drugs* (2002), 11(11): 1553-1562.

West, R.A. et al. (1961) "2-alkyl(aryl)-and 2,7-dimethyl-4-substituted aminopyrrolo[2,3-d]pyrimidines." *J. Org. Chem.*, 26:3809-3812.

Williams, E. F. et al., (1994) "Nucleoside transport sites in a cultured human retinal cell line established by SV-40 T antigen gene", Current Eye Research, 13: 109-118.

Wolff, Manfred E., *Burger's Medicinal Chemistry and Drug Discovery*, $5^{th}$ ed., *Volume I: Principles and Practice*, John Wiley & Sons, 1995, pp. 975-977.

Woods, C. L. and Blazynski, C. (1991) "Characterization of Adenosine A1-receptor Binding Sites in Bovine Retinal Membranes", Experimental Eye Research, 53: 325-331.

Yan, Luo et al. (2003) Expert Opinion on Emerging Drugs, vol. 8, No. 2 pp. 537-576.

Yao Y., et al., (1997) "Adenosine A3 Receptor Agonists Protect HL-60 and U-937 Cells from Apoptosis Induced by A3 Antagonists", *Biochemical And Biophysical Research Communications*, 232: 317-322.

Zhao Z., et al., (2000) "A role for the A3 Adenosine receptor in determining tissue levels of cAMP and blood pressure: studies in knock-out mice", *Biochimica et Biophysica Acta*, 1500: 280-290.

Zhao, Z. et al., "Bioactivation of 6,7-Dimethyl-2,4-di-1-pyrrolidinyl-7H-pyrrolo[2,3-d]pyrimidine (U-89843) to Reactive Intermediates that Bind Covalently to Macromolecules and Produce Genotoxicity" *Chem. Res. Toxicol.*, (1996) 9: 1230-1239.

International Search Report issued in PCT International Application No. PCT/US99/12135, filed Jun. 1, 1999.

PCT International Preliminary Examination Report issued in PCT International Application No. PCT/US00/32702, filed Jun. 1, 1999.

International Search Report issued in PCT International Application No. PCT/US2001/045280, filed Nov. 30, 2001.

International Search Report issued in PCT International Application No. PCT/US2002/38055, filed Nov. 27, 2002.

International Search Report issued in PCT International Application No. PCT/US2002/40890, filed Dec. 20, 2002.

International Search Report issued in PCT International Application No. PCT/US2002/41273, filed Dec. 20, 2002.

PCT International Preliminary Examination Report issued in PCT International Application No. PCT/US99/12135.

PCT International Preliminary Examination Report issued in PCT International Application No. PCT/US00/32702.

PCT International Preliminary Examination Report issued in PCT International Application No. PCT/US2001/045280, filed Nov. 30, 2001.

PCT International Preliminary Examination Report issued in PCT International Application No. PCT/US2002/38055, filed Nov. 27, 2002.

PCT International Preliminary Examination Report issued in PCT International Application No. PCT/US2002/40890, filed Dec. 20, 2002.

PCT International Preliminary Examination Report issued in PCT International Application No. PCT/US2002/41273, filed Dec. 20, 2002.

Supplemental European Search Report; for EP Application No. 02 80 5676; issued Feb. 7, 2006.

Partial European Search Report for EP Application No. 06 01 6543.8; completed Oct. 4, 2006.

Partial European Search Report; for EP Application No. 01 99 7029; completed Dec. 21, 2004.

PCT International Preliminary Examination Report issued in PCT International Application No. PCT/US200/38055, filed Nov. 27, 2002.

GenBank accession # S46950, May 8, 1993.

GenBank accession # S45235, May 8, 1993.

GenBank accession # S56143, May 4, 2000.

Hoeschst India Ltd., India (1987) "Pharmacologically active pyrimido [4,5-b]indoles and their salts." Database accession No. 106:84629 HCA XP002121648.

Tanaka, H. et al. (1998) "Preparation and formulation of fused pyrimidine compounds as CRF receptor antagonists." Database accession No. 129:109098 HCA XP002121647.

Cummings, J. et al., (2000) "Antagonism of the Cardiodepressant Effects of Adenosine during Acute Hypoxia" Academic Emergency Medicine, 7(8): 618-624.

DeNinno, M.P. (1998) in Annual Reports in Medicinal Chemistry, vol. 33, (Academic Press: San Diego, 1998), pp. 111-120.

Dhainaut, A. et al., (1996) "New Purines and Purine Analogs as Modulators of Multidrug Resistance" J. Med. Chem. 39: 4099-4108.

Dooley, M.J. et al., (1996) "Theoretical Structure-Activity Studies of Adenosine A1 Ligands: Requirements for Receptor Affinity" Bioorg. Med. Chem., 4(6): 923-934.

Dubey, R.K. et al., (2001) "A2B Receptors Mediate the Antimitogenic Effects of Adenosine in Cardiac Fibroblasts", Hypertension 37: 716-721.

Duzic, E. et al., (1992) "Factors Determining the Specificity of Signal Transduction by Guanine Nucleotide-binding Protein-coupled Receptors", *J. Biol. Chem.*, 267: 9844-9851.

Chen, Y.L. et al., (1997) "Synthesis and Oral Efficacy of a 4-(Butylethylamino)pyrrole[2,3-d]pyrimidine: A Centrally Active Corticotropin-Releasing Factor Receptor Antogonist", J. Med. Chem. 40:1749-1754.

U.S. Appl. No. 12/228,867.

U.S. Appl. No. 12/231,029.

* cited by examiner

COMPOUNDS SPECIFIC TO ADENOSINE A₁ AND A₃ RECEPTORS AND USES THEREOF

This application is a §371 national stage application of PCT International Application No. PCT/US02/38055, filed Nov. 27, 2002, claiming priority of U.S. Provisional Application No. 60/337,274, filed Nov. 30, 2001 and U.S. Provisional Application No. 60/335,273, filed Nov. 30, 2001, the contents of all of which are hereby incorporated by reference.

Throughout this application, various publications are referenced by author and date. Full citations for these publications may be found throughout the specification. The disclosures of these publications in their entireties are hereby incorporated by reference into this application in order to more fully describe the state of the art as known to those skilled therein as of the date of the invention described and claimed herein.

BACKGROUND OF THE INVENTION

Adenosine is an ubiquitous modulator of numerous physiological activities, particularly within the cardiovascular and nervous systems. The effects of adenosine appear to be mediated by specific cell surface receptor proteins. Adenosine modulates diverse physiological functions including induction of sedation, vasodilation, suppression of cardiac rate and contractility, inhibition of platelet aggregability, stimulation of gluconeogenesis and inhibition of lipolysis. In addition to its effects on adenylate cyclase, adenosine has been shown to open potassium channels, reduce flux through calcium channels, and inhibit or stimulate phosphoinositide turnover through receptor-mediated mechanisms (See for example, C. E. Muller and B. Stein "Adenosine Receptor Antagonists: Structures and Potential Therapeutic Applications," *Current Pharmaceutical Design*, 2:501 (1996) and C. E. Muller "A₁-Adenosine Receptor Antagonists," *Exp. Opin. Ther. Patents* 7(5):419 (1997)).

Adenosine receptors belong to the superfamily of purine receptors which are currently subdivided into $P_1$ (adenosine) and $P_2$ (ATP, ADP, and other nucleotides) receptors. Four receptor subtypes for the nucleoside adenosine have been cloned so far from various species including humans. Two receptor subtypes ($A_1$ and $A_{2a}$) exhibit affinity for adenosine in the nanomolar range while two other known subtypes $A_{2b}$ and $A_3$ are low-affinity receptors, with affinity for adenosine in the low-micromolar range. $A_1$ and $A_3$ adenosine receptor activation can lead to an inhibition of adenylate cyclase activity, while $A_{2a}$ and $A_{2b}$ activation causes a stimulation of adenylate cyclase.

A few $A_1$ antagonists have been developed for the treatment of cognitive disease, renal failure, and cardiac arrhythmias. It has been suggested that $A_{2a}$ antagonists may be beneficial for patients suffering from Morbus Parkinson (Parkinson's disease). Particularly in view of the potential for local delivery, adenosine receptor antagonists may be valuable for treatment of allergic inflammation and asthma. Available information (for example, Nyce & Metzger "DNA antisense Therapy for Asthma in an Animal Model" *Nature* (1997) 385: 721-5)indicates that in this pathophysiologic context, $A_1$ antagonists may block contraction of smooth muscle underlying respiratory epithelia, while $A_{2b}$ or $A_3$ receptor antagonists may block mast cell degranulation, mitigating the release of histamine and other inflammatory mediators. $A_{2b}$ receptors have been discovered throughout the gastrointestinal tract, especially in the colon and the intestinal epithelia. It has been suggested that $A_{2b}$ receptors mediate cAMP response (Strohmeier et al., *J. Bio. Chem.* (1995) 270: 2387-94).

Adenosine receptors have also been shown to exist on the retinas of various mammalian species including bovine, porcine, monkey, rat, guinea pig, mouse, rabbit and human (See, Blazynski et al., *Discrete Distributions of Adenosine Receptors in Mammalian Retina, Journal of Neurochemistry*, volume 54, pages 648-655 (1990); Woods et al., *Characterization of Adenosine $A_1$-Receptor Binding Sites in Bovine Retinal Membranes, Experimental Eye Research*, volume 53, pages 325-331 (1991); and Braas et al., *Endogenous adenosine and adenosine receptors localized to ganglion cells of the retina, Proceedings of the National Academy of Science*, volume 84, pages 3906-3910 (1987)). Recently, Williams reported the observation of adenosine transport sites in a cultured human retinal cell line (Williams et al., *Nucleoside Transport Sites in a Cultured Human Retinal Cell Line Established By SV-40 T Antigen Gene, Current Eye Research*, volume 13, pages 109-118 (1994)).

Compounds which regulate the uptake of adenosine have previously been suggested as potential therapeutic agents for the treatment of retinal and optic nerve head damage. In U.S. Pat. No. 5,780,450 to Shade, Shade discusses the use of adenosine uptake inhibitors for treating eye disorders. Shade does not disclose the use of specific $A_3$ receptor inhibitors. The entire contents of U.S. Pat. No. 5,780,450 are hereby incorporated herein by reference.

Additional adenosine receptor antagonists are needed as pharmacological tools and are of considerable interest as drugs for the above-referenced disease states and/or conditions.

SUMMARY OF THE INVENTION

The present invention provides compounds having the formula:

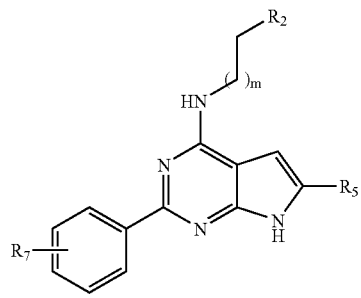

wherein
m is 0, 1, 2, or 3;
$R_2$ is a substituted or unsubstituted imidazole or pyrazole wherein the point of attachment of $R_2$ to the alkyl chain is not N;
$R_5$ is a hydrogen atom or a substituted or unsubstituted alkyl, aryl, or alkylaryl moiety; and
$R_7$ is a halogen atom, e.g., chlorine, fluorine, or bromine, $C_1$-$C_4$ alkyl, OH, O-alkyl($C_1$-$C_4$), $NH_2$, or NH-alkyl ($C_1$-$C_4$).

The present invention also provides a compound having the structure:

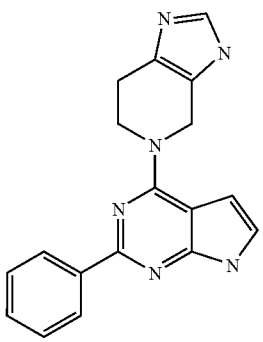

The present invention also provides a method for treating a disease associated with an A3 adenosine receptor by administering a therapeutically effective amount of the any of the compounds described above.

The present invention also provides a compound having the structure:

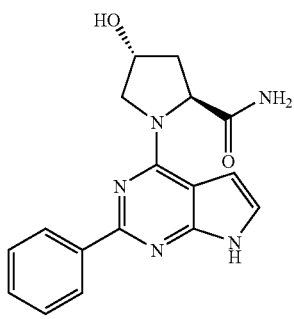

The present invention also provides a method for treating a disease associated with an A1 adenosine receptor by administering a therapeutically effective amount of the above compound.

The present invention also provides prodrugs of any of the compounds described above.

DETAILED DESCRIPTION

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention pertains to methods for treating a N-6 substituted 7-deazapurine responsive state in a mammal. The methods include administration of a therapeutically effective amount of a N-6 substituted 7-deazapurine, described infra, to the mammal, such that treatment of the N-6 substituted 7-deazapurine responsive state in the mammal occurs.

The language "N-6 substituted 7-deazapurine responsive state" is intended to include a disease state or condition characterized by its responsiveness to treatment with a N-6 substituted 7-deazapurine of the invention as described infra, e.g., the treatment includes a significant diminishment of at least one symptom or effect of the state achieved with a N-6 substituted 7-deazapurine of the invention. Typically such states are associated with an increase of adenosine within a host such that the host often experiences physiological symptoms which include, but are not limited to, release of toxins, inflammation, coma, water retention, weight gain or weight loss, pancreatitis, emphysema, rheumatoid arthritis, osteoarthritis, multiple organ failure, infant and adult respiratory distress syndrome, allergic rhinitis, chronic obstructive pulmonary disease, eye disorders, gastrointestinal disorders, skin tumor promotion, immunodeficiency and asthma. (See for example, C. E. Muller and B. Stein "Adenosine Receptor Antagonists: Structures and Potential Therapeutic Applications," *Current Pharmaceutical Design*, 2:501 (1996) and C. E. Muller "$A_1$-Adenosine Receptor Antagonists," *Exp. Opin. Ther. Patents* 7(5):419 (1997) and I. Feoktistove, R. Polosa, S. T. Holgate and I. Biaggioni "Adenosine $A_{2B}$ receptors: a novel therapeutic target in asthma?" TiPS 19; 148 (1998)). The effects often associated with such symptoms include, but are not limited to, fever, shortness of breath, nausea, diarrhea, weakness, headache, and even death. In one embodiment, a N-6 substituted 7-deazapurine responsive state includes those disease states which are mediated by stimulation of adenosine receptors, e.g., $A_1$, $A_{2a}$, $A_{2b}$, $A_3$, etc., such that calcium concentrations in cells and/or activation of PLC (phospholipase C) is modulated. In a preferred embodiment, a N-6 substituted 7-deazapurine responsive state is associated with adenosine receptor(s), e.g., the N-6 substituted 7-deazapurine acts as an antagonist. Examples of suitable responsive states which can be treated by the compounds of the invention, e.g., adenosine receptor subtypes which mediate biological effects, include central nervous system (CNS) effects, cardiovascular effects, renal effects, respiratory effects, immunological effects, gastro-intestinal effects and metabolic effects. The relative amount of adenosine in a subject can be associated with the effects listed below; that is increased levels of adenosine can trigger an effect, e.g., an undesired physiological response, e.g., an asthmatic attack.

CNS effects include decreased transmitter release ($A_1$), sedation ($A_1$), decreased locomotor activity ($A_{2a}$), anticonvulsant activity, chemoreceptor stimulation ($A_2$) and hyperalgesia. Therapeutic applications of the inventive compounds include treatment of dementia, Alzheimer's disease and memory enhancement.

Cardiovascular effects include vasodilation ($A_{2a}$), ($A_{2b}$) and ($A_3$), vasoconstriction ($A_1$), bradycardia ($A_1$), platelet inhibition ($A_{2a}$), negative cardiac inotropy and dromotropy ($A_1$), arrhythmia, tachycardia and angiogenesis. Therapeutic applications of the inventive compounds include, for example, prevention of ischaemia-induced impairment of the heart and cardiotonics, myocardial tissue protection and restoration of cardiac function.

Renal effects include decreased GFR ($A_1$), mesangial cell contraction ($A_1$), antidiuresis ($A_1$) and inhibition of renin release ($A_1$). Suitable therapeutic applications of the inventive compounds include use of the inventive compounds as diuretic, natriuretic, potassium-sparing, kidney-protective/prevention of acute renal failure, antihypertensive, anti-oedematous and anti-nephritic agents.

Respiratory effects include bronchodilation ($A_2$), bronchoconstriction ($A_1$), chronic obstructive pulmonary disease, allergic rhinitis, mucus secretion and respiratory depression ($A_2$). Suitable therapeutic applications for the compounds of the invention include anti-asthmatic applications, treatment of lung disease after transplantation and respiratory disorders.

Immunological effects include immunosuppression ($A_2$), neutrophil chemotaxis ($A_1$), neutrophil superoxide generation ($A_{2a}$) and mast cell degranulation ($A_{2b}$ and $A_3$) Therapeutic applications of antagonists include allergic and non allergic inflammation, e.g., release of histamine and other inflammatory mediators.

Gastrointestinal effects include inhibition of acid secretion ($A_1$) therapeutic application may include reflux and ulcerative conditions Gastrointestinal effects also include colonic, intestinal and diarrheal disease, e.g., diarrheal disease associated with intestinal inflammation ($A_{2b}$).

Eye disorders include retinal and optic nerve head injury and trauma related disorders ($A_3$). In a preferred embodiment, the eye disorder is glaucoma.

Other therapeutic applications of the compounds of the invention include treatment of obesity (lipolytic properties), hypertension, treatment of depression, sedative, anxiolytic, as antileptics and as laxatives, e.g., effecting motility without causing diarrhea.

The term "disease state" is intended to include those conditions caused by or associated with unwanted levels of adenosine, adenylyl cyclase activity, increased physiological activity associated with aberrant stimulation of adenosine receptors and/or an increase in cAMP. In one embodiment, the disease state is, for example, asthma, chronic obstructive pulmonary disease, allergic rhinitis, bronchitis, renal disorders, gastrointestinal disorders, or eye disorders. Additional examples include chronic bronchitis and cystic fibrosis. Suitable examples of inflammatory diseases include non-lymphocytic leukemia, myocardial ischaemia, angina, infarction, cerebrovascular ischaemia, intermittent claudication, critical limb ischemia, venous hypertension, varicose veins, venous ulceration and arteriosclerosis. Impaired reperfusion states include, for example, any post-surgical trauma, such as reconstructive surgery, thrombolysis or angioplasty.

This invention also provides a combination therapy for glaucoma, comprising one of the compounds of the invention, and a prostagladin agonist, beta-2 agonist, or a muniscrinic antagonist.

The language "treatment of a N-6 substituted 7-deazapurine responsive state" or "treating a N-6 substituted 7-deazapurine responsive state" is intended to include changes in a disease state or condition, as described above, such that physiological symptoms in a mammal can be significantly diminished or minimized. The language also includes control, prevention or inhibition of physiological symptoms or effects associated with an aberrant amount of adenosine. In one preferred embodiment, the control of the disease state or condition is such that the disease state or condition is eradicated. In another preferred embodiment, the control is selective such that aberrant levels of adenosine receptor activity are controlled while other physiologic systems and parameters are unaffected.

The term "N-6 substituted 7-deazapurine" is art recognized and is intended to include those compounds having the formula I:

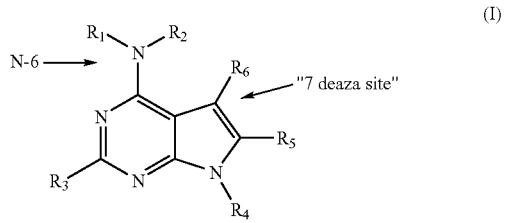

(I)

"N-substituted 7-deazapurine" includes pharmaceutically acceptable salts thereof, and, in one embodiment, also includes certain N-6 substituted purines described herein.

In certain embodiments, the N-6 substituted 7-deazapurine is not N-6 benzyl or N-6 phenylethyl substituted. In other embodiments, $R_4$ is not benzyl or phenylethyl substituted. In preferred embodiments, $R_1$ and $R_2$ are both not hydrogen atoms. In still other preferred embodiments, $R_3$ is not a hydrogen atom.

The language "therapeutically effective amount" of an N-6 substituted 7-deazapurine, described infra, is that amount of a therapeutic compound necessary or sufficient to perform its intended function within a mammal, e.g., treat a N-6 substituted 7-deazapurine responsive state, or a disease state in a mammal. An effective amount of the therapeutic compound can vary according to factors such as the amount of the causative agent already present in the mammal, the age, sex, and weight of the mammal, and the ability of the therapeutic compounds of the present invention to affect a N-6 substituted 7-deazapurine responsive state in the mammal. One of ordinary skill in the art would be able to study the aforementioned factors and make a determination regarding the effective amount of the therapeutic compound without undue experimentation. An in vitro or in vivo assay also can be used to determine an "effective amount" of the therapeutic compounds described infra. The ordinarily skilled artisan would select an appropriate amount of the therapeutic compound for use in the aforementioned assay or as a therapeutic treatment.

A therapeutically effective amount preferably diminishes at least one symptom or effect associated with the N-6 substituted 7-deazapurine responsive state or condition being treated by at least about 20%, (more preferably by at least about 40%, even more preferably by at least about 60%, and still more preferably by at least about 80%) relative to untreated subjects. Assays can be designed by one skilled in the art to measure the diminishment of such symptoms and/or effects. Any art recognized assay capable of measuring such parameters are intended to be included as part of this invention. For example, if asthma is the state being treated, then the volume of air expended from the lungs of a subject can be measured before and after treatment for measurement of increase in the volume using an art recognized technique. Likewise, if inflammation is the state being treated, then the area which is inflamed can be measured before and after treatment for measurement of diminishment in the area inflamed using an art recognized technique.

The term "cell" includes both prokaryotic and eukaryotic cells.

The term "animal" includes any organism with adenosine receptors or any organism susceptible to a N-6-substituted 7-deazapurine responsive state. Examples of animals include yeast, mammals, reptiles, and birds. It also includes transgenic animals.

The term "mammal" is art recognized and is intended to include an animal, more preferably a warm-blooded animal, most preferably cattle, sheep, pigs, horses, dogs, cats, rats, mice, and humans. Mammals susceptible to a N-6 substituted 7-deazapurine responsive state, inflammation, emphysema, asthma, central nervous system conditions, or acute respiratory distress syndrome, for example, are included as part of this invention.

In another aspect, the present invention pertains to methods for modulating an adenosine receptor(s) in a mammal by administering to the mammal a therapeutically effective amount of a N-6 substituted 7-deazapurine, such that modulation of the adenosine receptor in the mammal occurs. Suitable adenosine receptors include the families of $A_1$, $A_2$, or $A_3$ In a preferred embodiment, the N-6 substituted 7-deazapurine is an adenosine receptor antagonist.

The language "modulating an adenosine receptor" is intended to include those instances where a compound interacts with an adenosine receptor(s), causing increased, decreased or abnormal physiological activity associated with an adenosine receptor or subsequent cascade effects resulting from the modulation of the adenosine receptor. Physiological activities associated with adenosine receptors include induction of sedation, vasodilation, suppression of cardiac rate and contractility, inhibition of platelet aggregbility, stimulation of gluconeogenesis, inhibition of lipolysis, opening of potassium channels, reducing flux of calcium channels, etc.

The terms "modulate", "modulating" and "modulation" are intended to include preventing, eradicating, or inhibiting the resulting increase of undesired physiological activity associated with abnormal stimulation of an adenosine receptor, e.g., in the context of the therapeutic methods of the invention. In another embodiment, the term modulate includes antagonistic effects, e.g., diminishment of the activity or production of mediators of allergy and allergic inflammation which results from the overstimulation of adenosine receptor(s). For example, the therapeutic deazapurines of the invention can interact with an adenosine receptor to inhibit, for example, adenylate cyclase activity.

The language "condition characterized by aberrant adenosine receptor activity" is intended to include those diseases, disorders or conditions which are associated with aberrant stimulation of an adenosine receptor, in that the stimulation of the receptor causes a biochemical and or physiological chain of events that is directly or indirectly associated with the disease, disorder or condition. This stimulation of an adenosine receptor does not have to be the sole causative agent of the disease, disorder or condition but merely be responsible for causing some of the symptoms typically associated with the disease, disorder, or condition being treated. The aberrant stimulation of the receptor can be the sole factor or at least one other agent can be involved in the state being treated. Examples of conditions include those disease states listed supra, including inflammation, gastrointestinal disorders and those symptoms manifested by the presence of increased adenosine receptor activity. Preferred examples include those symptoms associated with asthma, allergic rhinitis, chronic obstructive pulmonary disease, emphysema, bronchitis, gastrointestinal disorders and glaucoma.

The language "treating or treatment of a condition characterized by aberrant adenosine receptor activity" is intended to include the alleviation of or diminishment of at least one symptom typically associated with the condition. The treatment also includes alleviation or diminishment of more than one symptom. Preferably, the treatment cures, e.g., substantially eliminates, the symptoms associated with the condition.

The compounds of the invention may comprise water-soluble prodrugs which are described in WO 99/33815, International Application No. PCT/US98/04595, filed Mar. 9, 1998 and published Jul. 8, 1999. The entire content of WO 99/33815 is expressly incorporated herein by reference. The water-soluble prodrugs are metabolized in vivo to an active drug, e.g., by esterase catalyzed hydrolysis. Examples of potential prodrugs include deazapurines with, for example, $R_2$ as cycloalkyl substituted with —OC(O)(Z)NH$_2$, wherein Z is a side chain of a naturally or unnaturally occurring amino acid, or analog thereof, an α, β, γ, or ω amino acids, or a dipeptide. Preferred amino acid side chains include those of glycine, alanine, valine, leucine, isoleucine, lysine, α-methylalanine, aminocyclopropane carboxylic acid, azetidine-2-carboxylic acid, β-alanine, γ-aminobutyric acid, alanine-alanine, or glycine-alanine.

In a particularly preferred embodiment, the deazapurines of the invention are water-soluble prodrugs that can be metabolized in vivo to an active drug, e.g. by esterase catalyzed hydrolysis.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 4-10 carbon atoms in their ring structure, and more preferably have 5, 6 or 7 carbons in the ring structure.

Moreover, the term "alkyl" as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above but that contain at least one double or triple bond respectively.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" refer to unsaturated aliphatic groups analogous in length and possible substitution to the alkyls described above, but that contain at least one double or triple bond respectively. For example, the invention contemplates cyano and propargyl groups.

Unless the number of carbons is otherwise specified, "lower alkyl", as used herein means an alkyl group, as defined above, but having from one to ten carbons, more preferably from one to six carbon atoms in its backbone structure, even more preferably one to three carbon atoms in its backbone structure. Likewise, "lower alkenyl" and "lower alkynyl" have similar chain lengths.

The terms "alkoxyalkyl", "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" as used herein means an atom of any element other than carbon or hydrogen. Preferred heteroatoms are nitrogen, oxygen, sulfur and phosphorus.

The term "amino acids" includes naturally and unnaturally occurring amino acids found in proteins such as glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan. Amino acid analogs include amino acids with lengthened or shortened side chains or variant side chains with appropriate functional groups. Amino acids also include D and L stereoisomers of an amino acid when the structure of the amino acid admits of stereoisomeric forms. The term "dipeptide" includes two or more amino acids linked together. Preferably, dipeptides are two amino acids linked via a peptide linkage. Particularly preferred dipeptides include, for example, alanine-alanine and glycine-alanine.

It will be noted that the structure of some of the compounds of this invention includes asymmetric carbon atoms and thus occur as racemates and racemic mixtures, single enantiomers, diastereomeric mixtures and individual diastereomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis.

The invention further pertains to pharmaceutical compositions for treating a N-6 substituted 7-deazapurine responsive state in a mammal, e.g., respiratory disorders (e.g., asthma, bronchitis, chronic obstructive pulmonary disorder, and allergic rhinitis), renal disorders, gastrointestinal disorders, and eye disorders. The pharmaceutical composition includes a therapeutically effective amount of a N-6 substituted 7-deazapurine and a pharmaceutically acceptable carrier. It is to be understood, that all of the deazapurines described below are included for therapeutic treatment. It is to be further understood that the deazapurines of the invention can be used alone or in combination with other deazapurines of the invention or in combination with additional therapeutic compounds, such as antibiotics, antiinflammatories, or anticancer agents, for example.

The term "antibiotic" is art recognized and is intended to include those substances produced by growing microorganisms and synthetic derivatives thereof, which eliminate or inhibit growth of pathogens and are selectively toxic to the pathogen while producing minimal or no deleterious effects upon the infected host subject. Suitable examples of antibiotics include, but are not limited to, the principle classes of aminoglycosides, cephalosporins, chloramphenicols, fuscidic acids, macrolides, penicillins, polymixins, tetracyclines and streptomycins.

The term "antiinflammatory" is art recognized and is intended to include those agents which act on body mechanisms, without directly antagonizing the causative agent of the inflammation such as glucocorticoids, aspirin, ibuprofen, NSAIDS, etc.

The term "anticancer agent" is art recognized and is intended to include those agents which diminish, eradicate, or prevent growth of cancer cells without, preferably, adversely affecting other physiological functions. Representative examples include cisplatin and cyclophosphamide.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can performs its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

As set out above, certain embodiments of the present compounds can contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. Hydroxyl containing derivatives can be converted into esters via treatment with an esterifying agent such as alkanoyl halides. The term is further intended to include lower hydrocarbon groups capable of being solvated under physiological conditions, e.g., alkyl esters, methyl, ethyl and propyl esters. (See, for example, Berge et al., supra.)

The invention further contemplates the use of prodrugs which are converted in vivo to the therapeutic compounds of the invention (see, e.g., R. B. Silverman, 1992, "The Organic Chemistry of Drug Design and Drug Action", Academic Press, Chapter 8). Such prodrugs can be used to alter the biodistribution (e.g., to allow compounds which would not typically enter the reactive site of the protease) or the pharmacokinetics of the therapeutic compound. For example, a carboxylic acid group, can be esterified, e.g., with a methyl group or an ethyl group to yield an ester. When the ester is administered to a subject, the ester is cleaved, enzymatically or non-enzymatically, reductively or hydrolytically, to reveal the anionic group. An anionic group can be esterified with moieties (e.g., acyloxymethyl esters) which are cleaved to reveal an intermediate compound which subsequently decomposes to yield the active compound. In another embodiment, the prodrug is a reduced form of a sulfate or sulfonate, e.g., a thiol, which is oxidized in vivo to the therapeutic compound. Furthermore, an anionic moiety can be esterified to a group which is actively transported in vivo, or which is selectively taken up by target organs. The ester can be selected to allow specific targeting of the therapeutic moieties to particular reactive sites, as described below for carrier moieties.

Carrier Linkages for Various Functional Groups a. Alcohols and Carboxylic Acids. There are several reasons why the most common prodrug form for drugs containing alcohol or carboxylic acid functional groups is an ester. First, esterases are ubiquitous, so metabolic regeneration of the drug is a facile process. Also, it is possible to prepare ester derivatives with virtually any degree of hydrophilicity or lipophilicity. Finally, a variety of stabilities of esters can be obtained by appropriate manipulation of electronic and steric factors. Therefore, a multitude of ester prodrugs can be prepared to accomodate a wide variety of problems that require the prodrug approach.

Alcohol-containing drugs can be acylated with aliphatic or aromatic carboxylic acids to decrease water solubility (increase lipophilicity) or with carboxylic acids containing amino or additional carboxylate groups to increase water solubility. Conversion to phosphate or sulfate esters also increases water solubility. By using these approaches a wide range of solubilities can be achieved that will affect the absorption and distribution properties of the drug. These derivatives also can have an important effect on the dosage form, that is, whether used in a tablet form or in aqueous solution. One problem with the use of this prodrug approach is that in some cases the esters are not very good substrates for the endogenous esterases, sulfatases, or phosphatases, and they may not be hydrolized at a rapid enough rate. When that occurs, however, a different ester can be tried. Another approach to accelerate the hydrolysis rate could be to attach electron-withdrawing groups (if a base hydrolysis mechanism is relevant) or electron-donating groups (if an acid hydrolysis mechanism is important) to the carboxylate side of the ester. Succinate esters can be used to accelerate the rate of hydrolysis by intramolecular catalysis. If the ester is too reactive, substituents can be appended that cause steric hindrance to hydrolysis. Alcohol-containing drugs also can be converted to the corresponding acetals or ketals for rapid hydrolysis in the acidic medium of the gastrointestinal tract.

Carboxylic acid-containing drugs also can be esterified; the reactivity of the derivatized drug can be adjusted by the appropriate structural manipulations. If a slower rate of ester hydrolysis is desired, long-chain aliphatic or sterically hindered esters can be used. If hydrolysis is too slow, addition of electron-withdrawing groups on the alcohol part of the ester can increase the rate. The pKa of a carboxylic acid can be raised by conversion to a choline ester or an amino ester.

b. Amines. N-Acylation of amines to give amide prodrugs is not commonly used, in general, because of the stability of amides toward metabolic hydrolysis. Activated amides, generally of low basicity amines, or amides of amino acids are more susceptible to enzymatic cleavage. Although carbamates in general are too stable, phenyl carbamates (RNHCO2Ph) are rapidly cleaved by plasma enzymes, and, therefore, they can be used as prodrugs.

The pKa values of amines can be lowered by approximately 3 units by conversion to their N-Mannich bases. This lowers the basicity of the amine so that at physiological Ph few of the prodrug molecules are protonated, thereby increasing its lipophilicity. For example, the partition coefficient between octanol and phosphate buffer, pH 7.4, for the N-Mannich base derived from benzamide and the decongestant phenylpropanolamine is almot 100 times greater than that for the parent amine. However, the rate of hydrolysis of N-Mannich bases depends on the amide carrier group; salicylamide and succinimide are more susceptible to hydrolysis than is benzamide.

Another approach for lowering the pKa values of amines and, thereby, making them more lipophilic, is to convert them to imines (Schiff bases); however, imines often are to labile in aqueous solution. The anticonvulsant agent progabide (8.3) is a prodrug from of γ-aminobutyric acid, an important inhibitory neurotransmitter. The lipophilicity of 8.3 allows the compound to cross the blood-brain barrier; once inside the brain it is hydrolized to γ-aminobutyric acid.

c. Carbonyl Compounds. The most important prodrug forms of aldehydes and ketones are Schiff bases, oximes, acetals (ketals), enol esters, oxazolidines, and thiazolidines (Table 8.3). A more complete review of bioreversible derivatives of the functional groups was written by Bundgaard.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert dilutents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert dilutents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention. Preferably, the pharmaceutical preparation is an ophthalmic formulation (e.g., an periocular, retrobulbar or intraocular injection formulation, a systemic formulation, or a surgical irrigating solution).

The ophthalmic formulations of the present invention may include one or more deazapurines and a pharmaceutically acceptable vehicle. Various types of vehicles may be used. The vehicles will generally be aqueous in nature. Aqueous solutions are generally preferred, based on ease of formulation, as well as a patient's ability to easily administer such compositions by means of instilling one to two drops of the solutions in the affected eyes. However, the deazapurines of the present invention may also be readily incorporated into other types of compositions, such as suspensions, viscous or semi-viscous gels or other types of solid or semi-solid compositions. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v").

When the deazapurines of the present invention are administered during intraocular surgical procedures, such as through retrobulbar or periocular injection and intraocular perfusion or injection, the use of balanced salt irrigating solutions as vehicles are most preferred. BSS® Sterile Irrigating Solution and BSS Plus® Sterile Intraocular Irrigating Solution (Alcon Laboratories, Inc., Fort Worth, Tex., USA) are examples of physiologically balanced intraocular irrigating solutions. The latter type of solution is described in U.S. Pat. No. 4,550,022 (Garabedian, et al.), the entire contents of which are hereby incorporated in the present specification by reference. Retrobulbar and periocular injections are known to those skilled in the art and are described in numerous publications including, for example, *Ophthalmic Surgery: Principles of Practice*, Ed., G. L. Spaeth. W. B. Sanders Co., Philadelphia, Pa., U.S.A., pages 85-87 (1990).

As indicated above, use of deazapurines to prevent or reduce damage to retinal and optic nerve head tissues at the cellular level is a particularly important aspect of one embodiment of the invention. Ophthalmic conditions which may be treated include, but are not limited to, retinopathies, macular degeneration, ocular ischemia, glaucoma, and damage associated with injuries to ophthalmic tissues, such as ischemia reperfusion injuries, photochemical injuries, and injuries associated with ocular surgery, particularly injuries to the retina or optic nerve head by exposure to light or surgical instruments. The compounds may also be used as an adjunct to ophthalmic surgery, such as by vitreal or subconjunctival injection following ophthalmic surgery. The compounds may be used for acute treatment of temporary conditions, or may be administered chronically, especially in the case of degenerative disease. The compounds may also be used prophylactically, especially prior to ocular surgery or noninvasive ophthalmic procedures, or other types of surgery.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 200 mg per kilogram of body weight per day, more preferably from about 0.01 to about 150 mg per kg per day, and still more preferably from about 0.2 to about 140 mg per kg per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

The present invention also pertains to packaged pharmaceutical compositions for treating a N-6 substituted 7 deazapurine responsive state, e.g., undesirable increased adenosine receptor activity in a mammal. The packaged pharmaceutical compositions include a container holding a therapeutically effective amount of at least one deazapurine as described supra and instructions for using the deazapurine for treating the deazapurine responsive state in the mammal.

The present invention also features compounds having the formula (XI):

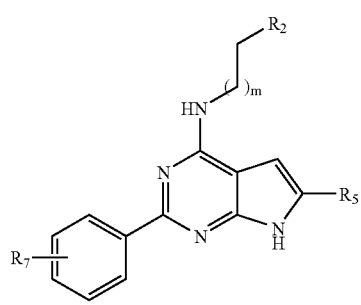

XI wherein
m is 0, 1, 2, or 3;
R$_2$ is a substituted or unsubstituted imidazole or pyrazole wherein the point of attachment of R$_2$ to the alkyl chain is not N;
R$_5$ is a hydrogen atom or a substituted or unsubstituted alkyl, aryl, or alkylaryl moiety; and
R$_7$ is a halogen atom, e.g., chlorine, fluorine, or bromine, C$_1$-C$_4$ alkyl, OH, O-alkyl(C$_1$-C$_4$), NH$_2$, or NH-alkyl (C$_1$-C$_4$).

In a preferred embodiment of the invention, the compound has the structure:

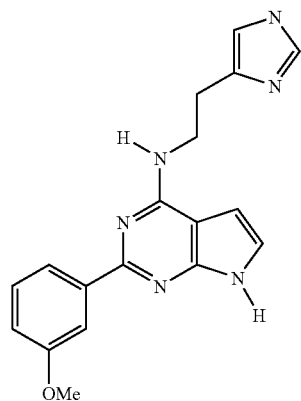

1735

This invention also provides a compound having the structure:

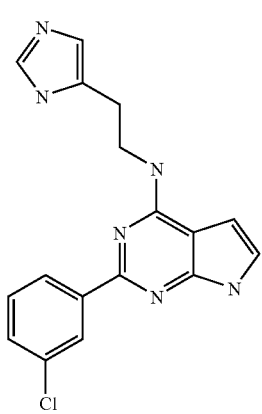

1721

This invention also provides a compound having the structure:

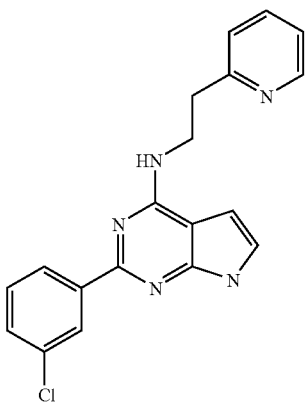

1722

This invention also provides a compound having the structure:

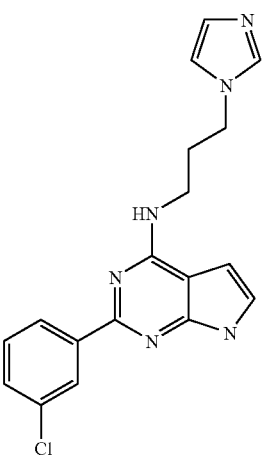

1723

This invention also provides a compound having the structure:

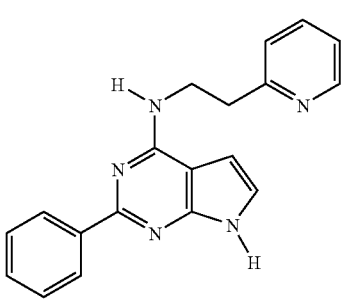

1724

This invention also provides a compound having the structure:

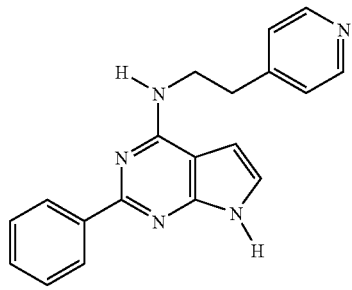
1725

This invention also provides a compound having the structure:

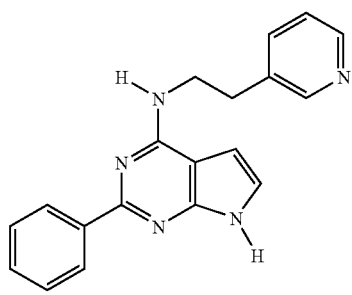
1726

This invention also provides a compound having the structure:

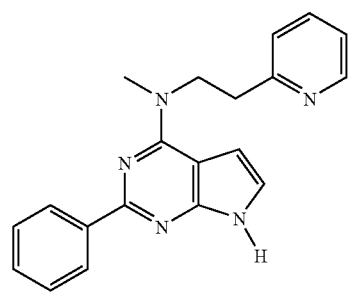
1727

This invention also provides a compound having the structure:

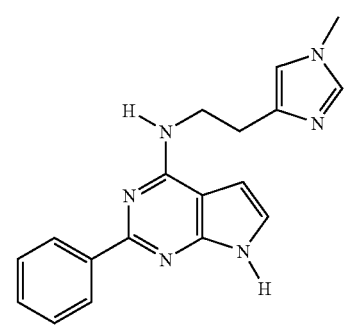
1728

This invention also provides a compound having the structure:

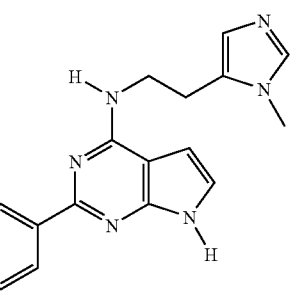
1729

This invention also provides a compound having the structure:

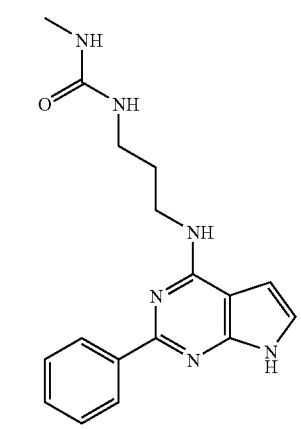
1730

This invention also provides a compound having the structure:

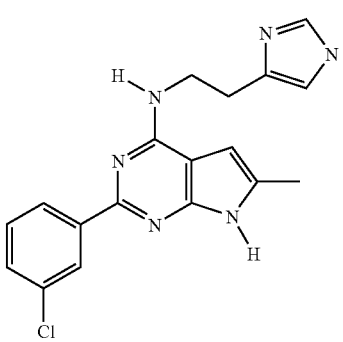
1731

This invention also provides a compound having the structure:

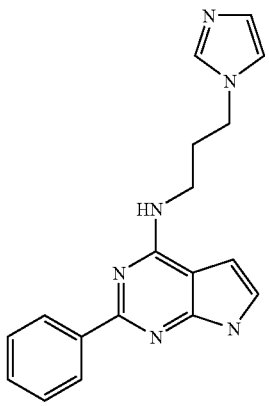

1732

This invention also provides a compound having the structure:

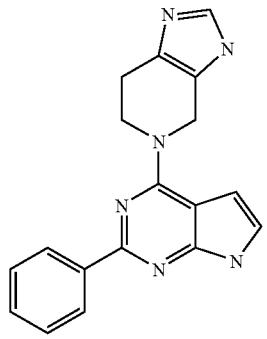

1733

Another compound known to have activity as an inhibitor of the A3 adenosine receptor is the compound having the structure:

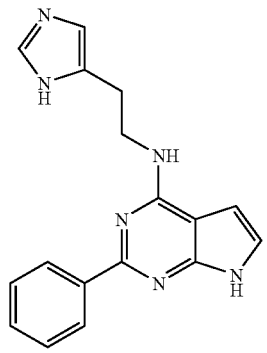

1720

Compound 1720 is more fully described in PCT International Publication No. WO 02/057267 A1. Compound 1720 was used as a benchmark to evaluate the activity of the compounds of the invention.

This invention also provides a compound having the structure:

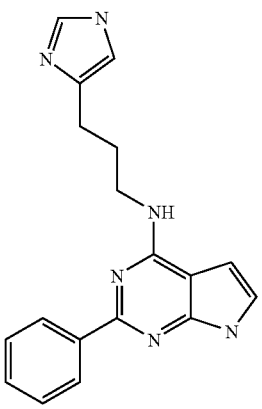

1734

This invention also provides a compound having the structure:

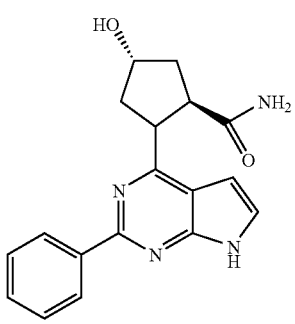

1631

This invention also provides a method for treating a disease associated with an A3 adenosine receptor in a subject in need of such treatment, comprising administering to the subject a therapeutically effective amount of compound 1720, 1721, 1722, 1723, 1724, 1725, 1726, 1727, 1728, 1729, 1730, 1731, 1732, 1733, 1734 or 1735 so as to thereby treat the disease associated with the A3 adenosine receptor in the subject, wherein the disease associated with the A3 adenosine receptor is cardiac hypoxia, cerebral ischemia, antidiuresis, myocardial ischemia, bronchoconstriction, diabetes, asthma, bronchitis, glaucoma, retinopathy, ocular ischemia, macular degeneration, a gastrointestinal disorder, a respiratory disorder, inflammation of the eye, or whereby the disease associated with the A3 adenosine receptor is associated with mast cell degranulation or eosinophil activity.

In one embodiment of the method, the disease associated with the A3 adenosine receptor is cardiac hypoxia, cerebral ischemia, antidiuresis, myocardial ischemia, bronchoconstriction or diabetes.

In another embodiment, the disease associated with the A3 adenosine receptor is a gastrointestinal disorder.

In a further embodiment of the above method, the gastrointestinal disorder is diarrhea.

In a further embodiment, the disease associated with the A3 adenosine receptor is a respiratory disorder.

In a further embodiment of the above method, the respiratory disorder is asthma, bronchitis, chronic obstructive pulmonary disease, allergic rhinitis or an upper respiratory disorder.

In another embodiment, the disease associated with the A3 adenosine receptor is inflammation of the eye.

In another embodiment, the disease associated with the A3 adenosine receptor is associated with mast cell degranulation or eosinophil activity.

In another embodiment, the disease associated with the A3 adenosine receptor is asthma, glaucoma, retinopathy, ocular ischemia, or macular degeneration.

In a further embodiment of the above method, the disease is asthma.

In a further embodiment of the above method, the disease is glaucoma.

In a further embodiment of the above method, the method further comprises administering to the subject a therapeutically effective amount of one or more compounds selected from the group consisting of beta adrenoceptor antagonists, alpha-2 adrenoceptor agonists, carbonic anhydrase inhibitors, cholinergic agonists, prostaglandins and prostaglandin receptor agonists, angiotensin converting enzyme (ACE) inhibitors, AMPA receptor antagonists, 5-HT agonists, angiogenesis inhibitors, NMDA antagonists, renin inhibitors, cannabinoid receptor agonists, angiotensin receptor antagonists, hydrochlorothiazide (HCTZ), somatostatin agonists, glucocorticoid antagonists, mast cell degranulation inhibitors, alpha-adrenergic receptor blockers, alpha-2 adrenoceptor antagonists, thromboxane A2 mimetics, protein kinase inhibitors, prostaglandin F derivatives, prostaglandin-2 alpha antagonists, dopamine D1 and 5-HT2 agonists, nitric-oxide-releasing agents, 5-HT 2 antagonists, cyclooxygenase inhibitors, inosine, dopamine D2 receptor and alpha 2 adrenoceptor agonists, dopamine D1 receptor antagonist and D2 receptor agonists, vasopressin receptor antagonists, endothelin antagonists, 1-(3-hydroxy-2-phosphonylmethoxypropyl)cytosine (HPMPC) and related analogs and prodrugs, thyroid hormone receptor ligands, muscarinic M1 agonists, sodium channel blockers, mixed-action ion channel blockers, beta adrenoceptor antagonist and PGF2 alpha agonist combinations, guanylate cyclase activators, nitrovasodilators, endothelin receptor modulators, ethacrynic acid, other phenoxyacetic acid analogs, actin disrupters, calcium channel blockers and neuroprotective agents.

In a further embodiment of the above method, the method further comprises administering to the subject a therapeutically effective amount of one or more compounds selected from the group consisting of beta adrenoceptor antagonists, alpha-2 adrenoceptor agonists, carbonic anhydrase inhibitors, cholinergic agonists and prostaglandin receptor agonists.

In a further embodiment of the above method, the method further comprises administering to the subject a therapeutically effective amount of a prostaglandin agonist, β2 agonist, or a muniscrinic antagonist.

This invention also provides a method for treating a disease associated with an $A_1$ adenosine receptor in a subject in need of such treatment, comprising administering to the subject a therapeutically effective amount of compound 1631 so as to thereby treat the disease associated with the A1 adenosine receptor in the subject wherein the disease associated with the A1 adenosine receptor is cognitive disease, a respiratory disorder, a reflux condition, an ulcerative condition, congestive heart failure, renal failure, cardiac arrhythmias, respiratory epithelia, transmitter release, sedation, vasoconstriction, bradycardia, negative cardiac inotropy and dromotropy, bronchoconstriction, bronchitis or neutrophil chemotaxis.

In one embodiment, the cognitive disease is a memory disorder.

This invention also provides a method for treating a disease associated with an $A_1$ adenosine receptor in a subject in need of such treatment, comprising administering to the subject a therapeutically effective amount of compound 1631 so as to thereby treat the disease associated with the A1 adenosine receptor in the subject wherein the disease associated with the A1 adenosine receptor is antidiuresis, cardiac hypoxia, myocardial ischemia, hypertension, inflammation, or is associated with contraction of smooth muscle underlying respiratory epithelia, mast cell degranulation or eosinophil activity.

In one embodiment, the respiratory disorder is asthma, chronic obstructive pulmonary disease, bronchitis, allergic rhinitis, or an upper respiratory disorder.

In a further embodiment of the above method, the disorder is asthma.

In a further embodiment of the above method, the method further comprises administering to the subject at least one of either a steroid, a β2 agonist, a glucocorticoid, a leukotriene antagonist, or an anticolinergic agonist so as to thereby treat asthma in the subject.

In another embodiment, the disease associated with the A1 adenosine receptor is congestive heart failure.

In a further embodiment of any of the above methods, the subject is human.

This invention also provides a method of inducing diuresis in a subject, comprising administering a diuretically effective amount of compound 1631 so as to thereby induce diuresis in the subject.

This invention also provides a method for inhibiting the activity of an A3 adenosine receptor in a cell that is subjected to abnormal stimulation of the A3 adenosine receptor, which comprises contacting the cell with compound 1720, 1721, 1722, 1723, 1724, 1725, 1726, 1727, 1728, 1729, 1730, 1731, 1732, 1733, 1734 or 1735, so as to inhibit the activity of the A3 adenosine receptor.

This invention also provides a method for inhibiting the activity of an $A_1$ adenosine receptor in a cell that is subjected to abnormal stimulation of the A1 adenosine receptor, which comprises contacting the cell with compound 1631, so as to inhibit the activity of the A1 adenosine receptor.

In a further embodiment of the above methods, the cell is a human cell.

This invention also provides a prodrug of compound 1720, 1721, 1722, 1723, 1724, 1725, 1726, 1727, 1728, 1729, 1730, 1731, 1732, 1733, 1734 or 1735, wherein the prodrug is metabolized in vivo by a human subject to an active drug which selectively inhibits the A3 adenosine receptor wherein the prodrug is an ester of an alcohol or carboxylic acid group, if such a group is present in the compound;

an acetal or ketal of an alcohol group, if such a group is present in the compound;

an N-Mannich base or an imine of an amine group, if such a group is present in the compound; or a Schiff base, oxime, acetal, enol ester, oxazolidine, or thiazolidine of a carbonyl group, if such a group is present in the compound.

This invention also provides a prodrug of compound 1631, wherein the prodrug is metabolized in vivo by a human subject to an active drug which selectively inhibits the A1 adenosine receptor wherein the prodrug is an ester of an alcohol or carboxylic acid group, if such a group is present in the compound;

an acetal or ketal of an alcohol group, if such a group is present in the compound;

an N-Mannich base or an imine of an amine group, if such a group is present in the compound; or a Schiff base, oxime, acetal, enol ester, oxazolidine, or thiazolidine of a carbonyl group, if such a group is present in the compound.

In one embodiment, the prodrug is water-soluble.

In one embodiment, the prodrug is metabolized in vivo by esterase catalyzed hydrolysis.

This invention also provides a pharmaceutical composition comprising the prodrug and a pharmaceutically acceptable carrier.

This invention also provides a pharmaceutical composition comprising compound 1631, a pharmaceutically acceptable carrier and at least one of either a steroid, a β2 agonist, a glucocorticoid, a leukotriene antagonist, or an anticolinergic agonist.

This invention also provides a pharmaceutical composition comprising compound 1720, 1721, 1722, 1723, 1724, 1725, 1726, 1727, 1728, 1729, 1730, 1731, 1732, 1733, 1734, 1735 or 1631, and a pharmaceutically acceptable carrier.

In one embodiment, the pharmaceutical composition is an periocular, retrobulbar or intraocular injection formulation.

In another embodiment, the pharmaceutical composition is a systemic formulation.

In another embodiment, the pharmaceutical composition is a surgical irrigating solution.

This invention also provides a packaged pharmaceutical composition for treating a disease associated with an A3 adenosine receptor in a subject, comprising:

(a) a container holding a therapeutically effective amount of compound 1720, 1721, 1722, 1723, 1724, 1725, 1726, 1727, 1728, 1729, 1730, 1731, 1732, 1733, 1734 or 1735; and (b) instructions for using the compound for treating the disease in a subject.

This invention also provides a packaged pharmaceutical composition for treating a disease associated with an A1 adenosine receptor in a subject, comprising:

(a) a container holding a therapeutically effective amount of compound 1631; and (b) instructions for using the compound for treating the disease in a subject.

This invention also provides a method of making a composition which comprises compound 1720, 1721, 1722, 1723, 1724, 1725, 1726, 1727, 1728, 1729, 1730, 1731, 1732, 1733, 1734 or 1735, comprising admixing the compound with a suitable carrier.

The invention also provides a pharmaceutically acceptable salt of compound 1720, 1721, 1722, 1723, 1724, 1725, 1726, 1727, 1728, 1729, 1730, 1731, 1732, 1733, 1734 or 1735.

In one embodiment, the pharmaceutically acceptable salt contains an anion selected from the group consisting of maleic, fumaric, tartaric, acetate, phosphate and mesylate.

The invention also provides the use of compound 1720, 1721, 1722, 1723, 1724, 1725, 1726, 1727, 1728, 1729, 1730, 1731, 1732, 1733, 1734 or 1735 for manufacturing a medicament useful for treating a disease associated with an A3 adenosine receptor in a subject in need of such treatment, wherein the disease associated with the A3 adenosine receptor is cardiac hypoxia, cerebral ischemia, antidiuresis, myocardial ischemia, bronchoconstriction, diabetes, asthma, glaucoma, bronchitis, retinopathy, ocular ischemia, macular degeneration, a gastrointestinal disorder, a respiratory disorder, inflammation of the eye, or whereby the disease associated with the A3 adenosine receptor is associated with mast cell degranulation or eosinophil activity.

In one embodiment, the disease associated with the A3 adenosine receptor is cardiac hypoxia, cerebral ischemia, antidiuresis, myocardial ischemia, bronchoconstriction or diabetes.

In another embodiment, the disease associated with the A3 adenosine receptor is a gastrointestinal disorder.

In a further embodiment, the gastrointestinal disorder is diarrhea.

In another embodiment, the disease associated with the A3 adenosine receptor is a respiratory disorder.

In a further embodiment, the respiratory disorder is asthma, bronchitis, chronic obstructive pulmonary disease, allergic rhinitis or an upper respiratory disorder.

In another embodiment, the disease associated with the A3 adenosine receptor is inflammation of the eye.

In another embodiment, the disease associated with the A3 adenosine receptor is asthma, glaucoma, retinopathy, ocular ischemia, or macular degeneration.

In a further embodiment, the disease is asthma.

In a further embodiment, the disease is glaucoma.

In a further embodiment of the above use, the medicament further comprises one or more compounds selected from the group consisting of beta adrenoceptor antagonists, alpha-2 adrenoceptor agonists, carbonic anhydrase inhibitors, cholinergic agonists, prostaglandins and prostaglandin receptor agonists, angiotensin converting enzyme (ACE) inhibitors, AMPA receptor antagonists, 5-HT agonists, angiogenesis inhibitors, NMDA antagonists, renin inhibitors, cannabinoid receptor agonists, angiotensin receptor antagonists, hydrochlorothiazide (HCTZ), somatostatin agonists, glucocorticoid antagonists, mast cell degranulation inhibitors, alpha-adrenergic receptor blockers, alpha-2 adrenoceptor antagonists, thromboxane A2 mimetics, protein kinase inhibitors, prostaglandin F derivatives, prostaglandin-2 alpha antagonists, dopamine D1 and 5-HT2 agonists, nitric-oxide-releasing agents, 5-HT 2 antagonists, cyclooxygenase inhibitors, inosine, dopamine D2 receptor and alpha 2 adrenoceptor agonists, dopamine D1 receptor antagonist and D2 receptor agonists, vasopressin receptor antagonists, endothelin antagonists, 1-(3-hydroxy-2-phosphonylmethoxypropyl)cytosine (HPMPC) and related analogs and prodrugs, thyroid hormone receptor ligands, muscarinic M1 agonists, sodium channel blockers, mixed-action ion channel blockers, beta adrenoceptor antagonist and PGF2 alpha agonist combinations, guanylate cyclase activators, nitrovasodilators, endothelin receptor modulators, ethacrynic acid, other phenoxyacetic acid analogs, actin disrupters, calcium channel blockers and neuroprotective agents.

In a further embodiment of the above use, the medicament further comprises one or more compounds selected from the group consisting of beta-adrenoceptor antagonists, alpha-2 adrenoceptor agonists, carbonic anhydrase inhibitors, cholinergic agonists and prostaglandin receptor agonists.

In a further embodiment of the above use, the medicament further comprises a prostaglandin agonist, β2 agonist, or a muniscrinic antagonist.

In another embodiment, the disease associated with the A3 adenosine receptor is associated with mast cell degranulation or eosinophil activity.

The invention also provides the use of compound 1631 for manufacturing a medicament useful for treating a disease associated with an $A_1$ adenosine receptor in a subject in need of such treatment, wherein the disease associated with the A1 adenosine receptor is cognitive disease, a respiratory disorder, a reflux condition, an ulcerative condition, congestive heart failure, renal failure, cardiac arrhythmias, respiratory epithelia, transmitter release, sedation, vasoconstriction, bradycardia, negative cardiac inotropy and dromotropy, bronchoconstriction, bronchitis or neutrophil chemotaxis.

In one embodiment, the cognitive disease is a memory disorder.

The invention also provides the use of compound 1631 for manufacturing a medicament useful for treating a disease associated with an $A_1$ adenosine receptor in a subject in need of such treatment, wherein the disease associated with the A1 adenosine receptor is antidiuresis, cardiac hypoxia, myocardial ischemia, hypertension, inflammation, or is associated with contraction of smooth muscle underlying respiratory epithelia, mast cell degranulation or eosinophil activity.

In one embodiment, the respiratory disorder is asthma, chronic obstructive pulmonary disease, bronchitis, allergic rhinitis, or an upper respiratory disorder.

In a further embodiment, the respiratory disorder is asthma.

In a further embodiment of the above use, the medicament further comprises at least one of either a steroid, a β2 agonist, a glucocorticoid, a leukotriene antagonist, or an anticolinergic agonist.

The invention also provides for the use of compound 1631 for manufacturing a medicament useful for inducing diuresis in a subject.

In another embodiment, the disease associated with the A1 adenosine receptor is congestive heart failure.

This invention also provides a method for treating a disease associated with an A3 adenosine receptor in a subject, comprising administering to the subject a therapeutically effective amount of compounds of formula XI, preferably 1735, or compound 1720, 1721, 1722, 1723, 1724, 1725, 1726, 1727, 1728, 1729, 1730, 1731, 1732, 1733, or 1734.

This invention also provides a method for treating a disease associated with an $A_1$ adenosine receptor in a subject, comprising administering to the subject a therapeutically effective amount of compound 1631.

In one embodiment of the method, the subject is a mammal.

In another embodiment of the method, the mammal is a human.

In another embodiment of the method, said A3 adenosine receptor is associated with a central nervous system disorder, a cardiovascular disorder, asthma, hypersensitivity, rhinitis, hay fever, serum sickness, allergic vasculitis, atopic dermatitis, dermatitis, psoriasis, eczema, idiopathic pulmonary fibrosis, eosinophilic chlorecystitis, chronic airway inflammation, hypereosinophilic syndromes, eosinophilic gastroenteritis, edema, urticaria, eosinophilic myocardial disease, episodic. angioedema with eosinophilia, inflammatory bowel disease, ulcerative colitis, allergic granulomatosis, carcinomatosis, eosinophilic granuloma, familial histiocytosis, hypertension, mast cell degranulation, tumor, cardiac hypoxia, cerebral ischemia, diuresis, renal failure, neurological disorder, mental disorder, cognitive disorder, myocardial ischemia, bronchoconstriction, arthritis, autoimmune disease, Crohn's disease, Grave's disease, diabetes, multiple sclerosis, anaemia, fertility disorders, lupus erthyematosus, reperfusion injury, brain arteriole diameter, the release of allergic mediators, scleroderma, stroke, global ischemia, central nervous system disorder, cardiovascular disorder, renal disorder, inflammatory disorder, gastrointestinal disorder, eye disorder, allergic disorder, respiratory disorder, or immunological disorder.

In a further embodiment the invention provides the above method, wherein said A1 adenosine receptor is associated with cognitive disease, renal failure, cardiac arrhythmias, respiratory epithelia, transmitter release, sedation, vasoconstriction, bradycardia, negative cardiac inotropy and dromotropy, branchoconstriction, neutrophil chemotaxis, reflux condition, or ulcerative condition.

Diseases associated with adenosine A1, A2a, A2b and A3 receptors are disclosed in WO 99/06053 and WO-09822465, WO-09705138, WO-09511681, WO-09733879, JP-09291089, PCT/US98/16053 and U.S. Pat. No. 5,516,894, the entire content of which are fully incorporate herein by reference.

This invention also provides a water-soluble prodrug of the compounds of formula XI and compounds 1720, 1721, 1722, 1723, 1724, 1725, 1726, 1727, 1728, 1729, 1730, 1731, 1732, 1733, 1734, and 1735, wherein the water-soluble prodrug is metabolized in vivo to produce an active drug which selectively inhibits the A3 adenosine receptor.

This invention also provides a water-soluble prodrug of compound 1631, wherein the water-soluble prodrug is metabolized in vivo to produce an active drug which selectively inhibits the $A_1$ adenosine receptor.

In one embodiment of the prodrug, said prodrug is metabolized in vivo by esterase catalyzed hydrolysis.

This invention also provides a pharmaceutical composition comprising the prodrug and a pharmaceutically acceptable carrier.

This invention also provides a method for inhibiting the activity of an A3 adenosine receptor in a cell, which comprises contacting said cell with a compound of formula XI or compound 1720, 1721, 1722, 1723, 1724, 1725, 1726, 1727, 1728, 1729, 1730, 1731, 1732, 1733, 1734 or 1735.

In a further embodiment the invention provides a method for inhibiting the activity of an A3 adenosine receptor in a cell, which comprises contacting the cell with a compound of formula XI, preferably compound 1735, or compound 1720, 1721, 1722, 1723, 1724, 1725, 1726, 1727, 1728, 1729, 1730, 1731, 1732, 1733 or 1734.

In one embodiment of the method, the compound is an antagonist of said A3 adenosine receptor.

This invention also provides a method for inhibiting the activity of an $A_1$ adenosine receptor in a cell, which comprises contacting the cell with compound 1631.

In a further embodiment the invention provides the above method for inhibiting the activity of an $A_1$ adenosine receptor in a cell, wherein the compound is an antagonist of the $A_1$ adenosine receptor.

In another embodiment of the method, the cell is a human cell.

This invention also provides a method for treating a gastrointestinal disorder in an subject, comprising administering to the an effective amount of a compound of formula XI or compound 1720, 1721, 1722, 1723, 1724, 1725, 1726, 1727, 1728, 1729, 1730, 1731, 1732, 1733, 1734 or 1735.

In one embodiment of the method, said disorder is diarrhea.

In another embodiment of the method, the subject is a human.

In another embodiment of the method, the compound is an antagonist of A3 adenosine receptors.

This invention further provides a method for treating respiratory disorder in a subject, comprising administering to the subject an effective amount of a compound of formula XI, or compound 1720, 1721, 1722, 1723, 1724, 1725, 1726, 1727, 1728, 1729, 1730, 1731, 1732, 1733, 1734 or 1735.

In one embodiment of the method, said disorder is asthma, chronic obstructive pulmonary disease, allergic rhinitis, or an upper respiratory disorder.

In another embodiment of the method, the subject is a human.

In another embodiment of the method, said compound is an antagonist of A3 adenosine receptors.

This invention also provides a method for treating damage to the eye of a subject which comprises administering to said subject an effective amount of a compound of formula XI or compound 1720, 1721, 1722, 1723, 1724, 1725, 1726, 1727, 1728, 1729, 1730, 1731, 1732, 1733, 1734 or 1735.

In one embodiment of the method, said damage comprises retinal or optic nerve head damage.

In another embodiment of the method, said damage is acute or chronic.

In another embodiment of the method, said damage is the result of glaucoma, edema, ischemia, hypoxia or trauma.

In another embodiment of the method, the subject is a human.

In another embodiment of the method, the compound is an antagonist of A3 adenosine receptors.

In a further embodiment the invention provides a method for treating a disease associated with an $A_1$ adenosine receptor in a subject, wherein said disease is asthma, chronic obstructive pulmonary disease, allergic rhinitis, or an upper respiratory disorder.

In a further embodiment the invention provides a method for treating a disease associated with $A_1$ adenosine receptor in a subject, wherein said disease is asthma, chronic obstructive pulmonary disease, allergic rhinitis, or an upper respiratory disorder and wherein the subject is a human.

In a further embodiment the invention provides a method for treating the above disease, wherein said compound is an antagonist of $A_1$ adenosine receptors.

In a further embodiment the invention provides a combination therapy for asthma, comprising compound 1631, and a steroid, β2 agonist, glucocorticoid, leukotriene antagonist, or anticolinergic agonist.

In a further embodiment the invention provides a pharmaceutical composition comprising a therapeutically effective amount of compound 1631, and a pharmaceutically acceptable carrier.

In a further embodiment the invention provides a method for treating a respiratory disorder by administering a therapeutically effective amount of compound 1631, wherein said respiratory disorder is asthma, allergic rhinitis, or chronic obstructive pulmonary disease.

In a further embodiment the invention provides a pharmaceutically acceptable salt compound 1631.

In yet a further embodiment the invention provides a method for treating a disease associated with A1 adenosine receptor in a subject, wherein the A1 adenosine receptor is associated with congestive heart failure.

This invention also provide a pharmaceutical composition comprising a therapeutically effective amount of a compound of formula XI or compound 1720, 1721, 1722, 1723, 1724, 1725, 1726, 1727, 1728, 1729, 1730, 1731, 1732, 1733, 1734 or 1735 and a pharmaceutically acceptable carrier.

In one embodiment of the pharmaceutical composition, said therapeutically effective amount is effective to treat a respiratory disorder or a gastrointestinal disorder.

In another embodiment of the pharmaceutical composition, said gastrointestinal disorder is diarrhea.

In another embodiment of the pharmaceutical composition, said respiratory disorder is asthma, allergic rhinitis, or chronic obstructive pulmonary disease.

In another embodiment of the pharmaceutical composition, said pharmaceutical composition is an ophthalmic formulation.

In another embodiment of the pharmaceutical composition, said pharmaceutical composition is an periocular, retrobulbar or intraocular injection formulation.

In another embodiment of the pharmaceutical composition, said pharmaceutical composition is a systemic formulation.

In another embodiment of the pharmaceutical composition, said pharmaceutical composition is a surgical irrigating solution.

As used herein, "A compound is $A_3$ selective." means that a compound has a binding constant to adenosine A3 receptor of at least ten times higher than that to adenosine $A_1$, $A_{2a}$, or $A_{2b}$.

A skilled artisan will know that metabolism of the compounds disclosed herein in a subject produces certain biologically active metabolites which can serve as drugs.

In a further embodiment the invention provides a therapy for glaucoma, comprising administering to a subject a therapeutically effective amount of a compound of formula XI, preferably compound 1735 or compound 1720, 1721, 1722, 1723, 1724, 1725, 1726, 1727, 1728, 1729, 1730, 1731, 1732, 1733, or 1734.

In a further embodiment the invention provides a therapy for glaucoma comprising one or more adenosine receptor antagonists, preferably comprising an adenosine receptor A3 antagonist (preferably a compound of formula XI, most preferably compound 1735 or 1720, 1721, 1722, 1723, 1724, 1725, 1726, 1727, 1728, 1729, 1730, 1731, 1732, 1733, or 1734).

In an alternative embodiment the invention provides a combination therapy for glaucoma comprising an adenosine receptor A3 antagonist (preferably a compound of formula XI, most preferably compound 1735 or compound 1720, 1721, 1722, 1723, 1724, 1725, 1726, 1727, 1728, 1729, 1730, 1731, 1732, 1733, or 1734), and one or more other compounds selected from the group consisting of beta adrenoceptor antagonists (i.e. beta adrenergic antagonists or beta-blockers) (e.g. timolol maleate, betaxolol, carteolol, levobunolol, metipranolol, L-653328 (the acetate ester of L-652698), beta 1 adrenoceptor antagonists), alpha-2 adrenoceptor agonists (e.g. aplaclonidine, brimonidine, AGN-195795, AGN-190837 (an analog of Bay-a-6781)), carbonic anhydrase inhibitors (brinzolamide, dorzolamide, MK-927 (an inhibitor of the human carbonic anhydrase II isoenzyme), inhibitors of carbonic anhydrase IV isoenzyme), cholinergic agonists (e.g. muscarinic cholinergic agonists, carbachol, pilocarpine HCl, pilocarpine nitrate, pilocarpine, pilocarpine prodrugs (e.g. DD-22A)), prostaglandins and prostaglandin receptor agonists (e.g. latanoprost, unoprostone isopropyl, PGF2 alpha agonists, prostanoid-selective FP receptor agonists, PG agonists such as the hypotensive prostamides), angiotensin converting enzyme (ACE) inhibitors (e.g. Spirapril, spiraprilat), AMPA receptor antagonists, 5-HT agonists (e.g. a selective 5-HT 1A receptor agonist such as MKC-242 (5-3-[((2S)-1,4-benzodioxan-2-ylmethyl)amino]propoxy-1, 3-benxodioxole HCl), angiogenesis inhibitors (e.g. the steroid anecortave), NMDA antagonists (e.g. HU-211, memantine, the cannabinoid NMDA-receptor agonist dexanabinol, prodrugs and analogs of dexanabinol, NR2B-selective antagonists (e.g. eliprodil (SL-82.0715)), renin inhibitors (e.g. CGP-38560, SR-43845), cannabinoid receptor agonists (e.g. tetrahydrocannabinol (THC) and THC analogs, selective CB2 cannabinoid receptor agonists (e.g. L-768242, L-759787), compounds such as anandamide that bind to both brain-specific CB1 receptors and peripheral CB2 receptors), angiotensin receptor antagonists (e.g., angiotensin II receptor antagonists (e.g. CS-088), selective angiotensin II AT-I receptor antagonists, such as losartan potassium), hydrochlorothiazide (HCTZ), somatostatin agonists (e.g. the non-peptide somatostatin agonist NNC-26-9100), glucocorticoid antagonists, mast cell degranulation inhibitors (e.g. nedocromil), alpha-adrenergic receptor blockers (e.g. dapiprazole, alpha-2 adrenoceptor antagonists, alpha 1 adrenoceptor antagonists (e.g. bunazosin)), alpha-2 adrenoceptor antagonists, thromboxane A2 mimetics, protein kinase inhibitors (e.g. H7), prostaglandin F derivatives (e.g. S-1033), prostaglandin-2 alpha antagonists (e.g. PhXA-34), dopamine D1 and 5-HT2 agonists (fenoldopam), nitric-oxide-releasing agents (e.g. NCX-904 or NCX-905, nitric-oxide-releasing derivatives of timolol), 5-HT 2 antagonists (e.g. sarpogrelate), NMDA antagonists (e.g. prodrugs and analogs of dexanabinol), alpha 1 adrenoceptor antagonists (e.g. bunazosin), cyclooxygenase inhibitors (e.g. diclofenac, or the non-steroidal compound nepafenac), inosine, dopamine D2 receptor and alpha 2 adrenoceptor agonists (e.g. talipexole), dopamine D1 receptor antagonist and D2 receptor agonists (e.g. SDZ-GLC-756), vasopressin receptor antagonists (e.g. vasopressin V2 receptor antagonists (e.g. SR-121463)), endothelin antagonists (e.g. TBC-2576), 1-(3-hydroxy-2-phosphonylmethoxypropyl) cytosine (HPMPC) and related analogs and prodrugs, thyroid hormone receptor ligands (e.g. KB-130015), muscarinic M1 agonists, NMDA-receptor antagonists (e.g. the cannabinoid NMDA-receptor antagonist dexanabinol), PG agonists such as the hypotensive lipids, prostamides, sodium channel blockers, NMDA antagonists, mixed-action ion channel blockers, beta adrenoceptor antagonist and PGF2 alpha agonist combinations (e.g. latanoprost and timolol), guanylate cyclase activators (e.g. atrial natriuretic peptide (ANP) or non-peptide mimetics, inhibitors of ANP neutral endopeptidase, nitrovasodilators (e.g. nitroglycerin, hydralazine, sodium nitroprusside), endothelin receptor modulators (e.g. ET-1 or non-peptide mimetics, sarafotoxin-S6c), ethacrynic acid, other phenoxyacetic acid analogs (e.g. indacrinone, ticrynafen), actin disrupters (e.g. latrunculin), calcium channel blockers (e.g. verapamil, nifedipine, brovincamine, nivaldipine) and neuroprotective agents.

A combination therapy for glaucoma, comprising a compound of formula XI, preferably compound 1735, or compound 1720, 1721, 1722, 1723, 1724, 1725, 1726, 1727, 1728, 1729, 1730, 1731, 1732, 1733, or 1734, and one or more compounds selected from the group consisting of beta adrenoceptor antagonists, alpha-2 adrenoceptor agonists, carbonic anhydrase inhibitors, cholinergic agonists and prostaglandin receptor agonists.

In a further embodiment the invention provides a method of making a composition which comprises a compound of formula XI, preferably compound 1735, or compound 1720, 1721, 1722, 1723, 1724, 1725, 1726, 1727, 1728, 1729, 1730, 1731, 1732, 1733, or 1734, the method comprising admixing a compound of formula XI, preferably compound 1735, or compound 1720, 1721, 1722, 1723, 1724, 1725, 1726, 1727, 1728, 1729, 1730, 1731, 1732, 1733, or 1734, with a suitable carrier.

In a further embodiment the invention provides a pharmaceutically acceptable salt of a compound of formula XI, preferably compound 1735, or compound 1720, 1721, 1722, 1723, 1724, 1725, 1726, 1727, 1728, 1729, 1730, 1731, 1732, 1733, or 1734.

In a further embodiment the invention provides a pharmaceutically acceptable salt of a compound of formula XI, preferably compound 1735, or compound 1720, 1721, 1722, 1723, 1724, 1725, 1726, 1727, 1728, 1729, 1730, 1731, 1732, 1733, or 1734, wherein the pharmaceutically acceptable salt contains an anion selected from the group consisting of maleic, fumaric, tartaric, acetate, phosphate and mesylate.

The deazapurines of the invention can be prepared using standard methods for organic synthesis. Deazapurines can be purified by reverse phase HPLC, chromatography, recrystallization, etc. and their structures confirmed by mass spectral analysis, elemental analysis, IR and/or NMR spectroscopy.

Typically, synthesis of the intermediates as well as the deazapurines of the invention is performed in solution. The addition and removal of one or more protecting group is also typical practice and is known to those skilled in the art.

Additional synthetic schemes and binding data for compounds specific to adenosine A1 and A3 receptors are disclosed in PCT International Publication Nos. WO 99/62518 and WO 01/39777 A1 and are hereby incorporated herein in their entireties.

The invention is further illustrated by the following examples which in no way should be construed as being further limiting. The contents of all references, pending patent applications and published patent applications, cited throughout this application, including those referenced in the background section, are hereby incorporated by reference. It should be understood that the models used throughout the examples are accepted models and that the demonstration of efficacy in these models is predictive of efficacy in humans.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

The deazapurines of the invention can be prepared using standard methods for organic synthesis. Deazapurines can be purified by reverse phase HPLC, chromatography, recrystallization, etc. and their structures confirmed by mass spectral analysis, elemental analysis, IR and/or NMR spectroscopy.

Typically, synthesis of the intermediates as well as the deazapurines of the invention is performed in solution. The addition and removal of one or more protecting group is also typical practice and is known to those skilled in the art. Typical synthetic schemes for the preparation of deazapurine intermediates of the invention are outlined below in Scheme I.

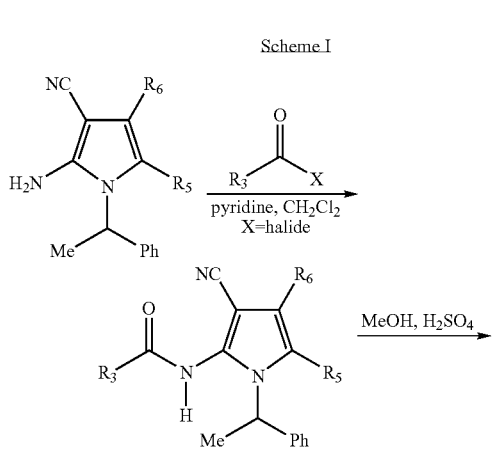

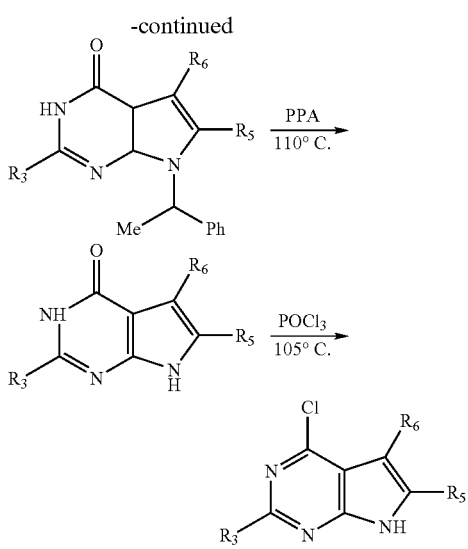

wherein R₃, R₅ and R₆ are as defined above.

In general, a protected 2-amino-3-cyano-pyrrole can be treated with an acyl halide to form a carboxyamido-3-cyano-pyrrole which can be treated with acidic methanol to effect ring closure to a pyrrolo[2,3d]pyrimidine-4(3H)-one (Muller, C. E. et al. J. Med. Chem. 40:4396 (1997)). Removal of the pyrrolo protecting group followed by treatment with a chlorinating reagent, e.g., phosphorous oxychloride, produced substituted or unsubstituted 4-chloro-7H-pyrrolo[2,3d]pyrimidines. Treatment of the chloropyrimidine with amines afforded 7-deazapurines.

For example, as shown in Scheme I, a N-(1-dl-phenylethyl)-2-amino-3-cyano-pyrrole was treated with an acyl halide in pyridine and dichloromethane. The resultant N-(1-dl-phenylethyl)-2-phenylcarboxyamido-3-cyano-pyrrole was treated with a 10:1 mixture of methanol/sulfuric acid to effect ring closure, resulting in a dl-7H-7-(1-phenylethyl) pyrrolo[2,3d]pyrimidine-4(3H)-one. Removal of the phenylethyl group by treatment of the pyrimidine with polyphosphoric acid (PPA) followed by POCl₃ afforded a key intermediate, the 4-chloro-7H-pyrrolo[2,3d]pyrimidine. Further treatment of the 4-chloro-7H-pyrrolo[2,3d]pyrimidine with various amines listed in Table 1 gives compounds of formula (I) and (II).

TABLE 1

| R | M⁺ + H | R | M⁺ + H |
|---|---|---|---|
| | 343.2 | | 351.27 |
| | 343.18 | | 430.35 |
| | 337.21 | | 359.44 |
| | 364.19 | | 404.32 |
| | 330.18 | | 330.45 |

TABLE 1-continued

| R | M+ + H | R | M+ + H |
|---|---|---|---|
| (imidazole-propyl-NH) | 347.22 | (NH-CH(CH2OH)-CH2-iPr) | 339.47 |
| (piperidine-ethyl-NH) | 350.28 | (NH-CH2CH2-C(O)OEt) | 353.41 |
| (2-pyridyl-ethyl-NH) | 344.19 | (NH-CH2CH2-NHAc) | 324.45 |
| (4-(N-CO2Et)piperidinyl-NH) | 394.16 | (NH-CH2CH2-OPh) | 359.38 |
| (indanol-NH) | 371.12 | (NH-CH2CH2-N-methylpiperazine) | 379.40 |
| (NH-CH(Ph)-CH2OH) | 359.39 | (benzodioxane-CH2-NH) | 387.41 |
| (NH-CH(CH2OMe)-CH(OH)Ph) | 403.33 | (3-pyridyl-ethyl-NH) | 344.48 |
| (2-hydroxycyclohexyl-NH) | 351.49 | (2-hydroxycyclohexyl-NH) | 337.53 |
| (3-pyridyl-CH2-NH) | 330.37 | (NH-iBu) | 295.2 |

TABLE 1-continued
| R | M⁺ + H | R | M⁺ + H |
|---|---|---|---|
| 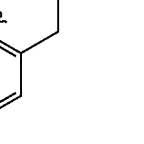 | 407.23 | 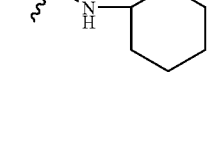 | 321.2 |
| 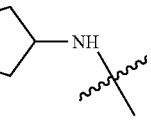 | 355.45 | 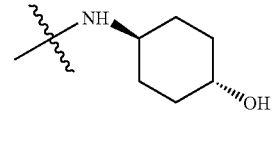 | 337.53 |
| 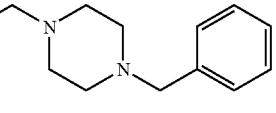 | 441.33 | 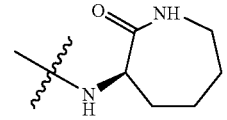 | 350.2 |
| 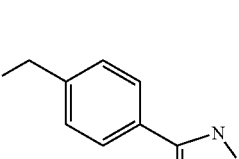 | 413.24 | 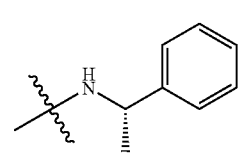 | 343.2 |
|  | 372.48 | 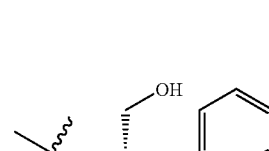 | 373.2 |
|  |  | 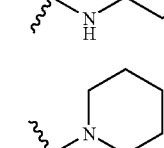 | 307.2 |
A general approach to prepare 6-substituted pyrroles is depicted in the following scheme (Scheme II).
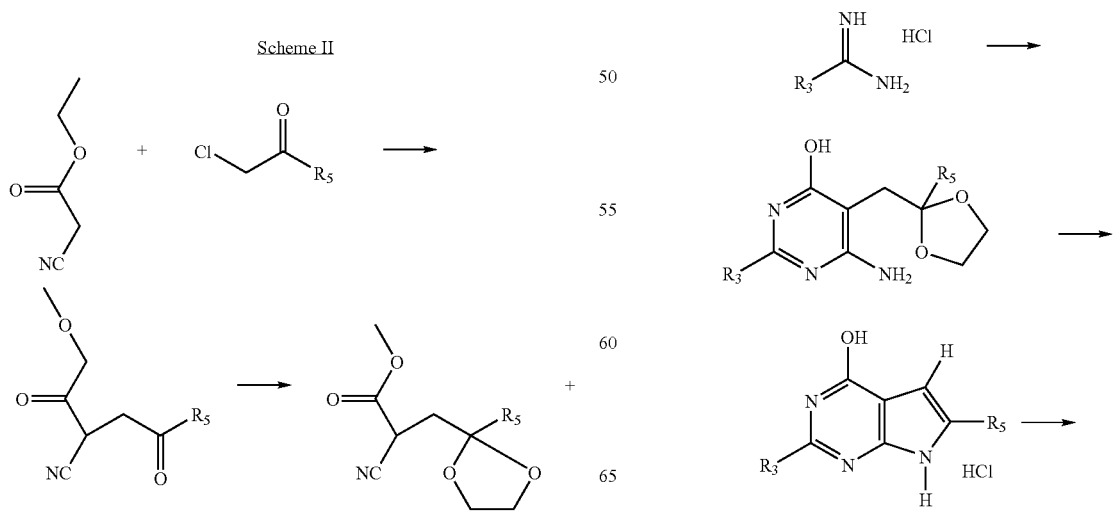
Scheme II

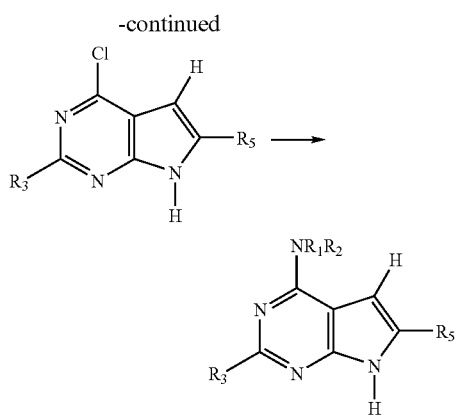

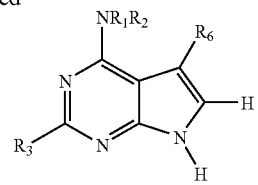

wherein $R_1$ through $R_6$ are defined as above and R is a removable protecting group.

Condensation of malononitrile and an excess of a ketone followed by bromination of the product afforded a mixture of starting material, monobrominated and dibrominated products which were treated with an alkylamine, arylamine or alkylarylamine. The resultant amine product was acylated with an acid chloride and the monacylated pyrrole was cyclized in the presence of acid to afford the corresponding pyrimidine. The pyrrole protecting group was removed with polyphosphoric acid and treated with phosphorous oxychloride to produce a chlorinated product. The chlorinated pyrrole could subsequently be treated with an amine to produce an amino 5-substituted pyrrole. Alkylation of the pyrrole nitrogen can be achieved under art recognized conditions.

Schemes IV and V depict methods for preparing the deazapurines 1 and 2 of the invention.

wherein $R_1$ through $R_5$ are as defined above.

Transesterification and alkylation of ethyl cyanoacetate with an α-haloketone affords a ketomethylester. Protection of the ketone followed by treatment with an amidine (e.g., alkyl, aryl or alkylaryl) hydrochloride produced the resultant ketal protected pyrimidine. Removal of the protecting group, followed by cyclization and treatment with phosphorous oxychloride afforded the chloride intermediate which could be further treated with an amine to afford an amine 6-substituted pyrrole. Additionally, alkylation of the pyrrole nitrogen can be achieved under art recognized conditions.

A general approach to prepare 5-substituted pyrroles is depicted in the following scheme (Scheme III).

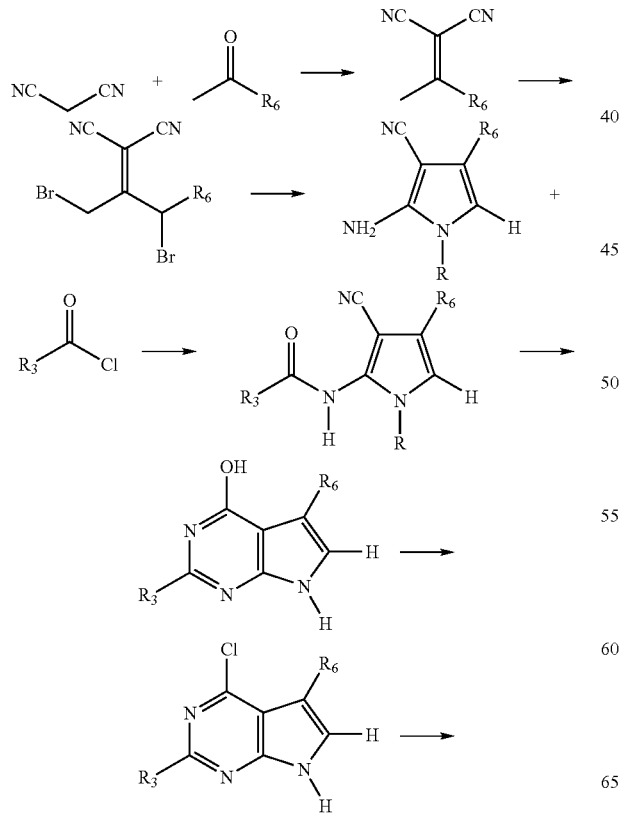

Scheme III

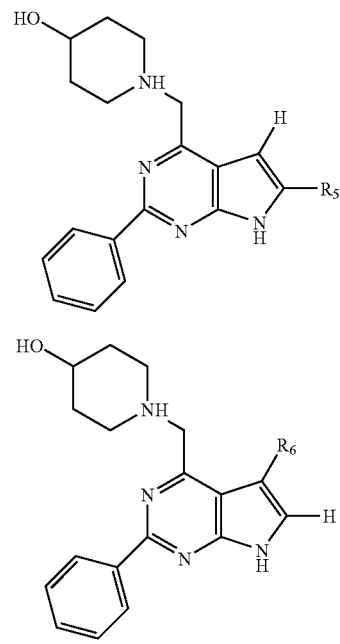

wherein $R_5$ and $R_6$ are as described above, e.g., $CH_3$.

Specific Preparation of 6-methyl pyrrolopyrimidines

The key reaction toward 6-methylpyrrolopyrimidines (1) [$R_5$=$CH_3$] was cyclization of a cyanoacetate with benzamidine to a pyrimidine. It was believed methyl cyanoacetate would cyclize more efficiently with benzamidine to a pyrimidine than the corresponding ethyl ester. Therefore, transesterification and alkylation of ethyl cyanoacetate in the presence of NaOMe and an excess of an α-haloacetyl moiety, e.g., chloroacetone, gave the desired methyl ester (3) in 79% yield (Scheme IV). The ketoester (3) was protected as the acetal (4) in 81% yield. A new cyclization method to the pyrimidine (5) was achieved with an amidine hydrochloride, e.g., benzamidine hydrochloride, with 2 equivalents of DBU to afford the 5 in 54% isolated yield. This method improves the yield from 20% using the published conditions, which utilizes NaOMe during the cyclization with guanidine. Cyclization to the pyrrole-pyrimidine (6) was achieved via deprotection of the acetal in aqueous HCl in 78% yield. Reaction of (6) with phosphorous oxychloride at reflux gave the corresponding 4-chloro derivative (7). Coupling with trans-4-aminocyclohexanol in dimethyl sulfoxide at 135° C., gave (1) in 57% from (7). One skilled in the art will appreciate that choice of reagents allows for great flexibility in choosing the desired substituent $R_5$.

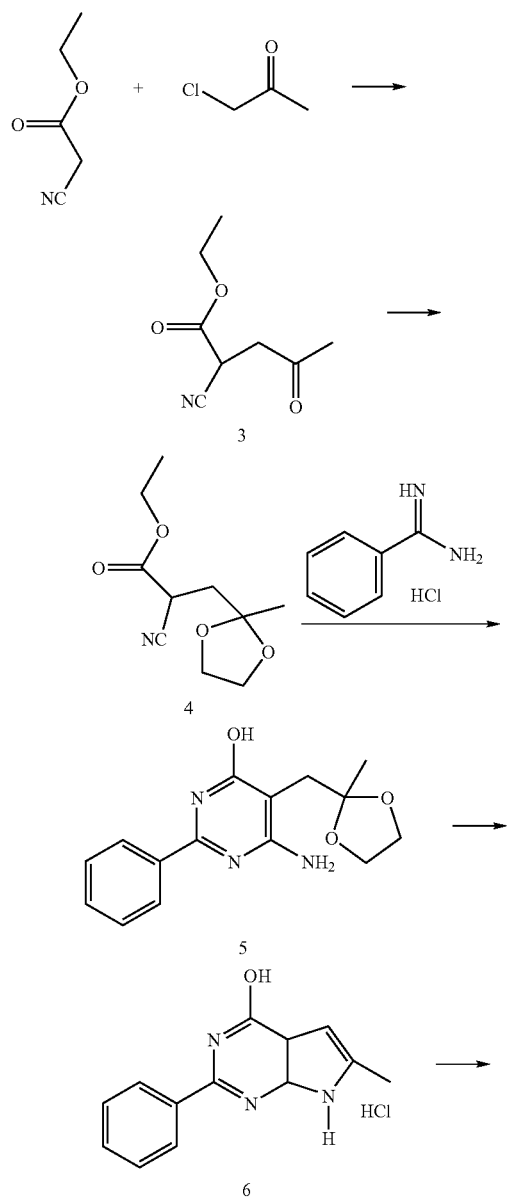

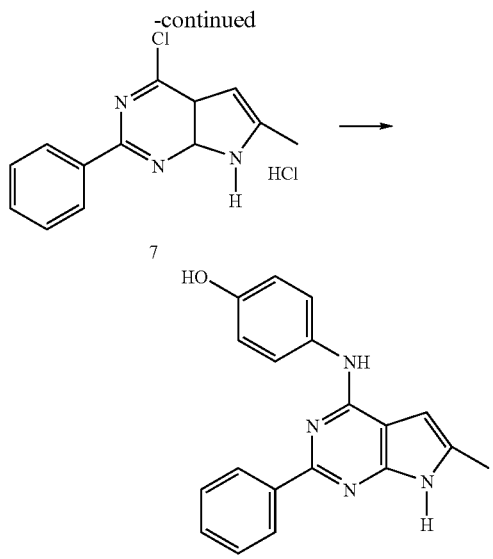

Specific Preparation of 5-methylpyrrolopyrimidines

Knoevengel condensation of malononitrile and an excess ketone, e.g., acetone in refluxing benzene gave 8 in 50% yield after distillation. Bromination of 8 with N-bromosuccinimde in the presence of benzoyl peroxide in chloroform yielded a mixture of starting material, mono- (9), and di-brominated products (5/90/5) after distillation (70%). The mixture was reacted with an α-methylalkylamine or α-methylarylamine, e.g., α-methylbenzylamine, to deliver the aminopyrrole (10). After passing through a short silica gel column, the partially purified amine (31% yield) was acylated with an acid chloride, e.g., benzoyl chloride to deliver mono- (11), and diacylated (12) pyrroles, which were separated by flash chromatography. Acid hydrolysis of the disubstituted pyrrole (12) generated a combined yield of 29% for the acylpyrrole (11). Cyclization in the presence of concentrated sulphuric acid and DMF yielded (13) (23%), which was deprotected with polyphosphoric acid to (14). Reaction of (14) with phosphorous oxychloride at reflux gave the corresponding 4-chloro derivative (15). Coupling with trans-4-aminocyclohexanol in dimethyl sulfoxide at 135° C. gave (2) [$R_6$=CH_3] in 30% from (14) (See Scheme V). One skilled in the art will appreciate that choice of reagents allows for great flexibility in choosing the desired substituent $R_6$.

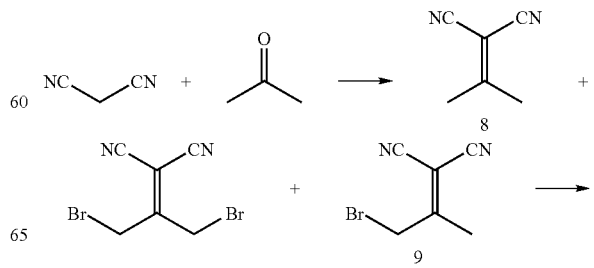

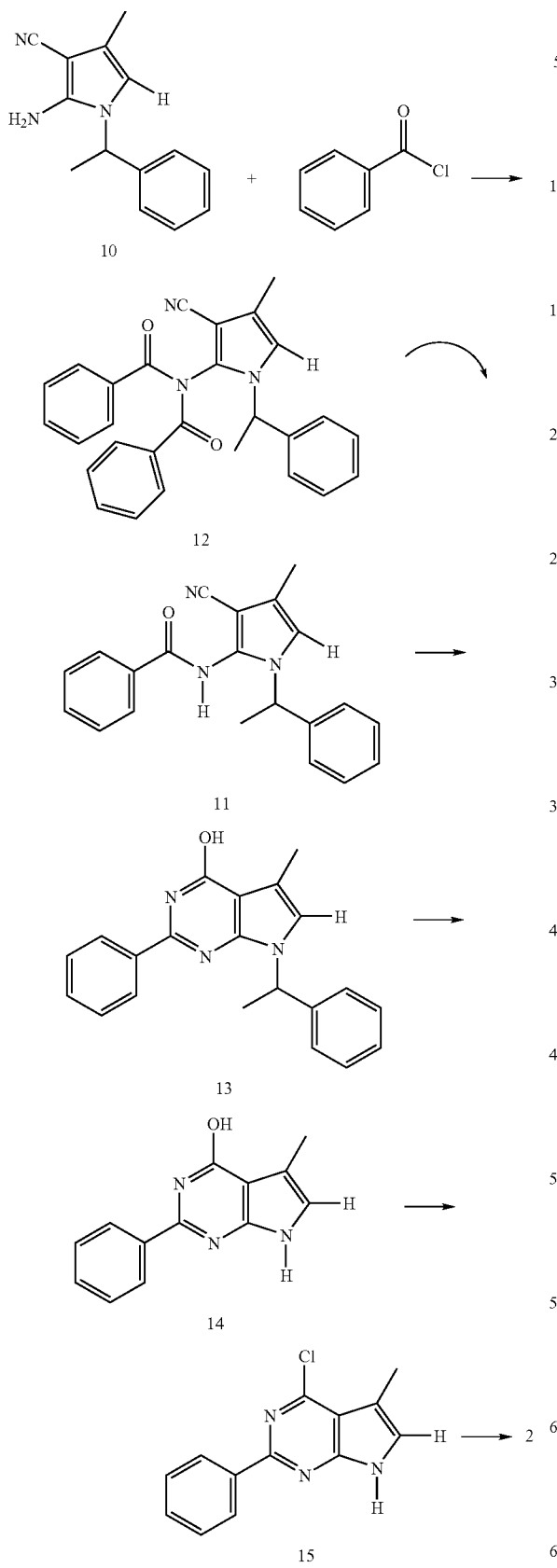

Alternative Synthetic Route to $R_6$-Substituted Pyrroles. e.g., 5-methyl pyrrolopyrimidines This alternative route to $R_6$-substituted pyrroles, e.g., 5-methylpyrrolopyrimidines, involves transesterification and alkylation of ethyl cyanoacetate to (16) (Scheme VI). The condensation of (16) with benzamidine hydrochloride with 2 equivalents of DBU affords the pyrimidine (17). Cyclization to the pyrrole-pyrimidine (14) will be achieved via deprotection of the acetal in aqueous HCl. Reaction of (14) with phosphorous oxychloride at reflux gave the corresponding 4-chloro derivative (15). Coupling with trans-4-aminocyclohexanol in dimethyl sulfoxide at 135° C. gives 2. This procedure reduces the number of synthetic reactions to the target compound (2) from 9 to 4 steps. Moreover, the yield is dramatically improved. Again, one skilled in the art will appreciate that choice of reagents allows for great flexibility in choosing the desired substituent $R_6$.

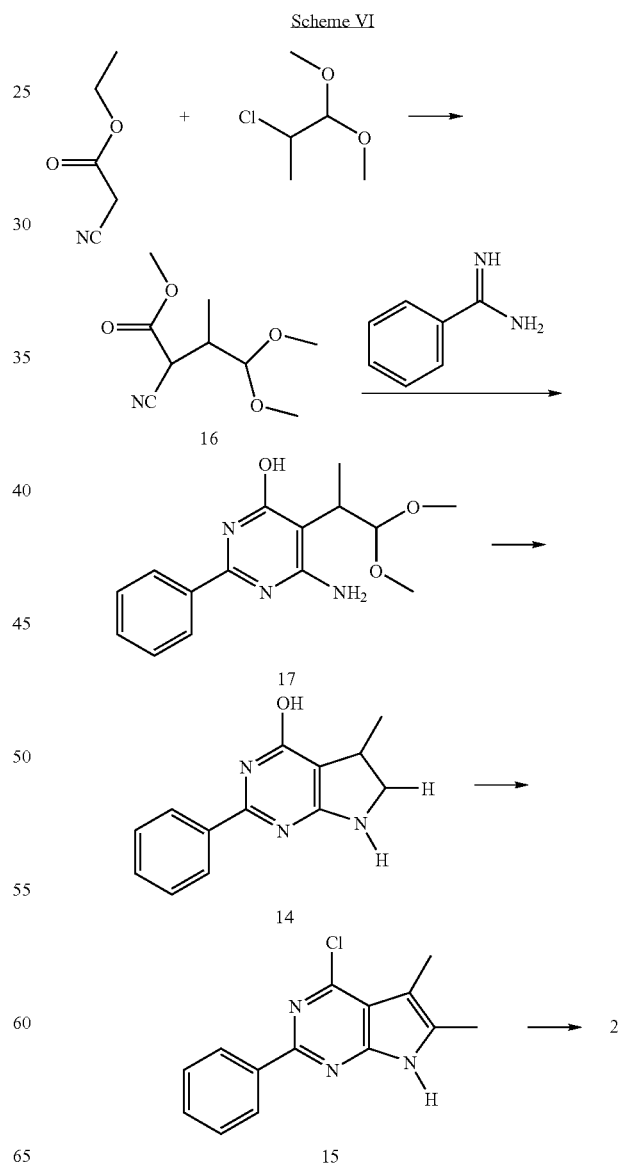

A general approach to prepare des-methyl pyrrole is depicted in the following scheme (Scheme VII)

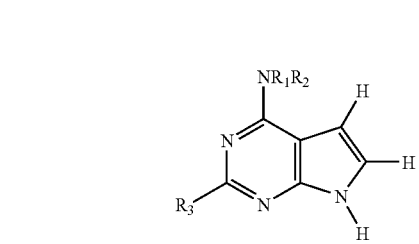

Scheme VII

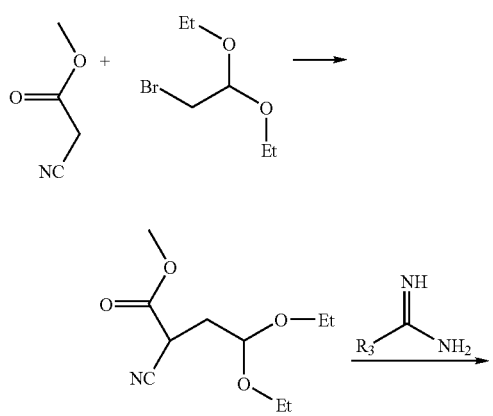

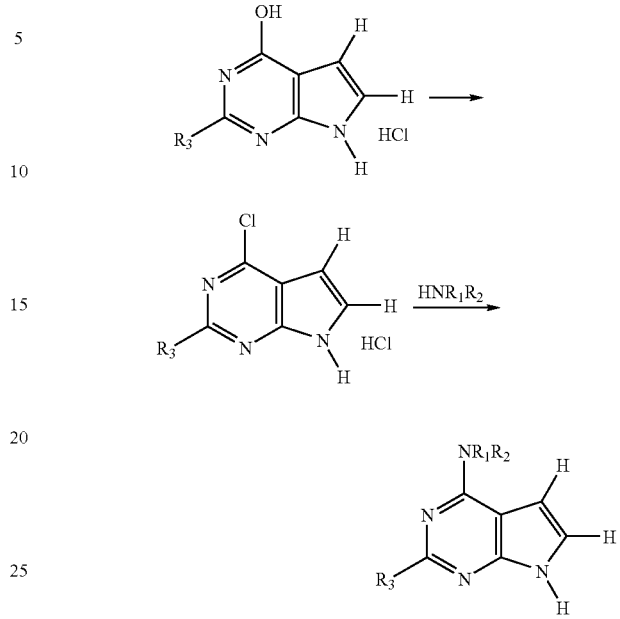

wherein $R_1$ through $R_3$ are defined as above.

Alkylation of an alkyl cyanoacetate with a diethyl acetal in the presence of a base afforded a cyano diethyl acetal which was treated with an amidine salt to produce a methyl pyrrolopyrimidine precursor. The precursor was chlorinated and treated with an amine to form the des-methyl pyrrolopyrimidine target as shown above.

For example, Scheme VIII depicts the synthesis of compound (18).

Scheme VIII

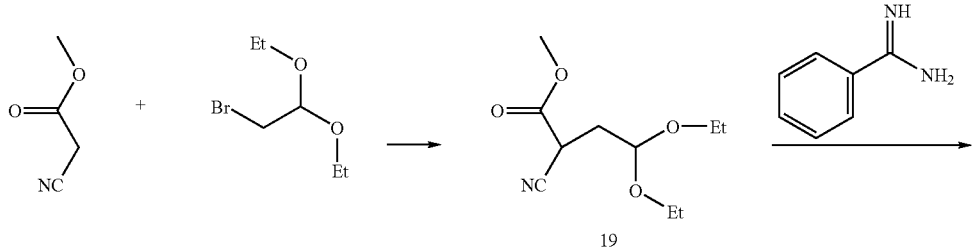

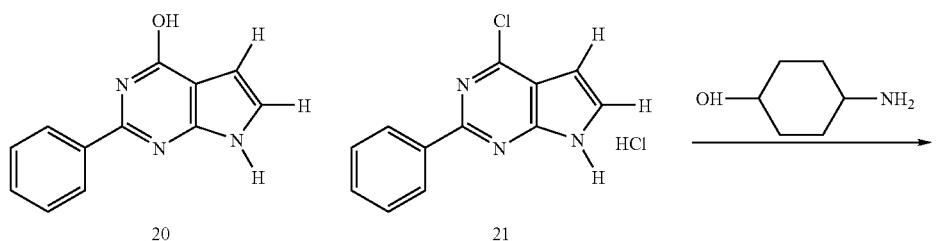

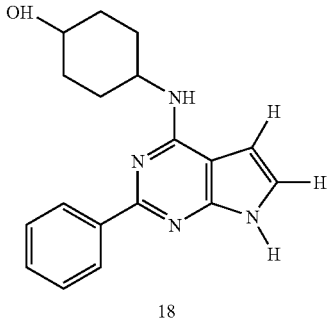

18

Commercially available methyl cyanoacetate was alkylated with bromoacetaldehyde diethyl acetal in the presence of potassium carbonate and NaI to yield (19). Cyclization to the pyrimidine (20) was achieved in two steps. Initially, the pyrimidine-acetal was formed via reaction of (19) with benzamidine hydrochloride with 2 equivalents of DBU. The resultant pyrimidine-acetal was deprotected without purification with aqueous 1 N HCl and the resultant aldehyde cyclized to the pyrrolo-pyrimidine (20), which was isolated by filtration. Reaction of (20) with phosphorous oxychloride at reflux afforded the corresponding 4-chloro derivative (21). Coupling of the chloro derivative with trans-4-aminocyclohexanol in DMSO at 135° C. gave compound (18) from compound (21).

Schemes II-VIII demonstrate that it is possible to functionalize the 5- and 6-position of the pyrrolopyrimidine ring. Through the use of different starting reagents and slight modifications of the above reaction schemes, various functional groups can be introduced at the 5- and 6-positions in formula (I) and (II). Table 2 illustrates some examples.

TABLE 2

Selected list of 5- and 6-substituted pyrrolopyrimidines.

| Starting Reagent | $R_5$ | $R_6$ |
|---|---|---|
| (chloroacetaldehyde dimethyl acetal) | H | |
| (α-chloro-4-R$_3$-acetophenone) | H | Substituted Ar |
| (methyl acetoacetate) | H | $CH_2C(O)OCH_3$ |
| (methyl 2-chloroacetoacetate) | $C(O)OCH_3$ | $CH_3$ |

TABLE 2-continued

Selected list of 5- and 6-substituted pyrrolopyrimidines.

| Starting Reagent | $R_5$ | $R_6$ |
|---|---|---|
| (methyl 2-chloro-N-methylacetoacetamide) | $C(O)NHCH_3$ | $CH_3$ |

The invention is further illustrated by the following examples which in no way should be construed as being further limiting. The contents of all references, pending patent applications and published patent applications, cited throughout this application, including those referenced in the background section, are hereby incorporated by reference. It should be understood that the models used throughout the examples are accepted models and that the demonstration of efficacy in these models is predictive of efficacy in humans.

Exemplification

Preparation 1

A modification of the alkylation method of Seela and Lüpke was used.[1] To an ice-cooled (0° C.) solution of ethyl cyanoacetate (6.58 g, 58.1 mmol) in MeOH (20 mL) was slowly added a solution of NaOMe (25% w/v; 58.1 mmol). After 10 min, chloroacetone (5 mL; 62.8 mmol) was slowly added. After 4 h, the solvent was removed. The brown oil was diluted the EtOAc (100 mL) and washed with $H_2O$ (100 mL). The organic fraction was dried, filtered, and concentrated to a brown oil (7.79 g; 79%). The oil (3) (Scheme IV) was a mixture of methyl/ethyl ester products (9/1), and was used without further purification. $^1$H NMR (200 MHz, CDCl$_3$) δ 4.24 (q, J=7.2 Hz, OCH$_2$), 3.91 (dd, 1H, J=7.2, 7.0 Hz, CH), 3.62 (s, 3H, OCH$_3$), 3.42 (dd, 1H, J=15.0, 7.1 Hz, 1×CH$_2$); 3.02 (dd, 1H, J=15.0, 7.0 Hz, 1×CH$_2$); 2.44 (s, 3H, CH$_3$), 1.26 (t, J=7.1 Hz, ester-CH$_3$).

[1] Seela, F.; Lüpke, U. Chem. Ber. 1977, 110, 1462-1469.

Preparation 2

The procedure of Seela and Lüpke was used.[1] Thus, protection of the ketone (3) (Scheme IV; 5.0 g, 32.2 mmol) with ethylene glycol (4 mL, 64.4 mmol) in the presence of TsOH (100 mg) afforded (4) as an oil (Scheme IV; 5.2 g, 81.0) after flash chromatography (SiO$_2$; 3/7 EtOAc/Hex, R$_f$ 0.35). Still contains ~5% ethyl ester: $^1$H NMR (200 MHz, CDCl$_3$) δ 4.24 (q, J=7.2 Hz, OCH$_2$), 3.98 (s, 4H, 2×acetal-CH$_2$), 3.79 (s, 3H, OCH$_3$), 3.62 (dd, 1H, J=7.2, 7.0 Hz, CH), 2.48 (dd, 1H, J=15.0, 7.1 Hz, 1×CH$_2$), 2.32 (dd, 1H, J=15.0, 7.0 Hz, 1×CH$_2$); 1.35 (s, 3H, CH$_3$), 1.26 (t, J=7.1 Hz, ester-CH$_3$); MS (ES): 200.1 (M$^+$+1).

[1]Seela, F.; Lüpke, U. Chem. Ber. 1977, 110, 1462-1469.

Preparation 3

A solution of acetal (4) (Scheme IV, 1 g, 5.02 mmol), benzamidine (786 mg, 5.02 mmol), and DBU (1.5 mL, 10.04 mmol) in dry DMF (15 mL) was heated to 85° C. for 15 h. The mixture was diluted with CHCl$_3$ (30 mL) and washed with 0.5 N NaOH (10 mL) and H$_2$O (20 mL). The organic fraction was dried, filtered and concentrated to a brown oil. Flash chromatography (SiO$_2$; 1/9 EtOAc/CH2Cl2, R$_f$ 0.35) was attempted, but material crystallized on the column. The silica gel was washed with MeOH. Fractions containing the product (5) (Scheme IV) were concentrated and used without further purification (783 mg, 54.3%): $^1$H NMR (200 MHz, CDCl$_3$) δ 8.24 (m, 2H, Ar—H), 7.45 (m, 3H, Ar—H), 5.24 (br s, 2H, NH$_2$), 3.98 (s, 4H, 2×acetal-CH$_2$), 3.60-3.15 (m, 2H, CH$_2$), 1.38 (s, 3H, CH$_3$); MS (ES): 288.1 (M$^+$+1).

Preparation of compound (20) (Scheme VIII): A solution of acetal (19) (4.43 g, 20.6 mmol)[1], benzamine hydrochloride (3.22 g, 20.6 mmol), and DBU (6.15 mL, 41.2 mmol) in dry DMF (20 mL) was heated to 85° C. for fifteen hours. The mixture was diluted with 100 mL of CHCl$_3$, and washed with H$_2$O (2×50 mL). The organic fraction was dried, filtered, and concentrated to a dark brown oil. The dark brown oil was stirred in 1N HCl (100 mL) for 2 hours at room temperature. The resulting slurry was filtered yielding the HCl salt of (20) as a tan solid (3.60 g, 70.6%); $^1$H NMR (200 MHz, DMSO-d6) 11.92 (s 1H), 8.05 (m, 2H, Ar—H), 7.45 (m, 3H, Ar—H), 7.05 (s, 1H, pyrrole-H); MS(ES): 212.1 (M$^+$+1).

Preparation 4

A solution of acetal (5) (700 mg, 2.44 mmol) in 1 N HCl (40 mL) was stirred for 2 h at RT. The resultant slurry was filtered yielding the HCl salt of 2-phenyl-6-methyl-7H-pyrrolo[2,3d]pyrimidin-4(3H)-one as a tan solid (498 mg, 78.0%): $^1$H NMR (200 MHz, DMSO-d$_6$) δ 11.78 (s, 1H), 8.05 (m, 2H, Ar—H), 7.45 (m, 3H, Ar—H), 6.17 (s, 1H, pyrrole-H), 2.25 (s, 3H, CH$_3$); MS (ES): 226.1 (M$^+$+1).

Preparation 5

A modification of the Chen et al. cyclization method was used.[1] To an ice-cooled (0° C.) solution of bromide (9), (Scheme V; 20.0 g, 108 mmol; 90% pure) in isopropyl alcohol (60 mL) was slowly added a solution of α-methylbenzylamine (12.5 mL, 97.3 mmol). The black solution was allowed to warm to RT and stir for 15 h. The mixture was diluted with EtOAc (200 mL) and washed with 0.5 N NaOH (50 mL). The organic fraction was dried, filtered, and concentrated to a black tar (19.2 g; 94%). The residue was partially purified by flash chromatography (SiO$_2$; 4/96 MeOH/CH$_2$Cl$_2$, R$_f$ 0.35) to a black solid (6.38 g, 31%) as the compound dl-1-(1-phenylethyl)-2-amino-3-cyano-4-methylpyrrole: MS (ES): 226.1 (M$^+$+1).

[1]Chen, Y. L.; Mansbach, R. S.; Winter, S. M.; Brooks, E.; Collins, J.; Corman, M. L.; Dunaiskis, A. R.; Faraci, W. S.; Gallaschun, R. J.; Schmidt, A.; Schulz, D. W. J. Med. Chem. 1997, 40, 1749-1754.

Preparation 6

To a solution of dl-1-(1-phenylethyl)-2-amino-3-cyano-4,5-dimethylpyrrole[1] (14.9 g, 62.5 mmol) and pyridine (10.0 mL) in dichloromethane (50.0 mL) was added benzoyl chloride (9.37 g, 66.7 mmol) at 0° C. After stirring at 0° C. for 1 hr, hexane (10.0 mL) was added to help precipitation of product. Solvent was removed in vacuo and the solid was recrystallized from EtOH/H$_2$O to give 13.9 g (65%) of dl-1-(1-phenylethyl)-2-phenylcarbonylamino-3-cyano-4,5-dimethylpyrrole. mp 218-221° C.;

$^1$H NMR (200 MHz, CDCl$_3$) δ 1.72 (s, 3H), 1.76 (d, J=7.3 Hz, 3H), 1.98 (s, 3H), 5.52 (q, J=7.3 Hz, 1H), 7.14-7.54 (m, 9H), 7.68-7.72 (dd, J=1.4 Hz, 6.9 Hz, 2H), 10.73 (s, 1H); MS (ES): 344.4 (M$^+$+1).

1 Liebigs Ann. Chem. 1986, 1485-1505.

Preparation 7

To a solution of dl-1-(1-phenylethyl)-2-phenylcarboxyamido-3-cyano-4,5-dimethylpyrrole (1.0 g, 2.92 mmol) in methanol (10.0 mL) was added concentrated sulfuric acid (1.0 mL) at 0° C. The resulted mixture was refluxed for 15 hr and cooled down to room temperature. The precipitate was filtered to give 0.48 g (48%) of dl-5,6-dimethyl-2-phenyl-7H-7-(1-phenylethyl)pyrrolo[2,3d]pyrimidin-4(3H)-one. $^1$H NMR (200 MHz, CDCl$_3$) δ 2.02 (d, J=7.4 Hz, 3H), 2.04 (s, 3H), 2.41 (s, 3H), 6.25 (q, J=7.4 Hz, 1H), 7.22-7.50 (m, 9H), 8.07-8.12 (dd, J=3.4 Hz, 6.8 Hz, 2H), 10.51 (s, 1H); MS (ES): 344.2 (M$^+$+1).

Preparation 8

A solution of dl-1-(1-phenylethyl)-2-benzoylamino-3-cyano-4-dimethylpyrrole (785 mg, 2.38 mmol) with concentrated H$_2$SO$_4$ (1 mL) in DMF (13 mL) was stirred at 130° C. for 48 h. The black solution was diluted with CHCl$_3$ (100 mL) and washed with 1 N NaOH (30 mL), and brine (30 mL). The organic fraction was dried, filtered, concentrated, and purified by flash chromatography (SiO$_2$; 8/2 EtOAc/Hex, R$_f$ 0.35) to a brown solid (184 mg, 24%) as dl-5-methyl-2-phenyl-7H-7-(1-phenylethyl)pyrrolo[2,3d]pyrimidin-4(3H)-one. $^1$H NMR (200 MHz, CDCl$_3$) δ 8.18 (m, 2H, Ar—H), 7.62-7.44 (m, 3H, Ar—H), 7.40-7.18 (m, 5H, Ar—H), 6.48 (s, 1H, pyrrole-H), 6.28 (q, 1H, J=7.2 Hz, CH—CH$_3$), 2.18 (s, 3H, pyrrole-CH$_3$), 2.07 (d, 3H, J=7.2 Hz, CH—CH$_3$); MS (ES): 330.2 (M$^+$+1).

Preparation 9

A mixture of dl-1-(1-phenylethyl)-2-amino-3-cyano-4,5-dimethylpyrrole (9.60 g, 40.0 mmol) and of formic acid (50.0 mL, 98%) was refluxed for 5 hr. After cooling down to room temperature and scratching the sides of flask, copious precipitate was formed and filtered. The material was washed with water until washings showed neutral pH to give dl-5,6-dimethyl-7H-7-(1-phenylethyl)pyrrolo[2,3d]pyrimidin-4(3H)-one.

$^1$H NMR (200 MHz, CDCl$_3$) δ 1.96 (d, J=7.4 hz, 3H), 2.00 (s, 3H), 2.38 (s, 3H), 6.21 (q, J=7.4 Hz, 1H), 7.11-7.35 (m, 5H), 7.81 (s, 1H), 11.71 (s, 1H); MS (ES): 268.2 (M$^+$+1).

Preparation 10 dl-5,6-dimethyl-2-phenyl-7H-7-(1-phenylethyl)pyrrolo[2,3d]pyrimidin-4(3H)-one (1.0 g, 2.91 mmol) was suspended in polyphosphoric acid (30.0 mL). The mixture was heated at 100° C. for 4 hr. The hot suspension was poured onto ice water, stirred vigorously to disperse suspension, and basified to pH 6 with solid KOH. The resulting solid was filtered and collected to give 0.49 g (69%) of 5,6-dimethyl-2-phenyl- 7H-pyrrolo[2,3d]pyrimidin-4(3H)-one. $^1$H NMR (200 MHz, DMSO-d$_6$) δ 2.17 (s, 3H), 2.22 (s, 3H), 7.45 (br, 3H), 8.07 (br, 2H,), 11.49 (s, 1H), 11.82 (s, 1H); MS (ES): 344.2 (M$^+$+1).

Preparation 11

A solution of 5,6-dimethyl-2-phenyl-7H-pyrrolo[2,3d]pyrimidin-4(3H)-one (1.0 g, 4.2 mmol) in phosphorus oxychloride (25.0 mL) was refluxed for 6 hr and then concentrated in vacuo to dryness. Water was added to the residue to induce crystallization and the resulting solid was filtered and collected to give 0.90 g (83%) of 4-chloro-5,6-dimethyl-2-phenyl-7H-pyrrolo[2,3d]pyrimidine. $^1$H NMR (200 MHz, DMSO-d$_6$) δ 2.33 (s, 3H), 2.33 (s, 3H), 7.46-7.49 (m, 3H), 8.30-8.35 (m, 2H), 12.20 (s, 1H); MS (ES): 258.1 (M$^+$+1).

Preparation 12

To a solution of dl-1,2-diaminopropane (1.48 g, 20.0 mmol) and sodium carbonate (2.73 g, 22.0 mmol) in dioxane (100.0 mL) and water (100.0 mL) was added di-tert-dicarbonate (4.80 g, 22.0 mmol) at room temperature. The resulted mixture was stirred for 14 hr. Dioxane was removed in vacuo. The precipitate was filtered off and the filtrate was concentrated in vacuo to dryness. The residue was triturated with EtOAc and then filtered. The filtrate was concentrated in vacuo to dryness to give a mixture of dl-1-amino-2-(1,1-dimethylethoxy)carbonylamino-propane and dl-2-amino-1-(1,1-dimethylethoxy)carbonylamino-propane which were not separable by normal chromatography method.

Preparation 13

To solution of Fmoc-β-Ala-OH (1.0 g, 3.212 mmol) and oxalyl chloride (0.428 g, 0.29 mL, 3.373 mmol) in dichloromethane (20.0 mL) was added a few drops of N,N-dimethylformamide at 0° C. The mixture was stirred at room temperature for 1 hr followed by addition of cyclopropylmethylamine (0.229 g, 0.28 mL, 3.212 mmol) and triethylamine (0.65 g, 0.90 mL, 6.424 mmol). After 10 min, the mixture was treated with 1 M hydrochloride (10.0 mL) and the aqueous mixture was extracted with dichloromethane (3×30.0 mL). The organic solution was concentrated in vacuo to dryness. The residue was treated with a solution of 20% piperidine in N,N-dimethylforamide (20.0 mL) for 0.5 hr. After removal of the solvent in vacuo, the residue was treated with 1 M hydrochloride (20.0 mL) and ethyl acetate (20.0 mL). The mixture was separated and the aqueous layer was basified with solid sodium hydroxide to pH=8. The precipitate was removed by filtration and the aqueous solution was subjected to ion exchange column eluted with 20% pyridine to give 0.262 g (57%) of N-cyclopropylmethyl β-alanine amide. $^1$H NMR (200 MHz, CD$_3$OD) δ 0.22 (m, 2H), 0.49 (m, 2H), 0.96 (m, 2H), 2.40 (t, 2H), 2.92 (t, 2H), 3.05 (d, 2H); MS (ES): 143.1 (M$^+$+1).

Preparation 14

N-tert-butoxycarbonyl-trans-1,4-cyclohexyldiamine trans-1,4-cyclonexyldiamine (6.08 g, 53.2 mmol) was dissolved in dichloromethane (100 mL). A solution of di-t-butyldicarbonate (2.32 g, 10.65 mmol in 40 mL dichloromethane) was added via cannula. After 20 hours, the reaction was partitioned between CHCl$_3$ and water. The layers were separated and the aqueous layer was extracted with CHCl$_3$ (3×). The combined organic layers were dried over MgSO$_4$, filtered and concentrated to yield 1.20 g of a white solid (53%). $^1$H-NMR (200 MHz, CDCl$_3$): δ 1.0-1.3 (m, 4H), 1.44 (s, 9H), 1.8-2.1 (m, 4H), 2.62 (brm, 1H), 3.40 (brs, 1H), 4.37 (brs, 1H0; MS (ES): 215.2 (M$^+$+1).

4-(N-acetyl)-N-tert-butoxycarbonyl-trans-1,4-cyclohexyl diamine

N-tert-butoxycarbonyl-trans-1,4-cyclohexyldiamine (530 mg, 2.47 mmol) was dissolved in dichloromethane (20 mL). Acetic anhydride (250 mg, 2.60 mmol) was added dropwise. After 16 hours, the reaction was diluted with water and CHCl$_3$. The layers were separated and the aqueous layer was extracted with CHCl$_3$ (3×). The combined organic layers were dried over MgSO$_4$, filtered and concentrated. Recrystallization (EtOH/H$_2$O) yielded 190 mg of white crystals (30%). $^1$H NMR (200 MHz, CDCl$_3$): δ 0.9-1.30 (m, 4H), 1.43 (s, 9H), 1.96-2.10 (m, 7H), 3.40 (brs, 1H), 3.70 (brs, 1H), 4.40 (brs, 1H), 4.40 (brs, 1H); MS (ES): 257.2 (M$^+$+1), 242.1 (M$^+$−15), 201.1 (M$^+$−56).

4-(4-trans-acetamidocyclohexyl)amino-5,6-dimethyl-2-phenyl-7H-(1-phenylethyl)pyrrolo[2,3d]pyrimidine 4-(N-acetyl)-N-tert-butoxycarbonyl-trans-1,4-cyclohexyldiamine (190 mg, 0.74 mmol), was dissolved in dichloromethane (5 mL) and diluted with TFA (6 ml). After 16 hours, the reaction was concentrated. The crude solid, DMSO (2 mL), NaHCO$_3$ (200 mg, 2.2 mmol) and 4-chloro-5,6-dimethyl-2-phenyl-7H-pyrrolo[2,3d]pyrimidine (35 mg, 0.14 mmol) were combined in a flask and heated to 130° C. After 4.5 hours, the reaction was cooled to room temperature and diluted with EtOAc and water. The layers were separated and the aqueous layer was extracted with EtOAc (3×). The combined organic layers were dried over MgSO$_4$, filtered and concentrated. Chromatography (silica preparatory plate; 20:1 CHCl$_3$:EtOH) yielded 0.3 mg of a tan solid (1% yield). MS (ES): 378.2 (M$^+$+1).

4-(N-methanesulfonyl)-N-tert-butoxycarbonyl-trans-1,4-cyclohexyldiamine trans-1,4-cyclohexyldiamine (530 mg, 2.47 mmol) was dissolved in dichloromethane (20 ml) and diluted with pyridine (233 mg, 3.0 mmol). Methanesulfonyl chloride (300 mg, 2.60 mmol) was added dropwise. After 16 hours, the reaction was diluted with water and CHCl$_3$. The layers were separated and the aqueous layer was extracted with CHCl$_3$ (3×). The combined organic layers were dried over MgSO$_4$, filtered and concentrated. recrystallization (EtOH/H$_2$O) yielded 206 mg of white crystals (29%). $^1$H-NMR (200 MHz, CDCl$_3$): δ 1.10-1.40 (m, 4H), 1.45 (s, 9H), 2.00-2.20 (m, 4H), 2.98 (s, 3H), 3.20-3.50 (brs, 2H), 4.37 (brs, 1H); MS (ES) 293.1 (M$^+$+1), 278.1 (M$^+$−15), 237.1 (M$^+$−56).

4-(4-trans-methanesulfamidocyclohexyl)amino-5,6-dimethyl-2-phenyl-7H-(1-phenylethyl)pyrrolo[2,3d] pyrimidine 4-(N-sulfonyl)-N-tert-butoxycarbonyl-trans-1,4-cyclohexyldiamine (206 mg, 0.71 mmol), was dissolved in dichloromethane (5 ml) and diluted with TFA (6 ml). After 16 hours, the reaction was concentrated. The crude reaction mixture, DMSO (2 ml), NaHCO$_3$ (100 mg, 1.1 mmol) and 1-chloro-5,6-dimethyl-2-phenyl-7H-pyrrolo[2,3d]pyrimidine were combined in a flask and heated to 130° C. After 15 hours, the reaction was cooled to room temperature, and diluted with EtOAc (3×). The combined organic layers were dried over MgSO$_4$, filtered and concentrated. Chromatography (silica preparatory plate, 20:1 CHCl$_3$/EtOH) yielded 2.6 mg of a tan solid (5% yield). MS (ES): 414.2 (M$^+$+1).

Scheme IX

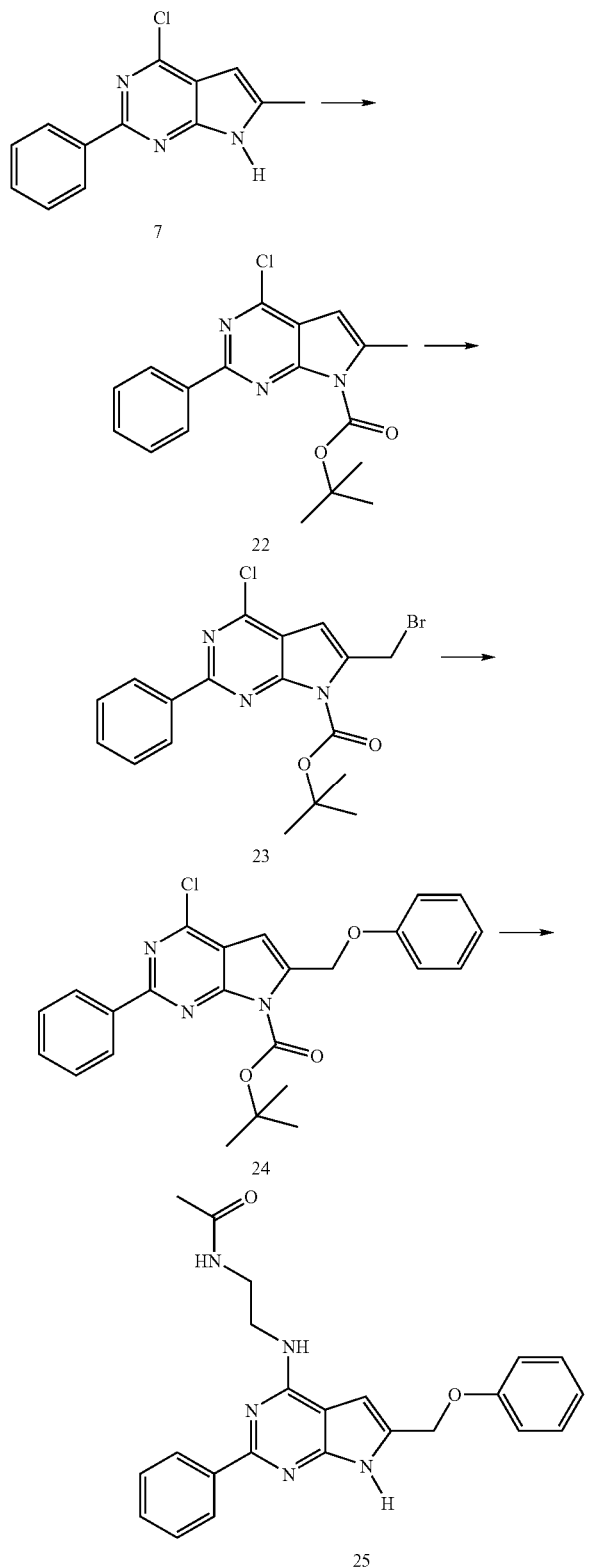

The pyrrole nitrogen of (7) (Scheme IX) was protected with di-t-butyldicarbonate under basic conditions to yield the corresponding carbamate (22). Radical bromination of (22) proceeded regioselectively to yield bromide (23). In general, compound (23) served as a key electrophilic intermediate for various nucleophilic coupling partners. Displacement of the alkyl bromide with sodium phenolate trihydrate yielded compound (24). Subsequent displacement of the aryl chloride and removal of the t-butyl carbamate protecting group occurred in one step yielding desired compound (25).

Detailed Synthesis of Compounds (22)-(25) in Accordance with Scheme IX

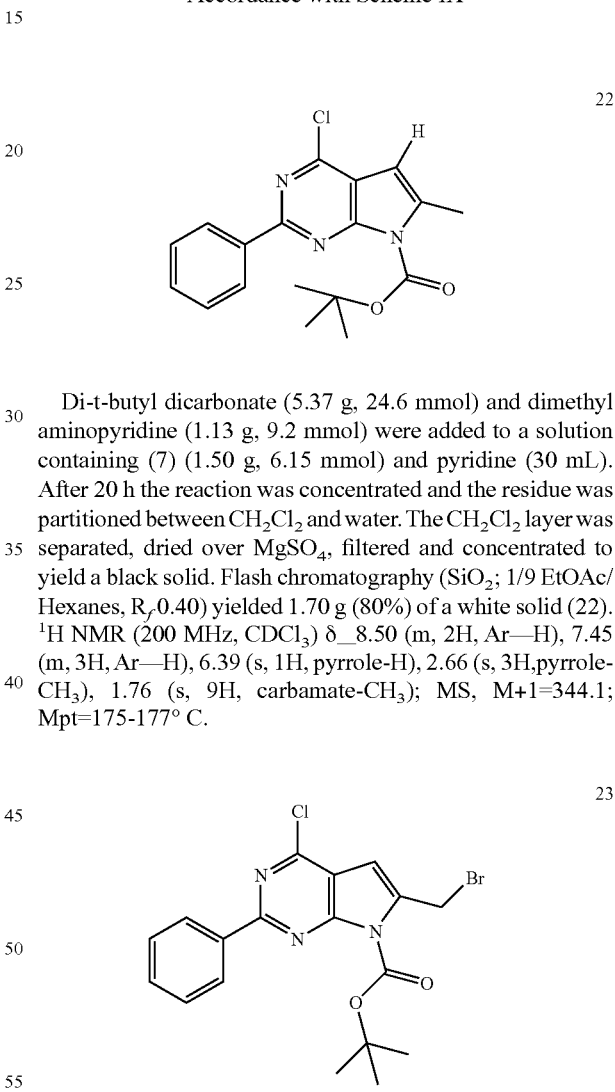

Di-t-butyl dicarbonate (5.37 g, 24.6 mmol) and dimethyl aminopyridine (1.13 g, 9.2 mmol) were added to a solution containing (7) (1.50 g, 6.15 mmol) and pyridine (30 mL). After 20 h the reaction was concentrated and the residue was partitioned between CH$_2$Cl$_2$ and water. The CH$_2$Cl$_2$ layer was separated, dried over MgSO$_4$, filtered and concentrated to yield a black solid. Flash chromatography (SiO$_2$; 1/9 EtOAc/Hexanes, R$_f$ 0.40) yielded 1.70 g (80%) of a white solid (22). $^1$H NMR (200 MHz, CDCl$_3$) δ 8.50 (m, 2H, Ar—H), 7.45 (m, 3H, Ar—H), 6.39 (s, 1H, pyrrole-H), 2.66 (s, 3H, pyrrole-CH$_3$), 1.76 (s, 9H, carbamate-CH$_3$); MS, M+1=344.1; Mpt=175-177° C.

N-Bromosuccinimide (508 mg, 2.86 mmol) and AIBN (112 mg, 0.68 mmol) were added to a solution containing (22) (935 mg, 2.71 mmol) and CCl$_4$ (50 mL). The solution was heated to reflux. After 2 h the reaction was cooled to room temperature and concentrated in vacuo to yield a white solid. Flash chromatography (SiO$_2$; 1/1 CH$_2$Cl$_2$/Hexanes, R$_f$ 0.30) yielded 960 mg (84%) of a white solid (23). $^1$H NMR (200 MHz, CDCl$_3$) δ 8.52 (m, 2H, Ar—H), 7.48 (m, 3H, Ar—H), 6.76 (s, 1H, pyrrole-H), 4.93 (s, 2H, pyrrole-CH$_2$Br), 1.79 (s, 9H, carbamate-CH$_3$); MS, M+1=423.9; Mpt=155-157° C.

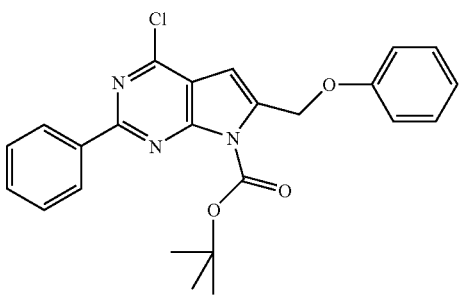

Sodium phenoxide trihydrate (173 mg, 1.02 mmol) was added in one portion to a solution of bromide (23) (410 mg, 0.97 mmol) dissolved in $CH_2Cl_2$ (5 mL) and DMF (10 mL). After 2 h the reaction solution was partitioned between $CH_2Cl_2$ and water. The water layer was extracted with $CH_2Cl_2$. The combined $CH_2Cl_2$ layers were washed with water, dried over $MgSO_4$, filtered and concentrated to yield a yellow solid. Flash chromatography ($SiO_2$; 1/6 EtOAc/Hexanes, $R_f$ 0.30) yielded 210 mg (50%) of a white solid (24). $^1$H NMR (200 MHz, $CDCl_3$) δ 8.53 (m, 2H, Ar—H), 7.48 (m, 3H, Ar—H), 7.34 (m, 2H, Ar—H), 7.03 (m, 3H, Ar—H), 6.83 (s, 1H, pyrrole-H), 5.45 (s, 2H, $ArCH_2O$), 1.76 (s, 9H, carbamate-$CH_3$); MS, $M^+$=436.2.

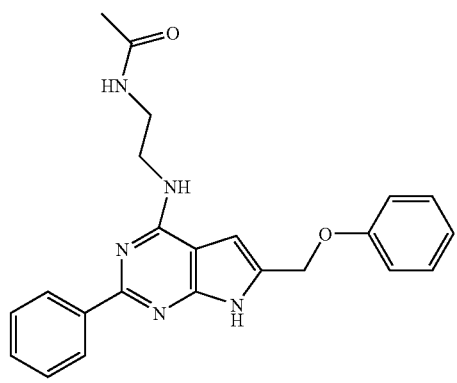

A solution containing (24) (85 mg, 0.20 mmol), N-acetylethylenediamine (201 mg, 1.95 mmol) and DMSO (3 mL) was heated to 100° C. After 1 h the temperature was raised to 130° C. After 3 h the reaction was cooled to room temperature and partitioned between EtOAc and water. The water layer was extracted with EtOAc (2×). The combined EtOAc layers are washed with water, dried over $MgSO_4$, filtered and concentrated. Flash chromatography ($SiO_2$; 1/10 EtOH/$CHCl_3$, $R_f$ 0.25) yielded 73 mg (93%) of a white foamy solid (25). $^1$H NMR (200 MHz, DMSO-$d_6$) δ 11.81 (br s, 1H, N—H), 8.39 (m, 2H, Ar—H), 8.03 (br t, 1H, N—H), 7.57 (br t, 1H, N—H), 7.20-7.50 (m, 5H, Ar—H), 6.89-7.09 (m, 3H, Ar—H), 6.59 (s, 1H, pyrrole-H), 5.12 (s, 2H, $ArCH_2O$), 3.61 (m, 2H, $NCH_2$), 3.36 (m, 2H, $NCH_2$), 1.79 (s, 3H, $COCH_3$); MS, M+1=402.6

Example 1

Adenosine $A_3$ Antagonist Experimentals

Compound 1720: $^1$H-NMR ($CD_3OD$) δ 3.05 (t, 2H, J=7.0 Hz), 3.94 (t, 2H, J=7.0 Hz), 6.50 (d, 1H, J=3.5 Hz), 6.88 (brs, 1H), 7.04 (d, 1H, J=3.5 Hz), 7.42 (m, 3H), 7.57 (s, 1H), 8.34 (m, 2H); MS (ES): 305.1 ($M^+$+1); Mpt=234-235° C.

Compound 1721: (20%). $^1$H NMR ($CD_3OD$, 400 MHz) δ 3.22 (t, 2H, J=6.4 Hz), 4.11 (t, 2H, J=6.4 Hz), 6.73 (s, 2H), 7.26 (d, 1H, J=3.2 Hz), 7.37 (s, 1H), 7.57 (m, 2H), 8.15 (m, 1H), 8.22 (m, 1H), 8.71 (s, 1H); MS (ES) 338.95, 340.95 (M, M+2).

Compound 1722: (41%). Mp 199-200° C. $^1$H NMR ($CD_3OD$, 200 MHz) δ 3.25 (m, 2H), 4.05 (t, 2H, J=7.0 Hz), 6.48 (d, 1H, J=3.8 Hz), 7.05 (d, 1H, J=3.6 Hz); MS (ES) 349.93, 351.94 (M, M+2).

Compound 1723: (84%). Mp 183-185° C. $^1$H NMR ($CD_3OD$, 200 MHz) δ 2.24 (m, 2H), 3.69 (t, 2H, J=6.6 Hz), 4.18 (t, 2H, J=7 Hz), 6.50 (d, 1H, J=3.6 Hz), 7.06 (m, 3H), 7.37 (brs, 2H), 7.65 (brs, 1H), 8.25 (m, 2H); MS (ES) 352.9, 354.9 (M, M+2).

Compound 1724: (83%). $^1$H NMR ($d_6$-DMSO, 200 MHz) δ 3.15 (m, 2H), 3.82 (m, 2H), 6.45 (m, 1H), 7.12 (m, 1H), 7.41 (m, 2H), 7.55 (m, 2H), 7.74 (m, 1H), 7.02 (s, 1H), 8.38 (m, 1H, ), 8.46 (m, 1H). MS (ES) 315.95 (M+1).

Compound 1725: (70%). $^1$H NMR ($d_6$-DMSO, 200 MHz) δ 3.15 (m, 2H), 3.82 (m, 2H), 6.45 (m, 1H), 7.12 (m, 1H), 7.41 (m, 2H), 7.55 (m, 2H), 7.74 (m, 1H), 7.02 (s, 1H), 8.38 (m, 1H), 8.46 (m, 1H). MS (ES) 315.97 (M+1).

Compound 1726: (58%). $^1$H NMR ($d_6$-DMSO, 200 MHz) δ 3.01 (m, 2H), 3.82 (m, 2H), 6.45 (m, 1H), 7.12 (m, 1H), 7.41 (m, 2H), 7.55 (m, 2H), 7.74 (m, 1H), 7.02 (s, 1H), 8.38 (m, 1H), 8.46 (m, 1H). MS (ES) 315.99 (M+1).

Compound 1727: (64%). $^1$H NMR ($d_6$-DMSO, 200 MHz) δ 3.20(m, 2H) 3.40 (s, 3H) 4.2 (m, 2H), 6.65 (m, 1H), 7.12 (m, 1H), 7.41 (m, 2H), 7.55 (m, 2H), 7.74 (m, 1H), 7.02 (s, 1H), 8.38 (m, 1H), 8.46 (m, 1H). MS (ES) 329.99 (M+1).

Compound 1728: (30%). $^1$H NMR ($d_6$-DMSO, 200 MHz) δ 2.82 (t, 2H, J=7.8 Hz), 3.5 (s, 3H), 3.69 (t, 2H, J=8.4 Hz), 6.51 (m, 1H), 6.89 (s, 1H), 7.049 (s, 1 H), 7.41 (m, 3H, J=7 Hz), 8.34 (d, 2H, J=5.8 Hz). MS (ES) 318.99 (M+1).

Compound 1729: (29%). $^1$H NMR ($d_6$-DMSO, 200 MHz) δ 2.82 (t, 2H, J=7.8 Hz), 3.5 (s, 3H), 3.69 (t, 2 H, J=8.4 Hz), 6.51 (d, 1H), 6.89 (s, 1H), 7.049 (s, 1H), 7.41 (m, 3H, J=7 Hz), 8.34 (d, 2H, J=7.6 Hz). MS (ES) 319.03 (M+1).

Compound 1730: $^1$H NMR ($d_6$-DMSO, 200 MHz) δ 1.74 (m, 2H), 3.10 (dt, 2H, J=6.2, 6.2 Hz), 3.56 (dt, 2H, J=6.2 Hz), 5.67 (m, 1H), 5.93 (t, 1H, J=5.6 Hz), 6.54 (dd, 1H, J=1.8, 3.2 Hz), 7.10 (dd, 1H, J=2.4, 3.5 Hz), 7.40-7.54 (m, 3H), 8.30 (m, 2H), 11.38 (brs, 1H); MS (ES): 359.0 ($M^+$+1).

Compound 1731: $^1$H NMR ($d_6$-DMSO, 400 MHz) δ 2.31 (s, 3H), 2.89 (m, 2H), 3.75 (dd, 2H, J=8.0, 13.6 Hz), 6.21 (s, 1H), 6.84 (s, 1H), 7.43 (m, 3H), 7.54 (s, 1H), 8.34 (m, 2H), 11.45 (s, 1H), 11.83 (brs, 1H). MS (ES) 352.9 (M+1, $^{35}$Cl), 354.9 (M+1, $^{37}$Cl).

Compound 1732: (62%). $^1$H NMR (d6-DMSO, 200 MHz) δ 2.12(tt,2H, J=7 Hz), 3.57(dt,2H, J=6.6 Hz), 4.11(t,2H, J=7 Hz), 6.5-6.7(m,1H), 6.93(s,1H), 7.15-7.25(m,1H), 7.24(dd, 1H, J=1 Hz), 7.35-7.55(m,4H), 7.68(s,1H), 8.28-8.38(m,2H), 11.58(s,1H) MS(ES) 318.98(M+1).

Compound 1733: (75%). $^1$H NMR (d6-DMSO,200 MHz) δ 2.7-2.9(m, 2H), 4.17-4.33(m, 2H), 4.9-5.1(m,2H), 6.687(d, 1H, J=), 7.26(d, 1H, J=) 7.35-7.55(m,4H), 8.35-8.48(m, 2H), 11.7-11.9(m,1H). MS(ES) 316.95(M+1).

Compound 1735: (32%). $^1$H NMR ($d_6$-DMSO, 200 MHz ) δ 2.63 t, 2H, J=9.4 Hz ), 2.92 (t, 2H, J=9.4 Hz ), 3.75 (s, 3H, 6.51 (s, 1H), 6.81(s, 1H), 6.94 (d, 1H, J=7 Hz), 7.04 (d, 1H), 7.27(t, 1H), 7.5 (s, 1H), 7.93 (d, 1H, J=8.4 Hz ). MS (ES) 324.94 (M+1).

Example 2

Adenosine A₁ Antagonist Experimentals

Compound 1631 (salt): $^1$H NMR (d$_6$-DMSO, 200 MHz) δ 2.05 (m, 1H), 2.23 (m, 1H), 2.38 (s, 3H), 3.90 (m, 1H), 4.15 (m, 1H), 4.51 (brs, 1H), 4.83 (m, 1H), 6.73 (brs, 1H), 7.07 (brs, 1H), 7.29 (s, 1H), 7.51 (m, 3H), 7.69 (s, 1H), 8.29 (m, 2H), 12.02 (brs, 1H). MS (ES) 323.9 (M+1).

Example 3

Synthesis of [2-(3H-Imidazol-4-yl)-ethyl]-(2-phenyl-7H-pyrrolo[2,3-d]pyrimidin-4-yl)-amine (1720)

Compound 1720 was synthesized using precursor compound 1 of synthesis scheme VII to obtain:

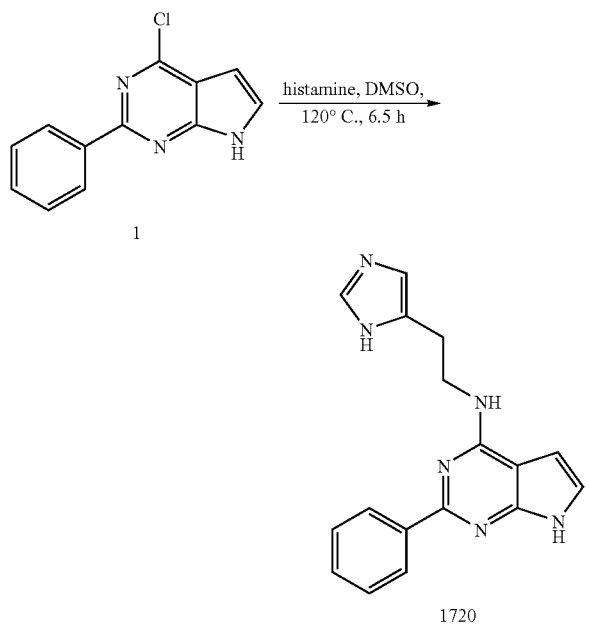

Aryl chloride 1 (400 mg, 1.50 mmol), DMSO (10 mL) and histamine (1.67 g, 15.0 mmol) are combined and heated to 120° C. under nitrogen. After 6.5 h, the reaction is cooled to room temperature and partitioned between EtOAc and water. The layers are separated and the aqueous layer is extracted with EtOAc (3×). The combined organic layers are washed with brine (2×), dried over MgSO₄, filtered and concentrated to yield 494 mg of a brown solid. The solid is washed with cold MeOH and recrystallized from MeOH to yield 197 mg (43%) of an off white solid (1720). $^1$H-NMR (CD₃OD) d 3.05 (t, 2H, J=7.0 Hz), 3.94 (t, 2H, J=7.0 Hz), 6.50 (d, 1H, J=3.5 Hz), 6.88 (brs, 1H), 7.04 (d, 1H, J=3.5 Hz), 7.42 (m, 3H), 7.57 (s, 1H), 8.34 (m, 2H); MS (ES): 305.1 (M⁺+1); Mpt=234-235° C.

Example 4

Synthesis of Compounds 1721-1723

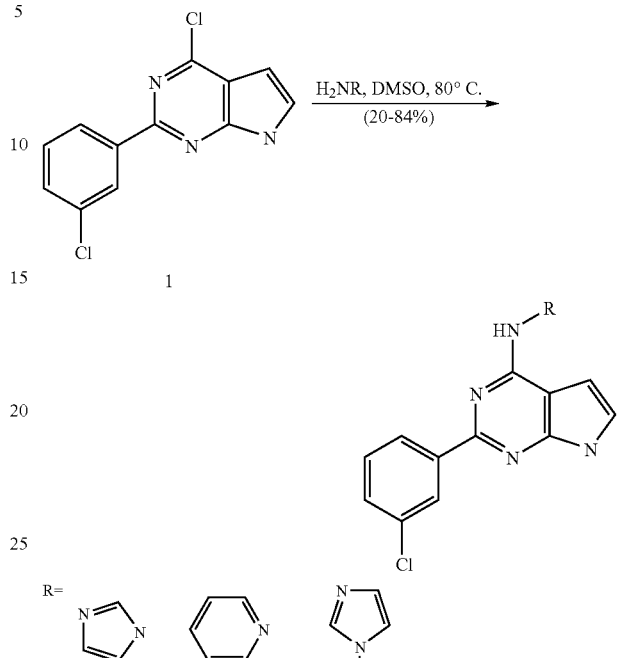

Compound 1 (100 mg, 0.33 mmol) and histamine (185 mg, 1.66 mmol) are dissolved in DMSO (2 mL). The reaction was stirred under argon at 80° C. for 10 hrs. The reaction was partitioned between EtOAc and water. The layers were separated and the aqueous layer was re-extracted with EtOAc (1-2% MeOH). The combined organic layers were washed with water (2×) and brine, dried over MgSO₄, filtered and concentrated to a brown oil. The compound was purified by Prep TLC with 10% MeOH in MeCl₂ to yield 22.6 mg (20%) of a white solid.

Example 5

Synthesis of Compounds 1724, 1725, 1726, 1727, 1728, 1729 and 1735

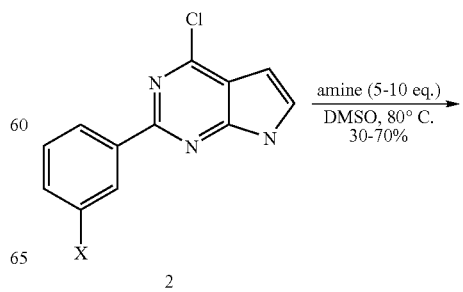

-continued

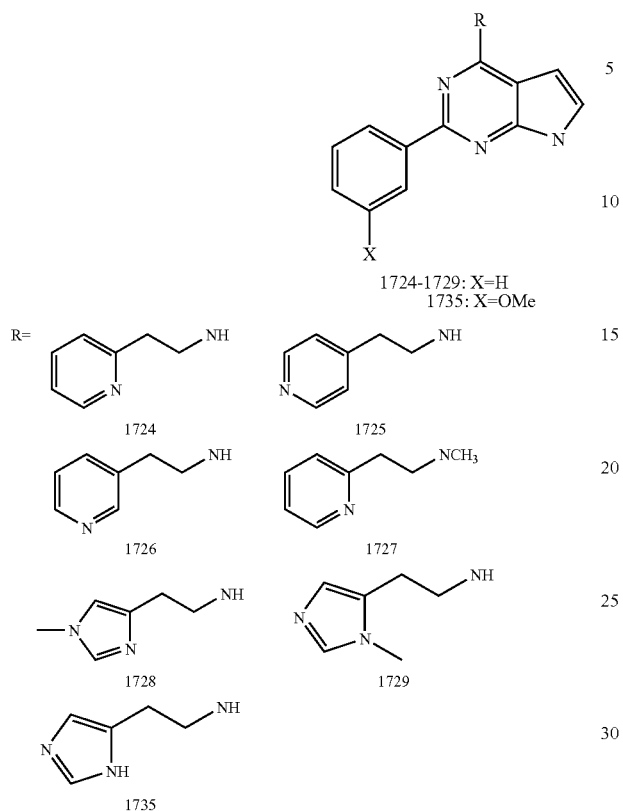

1724-1729: X=H
1735: X=OMe

Compound 2 (Synthesized via Scheme VII), (100 mg, 0.34 mmol), histamine dihydrochloride (497 mg, 2.69 mmol), potassium bicarbonate (572 mg, 5.72 mmol) were dissolved in 0.5 ml DMSO under nitrogen. The mixture was heated to 80 deg. C. for 12 hours. The reaction seemed to be complete as judged by TLC (5% MeOH/CHCl$_3$). The mixture was diluted with water (5 ml), and was extracted with 5% MeOH in CHCl$_3$ (3×10 ml). The organic phases were combined, dried over Na$_2$SO$_4$, and filtered. The solvents were removed to afford a brown oil. The oil was chromatographed in SiO$_2$ (5% MeOH/CHCl$_3$). The solvents were removed to give an off-white solid (36 mg) as product.

Example 6

Compound 1731 was Synthesized According to the Following Scheme

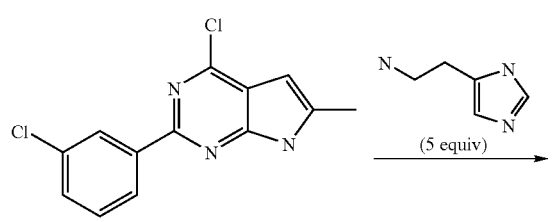

-continued

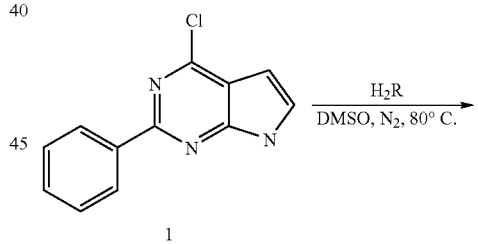

1731

4-Chloro-6-methyl-2-phenyl-7H-pyrrolo[2,3-d]pyrimidine hydrochloride (533 mg, 1.69 mmol) and histamine (942 mg, 8.47 mmol) were dissolved in DMSO (10 mL). The reaction was then heated to 80° C. After 19 h, the reaction was cooled to room temperature and partitioned between EtOAc and water. The aqueous layer was extracted with EtOAc (3×). The organic layers were combined, washed with water and then brine, dried over MgSO4, filtered and concentrated to yield 640 mg of brown oil. The oil was dissolved in 10% MeOH in CHCl$_3$ and the resulting precipitate was filtered to yield 405 mg pale orange column. Reverse phase flash chromatography (C18, gradient 50% MeOH (aq)—100% MeOH) removed the color and yielded 330 mg of a white solid (55%). The solid was dissolved in EtOH and gravity filtered. The resulting solution was slowly diluted with water until a precipitate formed and allowed to stand. The solid was filtered, washed with 50% EtOH (aq) and dried overnight (60° C., 0.1 mmHg) to yield 250 mg white solid. Mp 215-217° C. IR 1542, 1568, 1586 cm$^{-1}$.

Example 7

Synthesis of Compounds 1732

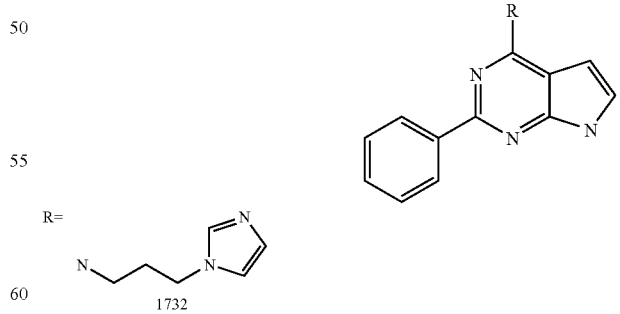

1732

General procedure for synthesis of compound 1732: Compound 1 (4.75, 0.17.9 mmol) and histamine (5.98 g, 53.8 mmol) are dissolved in DMSO (Anhy., 40 mL) and heated to 80° C. in an oil-bath and stirred under nitrogen overnight. After ~10 h, the reaction was concentrated in-vacuo. The residue was partitioned between CHCl₃/MeOH and water. The layers were separated and the aqueous layer was re-extracted with CHCl₃/MeOH (3×). The combined organic layers were washed with brine (1×), dried over Na₂SO₄, filtered and concentrated to yield a dark brown oil which was subsequently triturated with CHCl₃/MeOH (90/10). This resulted, over time (overnight), in a precipitate, which was filtered and washed with CHCl₃ to yield 4.95 g (91%) of an off-white/tan solid. This material looked >97% pure by H NMR and LC-MS data.

The colored impurity was removed by dissolving material in a 50/50 (~600 mL) EtOH/H₂O mixture with heating. Once dissolved material was allowed to cool to room-temperature and passed through a 55 g C-18 pre-packed column (Biotage-KP-C18-HS) using the Biotage system. A gradient system was run collecting 250 mL fractions and eluting with 1.2 L of 50/50 EtOH/H₂O; 0.75 L of 60/40 EtOH/H₂O; 0.75 L of 75/25 EtOH/H₂O; and finally 0.75 L of 100% EtOH. The fractions were collected and spun down using a Savant speed-vac and the pure fraction were re-dissolved in 100% warm EtOH and gravity filtered through filter paper to remove any C-18 residue and sample was then crystallized/precipitated out from EtOH/H₂O to give 2.67 g of an off-white solid which looked >99% pure by H NMR and LC-MS.

Example 8

Synthesis of Compound 1733

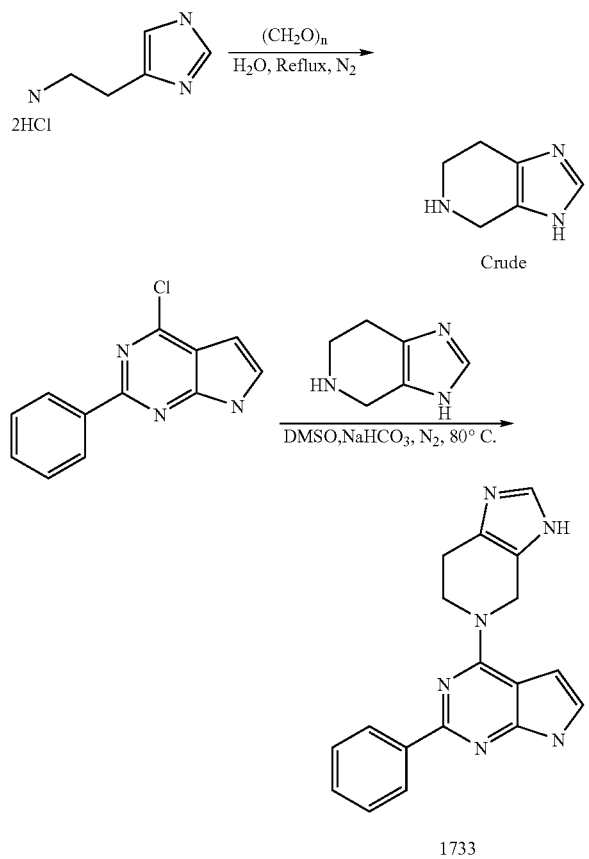

Histamine dihydrochloride (500 mg, 2.71 mmol) and paraformaldehyde (122 mg, 4.1 mmol) where dissolved in H₂O(6 mL) and refluxed for 4 h. From LC-MS all SM appeared to be consumed after 4 hs. The reaction mixture was concentrated and resulted in 520 mg of a light-yellow solid, which was used as crude in the next step chloride displacement.

Chloride replacement proceeded as in example 21.

Example 9

Synthesis of Compound 1631

Synthesis of (2S, 4R)-4-Hydroxy-1-(2-phenyl-7H-pyrrolo[2,3-d]pyrimidin-4-yl)-pyrrolidine-2-carboxylic acid amide methane sulfonate (1631)

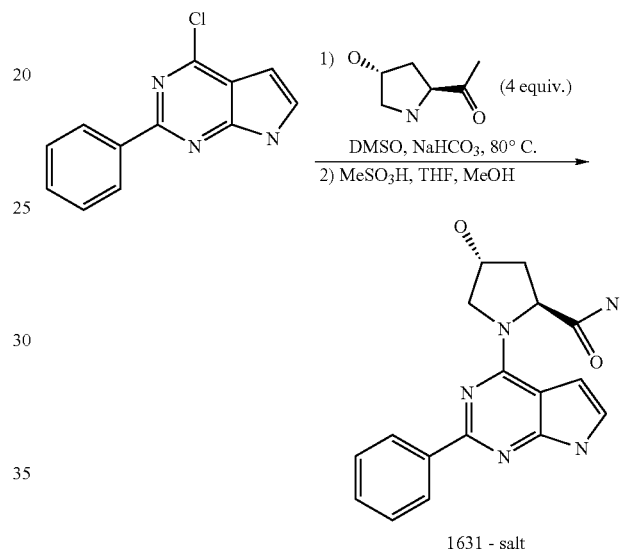

1631 - salt

The following synthesis data is for the salt of compound 1631.

4-Chloro-2-phenyl-7H-pyrrolo[2,3-d]pyrimidine (4.4 g, 16.5 mmol)(Scheme VII), NaHCO₃ (2.9 g, 33 mmol) and trans-4-hydroxy-(L)-prolineamide (8.6 g, 66.1 mmol) were dissolved in DMSO (80 mL). The reaction was then heated to 80° C. After 20 h, the reaction was cooled to room temperature and partitioned between EtOAc and water. The aqueous layer was extracted with EtOAc (7×). The organic layers were combined, washed with water and then brine, dried over MgSO₄, filtered and concentrated to yield 4.8 g of a brown solid. The solid was combined with CH₃OH (50 mL) and heated at reflux for 0.5 h. After cooling to room temperature, the heterogeneous solution was filtered and washed with CH₃OH to yield 3.44 g (74%) of a tan solid. The free base (3.1 g, 9.65 mmol) was dissolved in a mixture of EtOH and THF (300 mL; 5:3 EtOH/THF). Methane sulfonic acid (927 mg, 9.65 mmol) was then added slowly to the homogeneous solution. The precipitate was separated from the solution by filtration and washed with 5:3 EtOH/THF. The sample was dried (60° C., 0.1 mmHg) and yielded 3.4 g (84%) of a tan solid. Mp 257-258° C. (decomp.).

Activity of Compounds

Adenosine 3 (A₃) receptor competition radio ligand binding was carried out for compound 1720 as described herein and inter alia, on pages 134-135 of this specification. Compound 1720 was found to have an A₃ receptor binding affinity greater than 10 times that of reference compound 1308 as described herein and, inter alia, in Table 8, on pages 138-141 of the specification. Binding and solubility data for the compounds of the invention is presented in Table 3.

Similar $A_3$ receptor competition radio ligand binding was carried out for compounds 1721-1735. Compounds 1721-1729 and 1730-1735 illustrated a higher affinity for the $A_3$ receptor relative to their respective $A_1$ receptor binding affinities. Of these, compounds 1721, 1730, 1731, 1733 and 1735 were found to have properties superior to those of compound 1720 and thus also to reference compound 1308, as illustrated in Table 3 below. Thus, compounds 1721, 1730, 1731, 1733 and 1735 display properties which are significantly better than the rest of the disclosed $A_3$ compounds.

Adenosine 1 ($A_1$) receptor subtype saturation and competition radio ligand binding was carried out for compound 1631 as described herein and inter alia, on pages 134-135 of this specification. The compound equaled or surpassed the $A_1$ receptor binding affinity of reference compounds 1318 or 1319 as described herein and, inter alia, in Table 8, on pages 138-141 of the specification.

The water solubility of compound 1631 is expected to be better than reference compounds 1318 or 1319 due its cLogP value, which was calculated using the computer program CS ChemDraw, ChemDraw Ultra ver. 6.0 ©1999 as provided by CambridgeSoft Corporation, 100 Cambridge Park Drive, Cambridge, Mass. 02140. The cLogP value for compound 1631 is 2.05.

Compound 1631 had a lower cLogP value, as compared to reference compounds 1318 or 1319 with a cLogP value about 3.8. It was not predicted that a more polar $A_1$ receptor compound having a lower cLogP value than the reference compounds 1318 or 1319 would still retain the potency and $A_1$ receptor binding selectivity as compared to those reference compounds.

TABLE 3

Properties of compounds 1721, 1730, 1731, 1733 and 1735 relative to compound 1720.

| Compound | Binding Affinity for $A_3$ receptor relative to compound 1720 | Selectivity for $A_3$ over $A_1$ receptor relative to compound 1720 | Solubility (cLog P) relative to compound 1720 |
| --- | --- | --- | --- |
| 1721 | Higher | ~2.5 × more selective | More soluble |
| 1730 | Higher | ~4 × more selective | More soluble |
| 1731 | Similar | ~2 × more selective | Slightly less soluble |
| 1733 | Similar | ~7 × more selective | Slightly less soluble |
| 1735 | Higher | ~30 × more selective | More soluble |

Yeast β-Galactosidase reporter gene assays for human adenosine $A_1$ and $A_{2a}$ receptor: Yeast strains (*S. cerevisiae*) were transformed with human adenosine $A_1$ ($A_1R$; CADUS strain CY12660) or human $A_{2a}$ ($A_{2a}$; CADUS strain CY8362) and the addition of a lacZ(β-Galactosidase) reporter gene to utilize as a functional readout. A complete description of the transformations is listed below (see Yeast Strains). NECA (5'-N-ethylcarboxamidoadenosine), a potent adenosine receptor agonist with similar affinity for $A_1$ and $A_{2a}$ receptors, was used as a ligand for all assays. Test compounds were examined at 8 concentrations (0.1-10,000 nM) for ability to inhibit NECA-induced β-Galactosidase activity by CY12660 or CY8362.

Preparation of Yeast Stock Cultures: Each of the respective yeast strains, CY12660 and CY8362, were streaked onto an LT agar plate and incubated at 30° C. until colonies were observed. Yeast from these colonies were added to LT liquid (pH 6.8) and grown overnight at 30° C. Each yeast strain was then diluted to an $OD_{600}$=1.0-2.0 (approximately 1-2×10$^7$ cells/ml), as determined spectrophotometrically (Molecular Devices VMAX). For each 6 ml of yeast liquid culture, 4 ml of 40% glycerol (1:1.5 vol:vol) was added ("yeast/glycerol stock"). From this yeast/glycerol stock, ten 1 ml aliquots were prepared and stored at −80° C. until required for assay.

Yeast $A_1$ R and $A_{2a}$R Assay: One vial each of CY8362 and CY12660 yeast/glycerol stock was thawed and used to inoculate Supplemented LT liquid media, pH 6.8 (92 ml LT liquid, to which is added: 5 ml of 40% glucose, 0.45 ml of 1M KOH and 2.5 ml of Pipes, pH 6.8). Liquid cultures were grown 16-18 hr (overnight) at 30° C. Aliquots from overnight cultures were then diluted in LT media, containing 4 U/ml adenosine deaminase (Type VI or VII from calf intestinal mucosa, Sigma), to obtain $OD_{600}$=0.15 (1.5×10$^6$ cells/ml) for CY8362 (A2aR) and $OD_{600}$=0.50 (5×10$^6$ cells/ml) for CY12660 ($A_1R$).

Assays were conducted with a final volume of 100 ul in 96-well microtiter plates, such that a final concentration of 2% DMSO was achieved in all wells. For primary screening, 1-2 concentrations of test compounds were utilized (10 uM, 1 μM). For compound profiling, 8 concentrations were tested (10000, 1000, 500, 100, 50, 10, 1 and 0.1 nM). To each microtiter plate, 10 ul of 20% DMSO was added to "Control" and "Total" wells while 10 ul of Test Compound (in 20% DMSO) was added to "Unknown" wells. Subsequently, 10 ul of NECA (5 uM for $A_1R$, 1 uM for $A_{2a}R$) were added to "Total" and "Unknown" wells; 10 ul of PBS was added to the "Control" wells. In the final addition, 80 ul of yeast strain, CY8362 or CY12660, were added to all wells. All plates were then agitated briefly (LabLine orbital shaker 2-3 min) and allowed to incubate for 4 hrs. at 30° C. in a dry oven.

β-Galactosidase activity can be quantitated using either colorimetric (e.g., ONPG, CPRG), luminescent (e.g., Galacton-Star) or fluorometric substrates (e.g., FDG, Resorufin) substrates. Currently, fluorescence detection is preferred on the basis of superior signal:noise ratio, relative freedom from interference and low cost. Fluorescein digalactopyranoside (FDG, Molecular Probes or Marker Gene Technologies), a fluorescent β-Galactosidase substrate, was added to all wells at 20 ul/well (final concentration=80 uM). Plates were shaken for 5-6 sec (LabLine orbital shaker) and then incubated at 37° C. for 90 min (95% $O_2$/5% $CO_2$ incubator). At the end of the 90 min incubation period, β-Galactosidase activity was stopped using 20 ul/well of 1M $Na_2CO_3$ and all plates shaken for 5-6 sec. Plates were then agitated for 6 sec and relative fluorescence intensity determined using a fluorometer (Tecan Spectrafluor; excitation=485 nm, emission=535 nm).

Calculations: Relative fluorescence values for "Control" wells were interpreted as background and subtracted from "Total" and "Unknown" values. Compound profiles were analyzed via logarithmic transformation (x-axis: compound concentration) followed by one site competition curve fitting to calculate $IC_{50}$ values (GraphPad Prism).

Yeast strains: *Saccharomyces cerevisiae* strains CY12660 [far1*1442 tbt1-1 fus1-HIS3 can1 ste14::trp1::LYS2 ste3*1156 gpa1(41)-Gαi3 lys2 ura3 leu2 trp1: his3; LEU2 PGKp-MfαlLeader-hA1R-PHO5term 2 mu-orig REP3 Ampr] and CY8362 [gpa1p-rGαsE10K far1*1442 tbt1-1 fus1-HIS3 can1 ste14::trp1: LYS2 ste3*1156 lys2 ura3 leu2 trp1 his3; LEU2 PGKp-hA2aR 2mu-ori REP3 Ampr] were developed.

LT Media: LT (Leu-Trp supplemented) media is composed of 100 g DIFCO yeast nitrogen base, supplemented with the following: 1.0 g valine, 1.0 g aspartic acid, 0.75 g phenylalanine, 0.9 g lysine, 0.45 g tyrosine, 0.45 g isoleucine, 0.3 g methionine, 0.6 g adenine, 0.4 g uracil, 0.3 g serine, 0.3 g proline, 0.3 g cysteine, 0.3 g arginine, 0.9 g histidine and 1.0 g threonine.

Construction of Yeast Strains Expressing Human $A_1$ Adenosine Receptor

In this example, the construction of yeast strains expressing a human $A_1$ adenosine receptor functionally integrated into the yeast pheromone system pathway is described.

I. Expression Vector Construction

To construct a yeast expression vector for the human $A_1$ adenosine receptor, the $A_1$ adenosine receptor cDNA was obtained by reverse transcriptase PCR of human hippocampus mRNA using primers designed based on the published sequence of the human $A_1$ adenosine receptor and standard techniques. The PCR product was subcloned into the NcoI and XbaI sites of the yeast expression plasmid pMP15.

The pMP15 plasmid was created from pLPXt as follows: The XbaI site of YEP51 (Broach, J. R. et al. (1983) "Vectors for high-level, inducible expression of cloned genes in yeast" p. 83-117 in M. Inouye (ed.), Experimental Manipulation of Gene Expression. Academic Press, New York) was eliminated by digestion, end-fill and religation to create Yep51NcoDXba. Another XbaI site was created at the BamHI site by digestion with BamHI, end-fill, linker (New England Biolabs, #1081) ligation, XbaI digestion and re-ligation to generate YEP51NcoXt. This plasmid was digested with Esp31 and NcoI and ligated to Leu2 and PGKp fragments generated by PCR. The 2 kb Leu2 PCR product was generated by amplification from YEP51Nco using primers containing Esp31 and BglII sites. The 660 base pair PGKp PCR product was generated by amplification from pPGKαs (Kang, Y.-S. et al. (1990) Mol. Cell. Biol. 10:2582-2590) with PCR primers containing BglII and NcoI sites. The resulting plasmid is called pLPXt. pLPXt was modified by inserting the coding region of the a-factor pre-pro leader into the NcoI site. The prepro leader was inserted so that the NcoI cloning site was maintained at the 3' end of the leader, but not regenerated at the 5' end. In this way receptors can be cloned by digestion of the plasmid with NcoI and XbaI. The resulting plasmid is called pMP15.

The pMP15 plasmid into which was inserted the human $A_1$ adenosine receptor cDNA was designated p5095. In this vector, the receptor cDNA is fused to the 3' end of the yeast a-factor prepro leader. During protein maturation the prepro peptide sequences are cleaved to generate mature full-length receptor. This occurs during processing of the receptor through the yeast secretory pathway. This plasmid is maintained by Leu selection (i.e., growth on medium lacking leucine). The sequence of the cloned coding region was determined and found to be equivalent to that in the published literature (GenBank accession numbers S45235 and S56143).

II. Yeast Strain Construction

To create a yeast strain expressing the human $A_1$ adenosine receptor, yeast strain CY7967 was used as the starting parental strain. The genotype of CY7967 is as follows:

MATα gpaD1163 gpa1(41)Gαi3 far1D1442 tbt-1 FUS1-HIS3 can1 ste14::trp1::LYS2 ste3D1156 lys2 ura3 leu2 trp1 his3

The genetic markers are reviewed below:

TABLE 4

| | |
|---|---|
| MATa | Mating type a. |
| gpa1D1163 | The endogenous yeast G-protein GPA1 has been deleted. |
| gpa1(41)Gαi3 | gpa1(41)-Gai3 was integrated into the yeast genome. This chimeric Ga protein is composed of the first 41 amino acids of the endogenous yeast Ga subunit GPA1 fused to the mammalian G-protein Gai3 in which the cognate N-terminal amino acids have been deleted. |
| far1D1442 | FAR1 gene (responsible for cell cycle arrest) has been deleted (thereby preventing cell cycle arrest upon activation of the pheromone response pathway). |
| tbt-1 | strain with high transformation efficiency by electroporation. |
| FUS1-HIS3 | a fusion between the FUS1 promoter and the HIS3 coding region (thereby creating a pheromone inducible HIS3 gene). |
| can 1 | arginine/canavinine permease. |
| ste14::trp1::LYS2 | gene disruption of STE14, a C-farnesyl methyltransferase (thereby lowering basal signaling through the pheromone pathway). |
| ste3D1156 | endogenous yeast STR, the a factor pheromone receptor (STE3) was disrupted. |
| lys2 | defect in 2-aminoapidate reductase, yeast need lysine to grow. |
| ura3 | defect in orotidine-5'-phosphate decarboxylase, yeast need uracil to grow |
| leu2 | defect in b-isopropylmalate dehydrogenase, yeast need leucine to grow. |
| trp1 | defect in phosphoribosylanthranilate, yeast need tryptophan to grow. |
| his3 | defect in imidazoleglycerolphosphate dehydrogenase, yeast need histidine to grow. |

Two plasmids were transformed into strain CY7967 by electroporation: plasmid p5095 (encoding human $A_1$ adenosine receptor; described above) and plasmid p1584, which is a FUS1-β-galactosidase reporter gene plasmid. Plasmid p1584 was derived from plasmid pRS426 (Christianson, T. W. et al. (1992) Gene 110:119-1122). Plasmid pRS426 contains a polylinker site at nucleotides 2004-2016. A fusion between the FUS1 promoter and the β-galactosidase gene was inserted at the restriction sites EagI and XhoI to create plasmid p1584. The p1584 plasmid is maintained by Trp selection (i.e., growth on medium lacking leucine).

The resultant strain carrying p5095 and p1584, referred to as CY12660, expresses the human $A_1$ adenosine receptor. To grow this strain in liquid or on agar plates, minimal media lacking leucine and tryptophan was used. To perform a growth assay on plates (assaying FUS1-HIS3), the plates were at pH 6.8 and contained 0.5-2.5 mM 3-amino-1,2,4-triazole and lacked leucine, tryptophan and histidine. As a control for specificity, a comparison with one or more other yeast-based seven transmembrane receptor screens was included in all experiments.

Construction of Yeast Strains Expressing Human A2a Adenosine Receptor

In this example, the construction of yeast strains expressing a human A2a adenosine receptor functionally integrated into the yeast pheromone system pathway is described.

I. Expression Vector Construction

To construct a yeast expression vector for the human A2a adenosine receptor, the human A2a receptor cDNA was obtained from Dr. Phil Murphy (NIH). Upon receipt of this clone, the A2a receptor insert was sequenced and found to be identical to the published sequence (GenBank accession # S46950). The receptor cDNA was excised from the plasmid by PCR with VENT polymerase and cloned into the plasmid pLPBX, which drives receptor expression by a constitutive Phosphoglycerate Kinase (PGK) promoter in yeast. The sequence of the entire insert was once again sequenced and found to be identical with the published sequence. However, by virtue of the cloning strategy employed there were three amino acids appended to the carboxy-terminus of the receptor, GlySerVal.

II. Yeast Strain Construction

To create a yeast strain expressing the human A2a adenosine receptor, yeast strain CY8342 was used as the starting parental strain. The genotype of CY8342 is as follows: MATa far1D1442 tbt1-1 lys2 ura3 leu2 trp1 his3 fus1-HIS3 can1 ste3D1156 gpaD1163 ste14::trp1::LYS2 gpa1p-rG$_{\alpha s}$E10K (or gpa1p-rG$_{\alpha s}$D229S or gpa1p-rG$_{\alpha s}$E10K+D229S)

The genetic markers are as described in Example 1, except for the G-protein variation. For human A2a receptor-expression, yeast strains were utilized in which the endogenous yeast G protein GPA1 had been deleted and replaced by a mammalian G$_{\alpha s}$. Three rat G$_{\alpha s}$ mutants were utilized. These variants contain one or two point mutations which convert them into proteins which couple efficiently to yeast βγ. They are identified as G$_{\alpha s}$E10K (in which the glutamic acid at position ten is replaced with lysine), G$_{\alpha s}$D229S (in which the aspartic acid at position 229 is replaced with serine) and G$_{\alpha s}$E10K+D229S (which contains both point mutations).

Strain CY8342 (carrying one of the three mutant rat G$_{\alpha S}$ proteins) was transformed with either the parental vector pLPBX (Receptor$^-$) or with pLPBX-A2a (Receptor$^+$). A plasmid with the FUS1 promoter fused to β-galactosidase coding sequences (described in above) was added to assess the magnitude of activation of the pheromone response pathway.

Functional Assay using Yeast Strains Expressing Human A$_1$ Adenosine Receptor

In this example, the development of a functional screening assay in yeast for modulators of the human A$_1$ adenosine receptor is described.

I. Ligands used in Assay

Adenosine, a natural agonist for this receptor, as well as two other synthetic agonists were utilized for development of this assay. Adenosine, reported to have an EC$_{50}$ of approximately 75 nM, and (−)-N6-(2-phenylisopropyl)-adenosine (PIA) with a reported affinity of approximately 50 nM were used in a subset of experiments. 5'-N-ethylcarboxamido-adenosine (NECA) was used in all growth assays. To prevent signaling due to the presence of adenosine in the growth media, adenosine deaminase (4 U/ml) was added to all assays.

II. Biological Response in Yeast

The ability of the A$_1$ adenosine receptor to functionally couple in a heterologous yeast system was assessed by introducing the A$_1$ receptor expression vector (p5095, described above) into a series of yeast strains that expressed different G protein subunits. The majority of these transformants expressed G$_\alpha$ subunits of the G$_{\alpha i}$ or G$_{\alpha o}$ subtype. Additional G$_\alpha$ proteins were also tested for the possible identification of promiscuous receptor-G$_\alpha$ protein coupling. In various strains, a STE18 or a chimeric STE18-Gγ2 construct was integrated into the genome of the yeast. The yeast strains harbored a defective HIS3 gene and an integrated copy of FUS1-HIS3, thereby allowing for selection in selective media containing 3-amino-1,2,4-triazole (tested at 0.2, 0.5 and 1.0 mM) and lacking histidine. Transformants were isolated and monolayers were prepared on media containing 3-amino-1,2,4-triazole, 4 U/ml adenosine deaminase and lacking histidine. Five microliters of various concentrations of ligand (e.g., NECA at 0, 0.1, 1.0 and 10 mM) was applied. Growth was monitored for 2 days. Ligand-dependent growth responses were tested in this manner in the various yeast strains. The results are summarized in Table 5 below. The symbol (−) indicates that ligand dependent receptor activation was not detected while (+) denotes ligand-dependent response. The term "LIRMA" indicates ligand independent receptor mediated activation.

TABLE 5

| Yeast strain | Gα subunit | Gγ subunit | Strain Variants | Result |
| --- | --- | --- | --- | --- |
| CY1316 | GPA$_1$ | STE18 | | − |
| | GPA41-G$_{\alpha i1}$ | | | + |
| | GPA41-G$_{\alpha i2}$ | | | + |
| | GPA41-G$_{\alpha i3}$ | | | + |
| | GPA41-G$_{\alpha i2}$-G$_{\alpha OB}$ | | | LIRMA |
| | GPA41-G$_{\alpha SE10K}$ | | | − |
| | GPA41-G$_{\alpha SD229S}$ | | | − |
| CY7967 | GPA41-G$_{\alpha i3}$-integrated | STE18 | | +++ |
| CY2120 | GPA$_1$ | STE18 | sst2Δ | + |
| | GPA41-G$_{\alpha i1}$ | | | + |
| | GPA41-G$_{\alpha i2}$ | | | + |
| | GPA41-G$_{\alpha i3}$ | | | + |
| | GPA41-G$_{\alpha i2}$-G$_{\alpha OB}$ | | | LIRMA |
| | GPA41-G$_{\alpha SE10K}$ | | | − |
| | GPA41-G$_{\alpha SD229S}$ | | | − |
| CY9438 | GPA$_1$ | STE18-Gγ2 | | − |
| | GPA41-G$_{\alpha i1}$ | | | + |
| | GPA41-G$_{\alpha i2}$ | | | + |
| | GPA41-G$_{\alpha i3}$ | | | + |
| | GPA41-G$_{\alpha i2}$-G$_{\alpha OB}$ | | | LIRMA |
| | GPA41-G$_{\alpha SE10K}$ | | | − |
| | GPA41-G$_{\alpha SD229S}$ | | | − |
| CY10560 | GPA$_1$-integrated | STE18-Gγ2 | sst2Δ | ++ |

As indicated in Table 5, the most robust signaling was found to occur in a yeast strain expressing the GPA$_1$(41)-G$_{\alpha i3}$ chimera.

III. Fus1-LacZ Assay

To characterize activation of the pheromone response pathway more fully, synthesis of β-galactosidase through fus1LacZ in response to agonist stimulation was measured. To perform the β-galactosidase assay, increasing concentrations of ligand were added to mid-log culture of human A$_1$ adenosine receptor expressed in a yeast strain co-expressing a Ste18-Gγ2 chimera and GPA$_{41}$-G$_{\alpha i3}$. Transformants were isolated and grown overnight in the presence of histidine and 4 U/ml adenosine deaminase. After five hours of incubation with 4 U/ml adenosine deaminase and ligand, induction of β-galactosidase was measured using CPRG as the substrate for β-galactoside. 5×10$^5$ cells were used per assay.

The results obtained with NECA stimulation indicated that-at a NECA concentration of 10$^{-8}$ M approximately 2-fold stimulation of β-galactosidase activity was achieved. Moreover, a stimulation index of approximately 10-fold was observed at a NECA concentration of 10$^{-5}$ M.

The utility of this assay was extended by validation of the activity of antagonists on this strain. Two known adenosine antagonist, XAC and DPCPX, were tested for their ability to compete against NECA (at 5 mM) for activity in the β-galactosidase assay. In these assays, β-galactosidase induction was measured using FDG as the substrate and 1.6×10$^5$ cells per assay. The results indicated that both XAC and DPCPX served as potent antagonists of yeast-expressed $A_1$ adenosine receptor, with $IC_{50}$ values of 44 nM and 49 nM, respectively.

In order to determine if this inhibitory effect was specific to the $A_1$ subtype, a series of complementary experiments were performed with the yeast-based $A_{2a}$ receptor assay (described in Example 4). Results obtained with the $A_{2a}$ yeast-based assay indicated that XAC was a relatively effective $A_{2a}$ receptor antagonist, consistent with published reports. In contrast, DPCPX was relatively inert at this receptor, as expected from published reports.

IV. Radioligand Binding

The $A_1$ adenosine receptor assay was further characterized by measurement of the receptor's radioligand binding parameters. Displacement binding of [$^3$H]CPX by several adenosine receptor reference compounds, XAC, DPCPX, and CGS, was analyzed using membranes prepared from yeast expressing the human $A_1$ adenosine receptor. The results with yeast membranes expressing the human $A_1$ adenosine receptor were compared to those from yeast membranes expressing the human A2a adenosine receptor or the human A3 receptor to examine the specificity of binding. To perform the assay, fifty mg of membranes were incubated with 0.4 nM [$^3$H]CPX and increasing concentrations of adenosine receptor ligands. Incubation was in 50 mM Tris-HCl, pH 7.4, 1 mM EDTA, 10 mM $MgCl_2$, 0.25% BSA and 2 U/ml adenosine deaminase in the presence of protease inhibitors for 60 minutes at room temperature. Binding was terminated by addition of ice-cold 50 mM Tris-HCl, pH 7.4 plus 10 mM $MgCl_2$, followed by rapid filtration over GF/B filters previously soaked with 0.5% polyethyenimine, using a Packard 96-well harvester. Data were analyzed by nonlinear least square curve fitting procedure using Prism 2.01 software. The $IC_{50}$ values obtained in this experiment are summarized in Table 6, below:

TABLE 6

| Compound | hA1R | $IC_{50}$ [nM] hA2aR | hA3R |
|---|---|---|---|
| XAC | 6.6 | 11.7 | 53.1 |
| DPCPX | 8.5 | 326.4 | 1307.0 |
| CGS-15943 | 13.1 | 15.8 | 55.5 |
| NECA | 215.5 | 294.9 | 34.9 |
| R-PIA | 67.6 | 678.1 | 23.6 |
| IB-MECA | 727.7 | 859.4 | 3.1 |
| Alloxozine | 1072.0 | 1934.0 | 8216.0 |

These data indicate that the reference compounds have affinities consistent with those reported in the literature.

The data further indicate that the yeast-based assays are of sufficient sensitivity to discriminate receptor subtype specificity.

Functional Assay using Yeast Strains Expressing Human A2a Adenosine Receptor

In this example, the development of a functional screening assay in yeast for modulators of the human $A_1$ adenosine receptor is described.

I. Ligands used in Assay

The natural ligand adenosine, as well as other thoroughly characterized and commercially available ligands were used for study of the human A2a receptor functionally expressed in yeast. Three ligands have been used in the establishment of this assay. They include:

| Ligand | Reported $K_i$ | Function |
|---|---|---|
| Adenosine | 500 nM | agonist |
| 5'-N-ethylcarboxamidoadenosine (NECA) | 10-15 nM | agonist |
| (−)-N6-(2-phenylisopropyl)-adenosine (PIA) | 100-125 nM | agonist |

To prevent signaling due to the presence of adenosine in the growth media, adenosine deaminase (4 U/ml) was added to all assays.

II. Biological Response in Yeast

A2a receptor agonists were tested for the capacity to stimulate the pheromone response pathway in yeast transformed with the $A_{2a}$ receptor expression plasmid and expressing either $G_{\alpha s}$E10K, $G_{\alpha s}$D229S or $G_{\alpha s}$E10K+D229S. The ability of ligand to stimulate the pheromone response pathway in a receptor dependent manner was indicated by an alteration in the yeast phenotype. Receptor activation modified the phenotype from histidine auxotrophy to histidine prototrophy (activation of fus1-HIS3). Three independent transformants were isolated and grown overnight in the presence of histidine. Cells were washed to remove histidine and diluted to $2\times10^6$ cells/ml. 5 µl of each transformant was spotted onto nonselective media (including histidine) or selective media (1 mM AT) in the absence or presence of 4 U/ml adenosine deaminase. Plates were grown at 30° C. for 24 hours. In the presence of histidine both Receptor$^+$ (R$^+$) and Receptor$^-$ (R$^-$) strains were capable of growth. However, in the absence of histidine only R$^+$ cells grew. Since no ligand had been added to these plates two explanations were possible for this result. One possible interpretation was that the receptor bearing yeast were at a growth advantage due to Ligand Independent Receptor Mediated Activation (LIRMA). Alternatively the yeast could have been synthesizing the ligand adenosine. To distinguish between these two possibilities, an enzyme which degrades the ligand, adenosine deaminase (ADA), was added to the growing yeast and plates. In the presence of adenosine deaminase R$^+$ cells no longer grew in the absence of histidine, indicating that the yeast were indeed synthesizing ligand.

This interpretation was confirmed by an A2a growth assay in liquid. In this experiment R$^+$ yeast (a $G_{\alpha s}$E10K strain expressing the A2a receptor) were inoculated at three densities ($1\times10^6$ cell/ml; $3\times10^5$ cells/ml; or $1\times10^5$ cells/ml) in the presence or absence of adenosine deaminase (4 U/ml). The stringency of the assay was enhanced with increasing concentrations (0, 0.1, 0.2 or 0.4 mM) of 3-amino-1,2,4-triazole (AT), a competitive antagonist of imidazoleglycerol-P dehydratase, the protein product of the HIS3 gene. In the presence of adenosine deaminase and 3-amino-1,2,4-triazole yeast grew less vigorously. However in the absence of 3-amino-1,2,4-triazole, adenosine deaminase had little effect. Thus adenosine deaminase itself had no direct effect upon the pheromone response pathway.

An alternative approach to measuring growth and one that can be miniaturized for high throughput screening is an A2a receptor ligand spot assay. A $G_{\alpha s}$E10K strain expressing the A2a receptor (A2aR+) or lacking the receptor (R−) was grown overnight in the presence of histidine and 4 U/ml adenosine deaminase. Cells were washed to remove histidine and diluted to $5\times10^5$ cells/ml. $1\times10^6$ cells were spread onto selective plates containing 4 U/ml adenosine deaminase and 0.5 or 1.0 mM 3-amino-1,2,4-triazole (AT) and allowed to dry for 1 hour. 5 µl of the following reagents were applied to the monolayer: 10 mM adenosine, 38.7 mM histidine, dimethylsulfoxide (DMSO), 10 mM PIA or 10 mM NECA. Cells were grown 24 hours at 30° C. The results showed that cells without receptor could only grow when histidine was added to the media. In contrast, R+ cells only grew in areas where the A2a receptor ligands PIA and NECA had been spotted. Since the plates contained adenosine deaminase, the lack of growth where adenosine had been spotted confirmed that adenosine deaminase was active.

III. Fus1 LacZ Assay

To quantitate activation of the yeast mating pathway, synthesis of β-galactosidase through fus1LacZ was measured. Yeast strains expressing $G_{\alpha s}E10K$, $G_{\alpha s}D229S$ or $G_{\alpha s}E10K+D229S$ were transformed with a plasmid encoding the human A2a receptor (R+) or with a plasmid lacking the receptor (R−). Transformants were isolated and grown overnight in the presence of histidine and 4 U/ml adenosine deaminase. $1\times10^7$ cells were diluted to $1\times10^6$ cells/ml and exposed to increasing concentrations of NECA for 4 hours, followed by determination of the β-galactosidase activity in the cells.

The results demonstrated that essentially no β-galactosidase activity was detected in R− strains, whereas increasing amounts of β-galactosidase activity were detected in R+strains expressing either $G_{\alpha s}E10K$, $G_{\alpha s}D229S$ or $G_{\alpha s}E10K+D229S$ as the concentration of NECA increased, indicating a dose dependent increase in units of β-galactosidase detected in response to exposure to increased ligand concentration. This dose dependency was only observed in cells expressing the A2a receptor. Furthermore the most potent $G_{\alpha s}$ construct for the A2a receptor was $G_{\alpha s}E10K$. The $G_{\alpha s}D229S$ construct was the second-most potent $G_{\alpha s}$ construct for the A2a receptor, while the $G_{\alpha s}E10K+D229S$ construct was the least potent of the three $G_{\alpha s}$ constructs tested, although even the $G_{\alpha s}E10K+D229S$ construct stimulated readily detectable amounts of β-galactosidase activity.

For a further description of the assays identified, see U.S. application Ser. No. 09/088,985, entitled "Functional Expression of Adenosine Receptors in Yeast", filed Jun. 2, 1998, the entire contents of which are hereby incorporated herein by reference.

Pharmacological Characterization of the Human Adenosine Receptor Subtypes

Material and Methods

Materials. [$^3$H]-DPCPX [Cyclopentyl-1,3-dipropylxantine, 8-[dipropyl-2,3-$^3$H(N)] (120.0 Ci/mmol); [$^3$H]-CGS 21680, [carboxyethyl-$^3$H (N)] (30 Ci/mmol) and [$^{125}$I]-AB-MECA ([$^{125}$I]-4-Aminobenzyl-5'-N-Methylcarboxamideoadenosine) (2,200 Ci/mmol) were purchased from New England Nuclear (Boston, Mass.). XAC (Xantine amine congener); NECA (5'-N-Ethylcarboxamidoadenosine); and IB-MECA from Research Biochemicals International (RBI, Natick, Mass.). The Adenosine Deaminase and Complete protease inhibitor cocktail tablets were purchased from Boehringer Mannheim Corp. (Indianapolis, Ind.). Membranes from HEK-293 cells stably expressing the human Adenosine 2a [RB-HA$_2$a]; Adenosine 2b [RB-HA$_2$b] or Adenosine 3 [RB-HA3] receptor subtypes, respectively were purchased from Receptor Biology (Beltsville, Md.). Cell culture reagents were from Life Technologies (Grand Island, N.Y.) except for serum that was from Hyclone (Logan, Utah).

Yeast strains: *Saccharomyces cerevisiae* strains CY12660 [far1*1442 tbt1-1 fus1-HIS3 can1 ste14::trp1::LYS2 ste3*1156 gpa1(41)-Gαi3 lys2 ura3 leu2 trp1: his3; LEU2 PGKp-MfαlLeader-hA1R-PHO5term 2mu-orig REP3 Ampr] and CY8362 [gpa1p-rGαsE10K far1*1442 tbt1-1 fus1-HIS3 can1 ste14::trp1: LYS2 ste3*1156 lys2 ura3 leu2 trp1 his3; LEU2 PGKp-hA2aR 2mu-ori REP3 Ampr] were developed as described above.

Yeast culture: Transformed yeast were grown in Leu-Trp [LT] media (pH 5.4) supplemented with 2% glucose. For the preparation of membranes 250 ml of LT medium were inoculated with start titer of $1-2\times10^6$ cells/ml from a 30 ml overnight culture and incubated at 30° C. under permanent oxygenation by rotation. After 16 h growth the cells were harvested by centrifugation and membranes were prepared as described below.

Mammalian Tissue Culture: The HEK-293 cells stably expressed human Adenosine 2a receptor subtype (Cadus clone #5) were grown in Dulbeco's minimal essential media (DMEM) supplemented with 10% fetal bovine serum and 1× penicillin/streptomycin under selective pressure using 500 mg/ml G418 antibiotic, at 37° C. in a humidified 5% $CO_2$ atmosphere.

Yeast Cell Membrane Preparations: 250 ml cultures were harvested after overnight incubation by centrifugation at 2,000×g in a Sorvall RT6000 centrifuge. Cells were washed in ice-cold water, centrifuged at 4° C. and the pellet was resuspended in 10 ml ice-cold lysis buffer [5 mM Tris-HCl, pH 7.5; 5 mM EDTA; and 5 mM EGTA] supplemented with Protease inhibitor cocktail tablets (1 tablet per 25 ml buffer). Glass beads (17 g; Mesh 400-600; Sigma) were added to the suspension and the cells were broken by vigorous vortexing at 4° C. for 5 min. The homogenate was diluted with additional 30 ml lysis buffer plus protease inhibitors and centrifuged at 3,000×g for 5 min. Subsequently the membranes were peleted at 36,000×g (Sorvall RC5B, type SS34 rotor) for 45 min. The resulting membrane pellet was resuspended in 5 ml membrane buffer [50 mM Tris-HCl, pH 7.5; 0.6 mM EDTA; and 5 mM $MgCl_2$] supplemented with Protease inhibitor cocktail tablets (1 tablet per 50 ml buffer) and stored at −80° C. for further experiments.

Mammalian Cell Membrane Preparations: HEK-293 cell membranes were prepared as described previously (Duzic E et al.: *J. Biol. Chem.*, 267, 9844-9851, 1992) Briefly, cells were washed with PBS and harvested with a rubber policeman. Cells were pelted at 4° C. 200×g in a Sorvall RT6000 centrifuge. The pellet was resuspended in 5 ml/dish of lysis buffer at 4° C. (5 mM Tris-HCl, pH 7.5; 5 mM EDTA; 5 mM EGTA; 0.1 mM Phenylmethylsulfonyl fluoride, 10 mg/ml pepstatin A; and 10 mg/ml aprotinin) and homogenized in a Dounce homogenizer. The cell lysate was then centrifuged at 36,000×g (Sorvall RC5B, type SS34 rotor) for 45 min and the pellet resuspended in 5 ml membrane buffer [50 mM Tris-HCl, pH 7.5; 0.6 mM EDTA; 5 mM $MgCl_2$; 0.1 mM Phenylmethylsulfonyl fluoride, 10 mg/ml pepstatin A; and 10 mg/ml aprotinin) and stored at −80° C. for further experiments.

The Bio-Rad protein assay kits, based on the Bradford dye-binding procedure, (Bradford, M.: *Anal. Biochem.* 72:248 (1976)) were used to determine total protein concentration in yeast and mammalian membranes.

Adenosine 1 receptor subtype saturation and competition radioligand binding: Saturation and competition binding on membranes from yeast cell transformed with human $A_1$ receptor subtype were carried out using antagonist [$^3$H] DPCPX as a radioactive ligand. Membranes was diluted in binding buffer [50 mM Tris-HCl, pH 7.4; containing 10 mM MgCl$_2$; 1.0 mM EDTA; 0.25% BSA; 2 U/ml adenosine deaminase and 1 protease inhibitor cocktail tablet/50 ml] at concentrations of 1.0 mg/ml.

In saturation binding membranes (50 µg/well) were incubate with increasing concentrations of [$^3$H] DPCPX (0.05-25 nM) in a final volume of 100 µl of binding buffer at 25° C. for 1 hr in the absence and presence of 10 µM unlabeled XAC in a 96-well microtiter plate.

In competition binding membranes (50 µg/well) were incubate with [$^3$H] DPCPX (1.0 nM) in a final volume of 100 ml of binding buffer at 25° C. for 1 hr in the absence and presence of 10 µM unlabeled XAC or increasing concentrations of competing compounds in a 96-well microtiter plate.

Adenosine 2a receptor subtype competition radioligand binding: Competition binding on membranes from HEK293 cell stably expressing the human A2a receptor subtype were carried out using agonist [$^3$H] CGS-21680 as a radioactive ligand. Membranes was diluted in binding buffer [50 mM Tris-HCl, pH 7.4; containing 10 mM MgCl$_2$; 1.0 mM EDTA; 0.25% BSA; 2 U/ml adenosine deaminase and 1 protease inhibitor cocktail tablet/50 ml] at concentrations of 0.2 mg/ml. Membranes (10 µg/well) were incubate with [$^3$H] CGS-21680 (100 nM) in a final volume of 100 ml of binding buffer at 25° C. for 1 hr in the absence and presence of 50 µM unlabeled NECA or increasing concentrations of competing compounds in a 96-well microtiter plate.

Adenosine 3 receptor competition radioligand binding: Competition binding on membranes from HEK293 cell stably expressing the human A3 receptor subtype were carried out using agonist [$^{125}$I] AB-MECA as a radioactive ligand. Membranes was diluted in binding buffer [50 mM Tris-HCl, pH 7.4; containing 10 mM MgCl$_2$; 1.0 mM EDTA; 0.25% BSA; 2 U/ml adenosine deaminase and 1 protease inhibitor cocktail tablet/50 ml] at concentrations of 0.2 mg/ml. Membranes (10 µg/well) were incubate with [$^{125}$I] AB-MECA (0.75 nM) in a final volume of 100 µl of binding buffer at 25° C. for 1 hr in the absence and presence of 10 µM unlabeled IB-MECA or increasing concentrations of competing compounds in a 96-well microtiter plate.

At the end of the incubation, the A$_1$, A$_{2a}$ and A$_3$ receptor subtypes radioligand binding assays was terminated by the addition of ice-cold 50 mM Tris-HCl (pH 7.4) buffer supplemented with 10 mM MgCl$_2$, followed by rapid filtration over glass fiber filters (96-well GF/B UniFilters, Packard) previously presoaked in 0.5% polyethylenimine in a Filtermate 196 cell harvester (Packard). The filter plates were dried coated with 50 µl/well scintillation fluid (MicroScint-20, Packard) and counted in a TopCount (Packard). Assays were performed in triplicate. Non-specific binding was 5.6±0.5%, 10.8±1.4% and 15.1±2.6% of the total binding in a A1R, A2aR and A3R binding assay, respectively.

Adenosine 2b receptor subtype competition radioligand binding: Competition binding on membranes from HEK293 cell stably expressing the human A2b receptor subtype were carried out using A$_1$ receptor antagonist [$^3$H] DPCPX as a radioactive ligand. Membranes was diluted in binding buffer [10 mM Hepes-KOH, pH 7.4; containing 1.0 mM EDTA; 0.1 mM Benzamidine and 2 U/ml adenosine deaminase] at concentrations of 0.3 mg/ml. Membranes (15 µg/well) were incubate with [$^3$H] DPCPX (15 nM) in a final volume of 100 µl of binding buffer at 25° C. for 1 hr in the absence and presence of 10 µM unlabeled XAC or increasing concentrations of competing compounds in a 96-well microtiter plate. At the end of the incubation, the assay was terminated by the addition of ice-cold 10 mM Hepes-KOH (pH 7.4) buffer followed by rapid filtration over glass fiber filters (96-well GF/C UniFilters, Packard) previously presoaked in 0.5% polyethylenimine in a Filtermate 196 cell harvester (Packard). The filter plates were dried coated with 50 µl/well scintillation fluid (MicroScint-20, Packard) and counted in a TopCount (Packard). Assays were performed in triplicate. Non-specific binding was 14.3±2.3% of the total binding.

Specific binding of [$^3$H] DPCPX; [$^3$H] CGS-21680 and [$^{125}$I] AB-MECA was defined as the difference between the total binding and non-specific binding. Percent inhibition of the compounds was calculated against total binding. Competition data were analyzed by iterative curve fitting to a one site model, and K$_I$ values were calculated from IC$_{50}$ values (Cheng and Prusof, Biochem. Pharmacol. 22, 3099-3109, 1973) using the GraphPad Prizm 2.01 software.

Results

A primary function of certain cell surface receptors is to recognize appropriate ligands. Accordingly, we determined ligand binding affinities to establish the functional integrity of the Adenosine 1 receptor subtype expressed in yeast. Crude membranes prepared from *Saccharomyces cerevisiae* transformed with human Adenosine 1 receptor subtype construct exhibited specific saturable binding of [$^3$H] DPCPX with a K$_D$ of 4.0±0.19 nM. The K$_D$ and B$_{max}$ value were calculated from the saturation isotherm and Scatchard transformation of the data indicated a single class of binding sites. The densities of adenosine binding sites in the yeast membrane preparations were estimated to 716.8±43.4 fmol/mg membrane protein.

The pharmacological subtype characteristics of the recombinant yeast cells transformed with human A$_1$ receptor subtype were investigated with subtype selective adenosine ligands (XAC, DPCPX; CGS-15943; Compound 600; Compound 1002; NECA, (R)-PIA; IB-MECA and Alloxazine) that competed with [$^3$H] DPCPX in the expected rank order. Displacement curves recorded with these compounds show the typical steepness with all the ligands, and the data for each of the ligands could be modeled by a one-site fit. The apparent dissociation constants estimated for the individual compound from the curves (Table 7) are consistent with value published for the receptor obtained from other sources.

TABLE 7

Ki values for membranes from yeast cells transformed with human A$_1$ receptor subtype

| Ligands | K$_I$ (nM) |
| --- | --- |
| XAC | 5.5 |
| DPCPX | 7.1 |
| CGS-1594 | 10.8 |
| NECA | 179.6 |
| (R)-PIA | 56.3 |
| IB-MECA | 606.5 |
| Alloxazine | 894.1 |

TABLE 8

Profile of Selective Adenosine Antagonists

[Structure: 4-(R-NH)-2-phenyl-5,6-dimethyl-7H-pyrrolo[2,3-d]pyrimidine]

| Compound | R | Binding Ki (nM) | | | |
|---|---|---|---|---|---|
| | | A1 | A2a | A2b | A3 |
| 1300 | –CH₂CH₂NHAc | 9.8-25.1 | 18.0-48.6 | 80.3 | 513.0 |
| 1301 | –CH(Me)CH₂NHAc | 27.8 | 50.7 | 84.6 | 429.8 |
| 1302 | –CH₂CH₂NHC(O)NHMe | 20.2 | 75.6 | 20.1 | 4.3 |
| 1303 | –CH₂CH₂C(O)NHMe | 17.4 | 111.3 | 120.6 | 44.6 |
| 1304 | trans-4-hydroxycyclohexyl | 13.9-30.9 | 933.7 | 138.0 | 21.5 |
| 1305[1] | trans-4-hydroxycyclohexyl | 46.6 | 730.9 | 30% | 9.9 |
| 1306[2] | cis-4-hydroxycyclohexyl | 16.4 | 766.3 | 168.3 | 71.7 |
| 1307 | cis-3-hydroxycyclopentyl (dl) | 29.1 | 190.6 | 1143.0 | 3.1 |
| 1308 | trans-3-hydroxycyclopentyl (±) | 180 | 230 | 670 | 1.0 |

TABLE 8-continued

Profile of Selective Adenosine Antagonists

[Structure: 4-(NHR)-2-phenyl-5,6-dimethyl-7H-pyrrolo[2,3-d]pyrimidine]

| Compound | R | Binding Ki (nM) | | | |
|---|---|---|---|---|---|
| | | A1 | A2a | A2b | A3 |
| 1309 | 3-(N-acetylamino)piperidin-1-yl | 40 | 109 | 109 | 0.3 |
| 1310 | -(CH$_2$)$_3$-NH-C(O)-NHMe | 255 | 76% | 275 | ≦2.6 |
| 1311 | -(CH$_2$)$_4$-NH-C(O)-Me | 531 | 981 | 736 | 5.3 |
| 1312 | -(CH$_2$)$_4$-NH-C(O)-NHMe | 443 | 2965 | 375 | ≦6.2 |
| 1313[3] | -(CH$_2$)$_2$-NH-C(O)-C(NH$_3^-$)(cyclopropyl) | 30% | 65% | 515 | 24 |
| 1314 | -(CH$_2$)$_2$-NH-C(O)-NHEt | 87 | 204 | 30 | 0.02 |
| 1315 | -(CH$_2$)$_3$-NH-C(O)-CH$_2$CH$_2$-NH$_3^-$ | 75,000 | 720,000 | 3,400 | 507 |
| 1316 | -(CH$_2$)$_3$-NH-C(O)-CH$_2$-NH$_3^-$ | 333 | 710,000 | 710,000 | 97 |

TABLE 8-continued
Profile of Selective Adenosine Antagonists
| Compound | R | Binding Ki (nM) | | | |
|---|---|---|---|---|---|
| | | A1 | A2a | A2b | A3 |
| 1317 |  | 710.000 | 710.000 | 720.000 | 369 |
| 1318[4] | 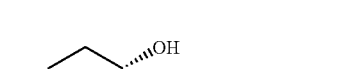 | 3.7 ± 0.5 | 630 ± 56.4 | 2307 ± 926 | 630 ± 76 |
| 1319[4,5] |  | 1.8 | 206 | 802 | 270 |
| 1320[4,6] |  | 8.0 | 531 | 530 | 419 |
| 1321[4,7] |  | 8.0 | 131 | 1031 | 54%[8] |
[1] 2-thienyl-2-yl;
[2] $C_5$—H;
[3] water soluble;
[4] $R_5$ and $R_6$ are hydrogen;
[5] $R_3$ is 3-fluorophenyl;
[6] $R_3$ is 3-chlorophenyl;
[7] $R_3$ is 4-pyridyl;
[8] % activity @ 10 μM

TABLE 9

Adenosine A3 Receptor Selective Compounds

| Compound | Structure | Ki-A1 | Ki-A2a | Ki-A2b | Ki-A3 |
|---|---|---|---|---|---|
| 1202 | 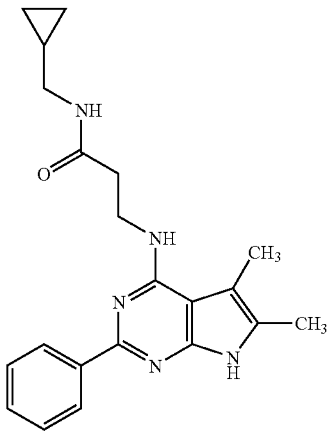 | | | | * |
| 1700 | 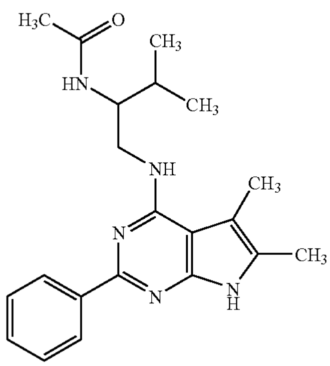 | | | | * |
| 1309 | 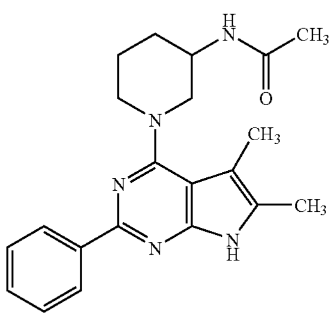 | | | | * |
| 1701 | 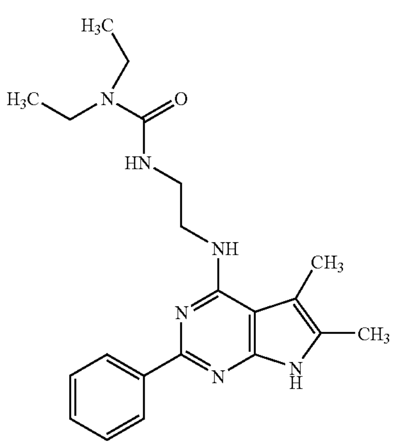 | | | | * |

TABLE 9-continued

Adenosine A₃ Receptor Selective Compounds

| Compound | Structure | Ki-A1 | Ki-A2a | Ki-A2b | Ki-A3 |
|---|---|---|---|---|---|
| 1311 | 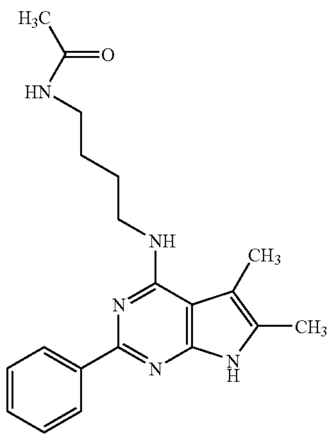 | | | | * |
| 1312 | 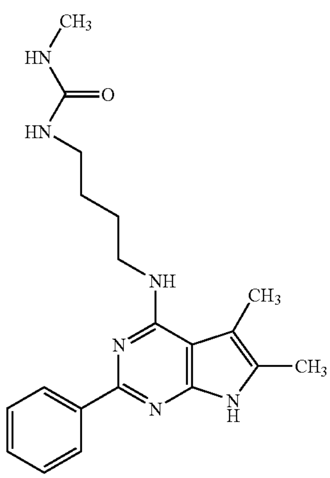 | | | | * |
| 1310 | 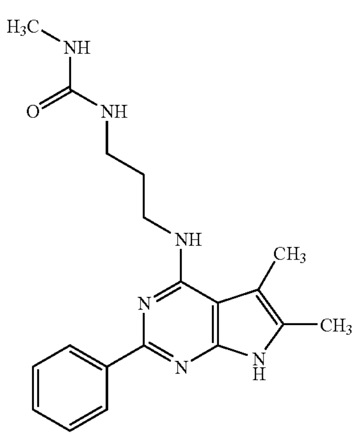 | | | | * |

TABLE 9-continued
Adenosine A₃ Receptor Selective Compounds
| Compound | Structure | Ki-A1 | Ki-A2a | Ki-A2b | Ki-A3 |
|----------|-----------|-------|--------|--------|-------|
| 1316 | 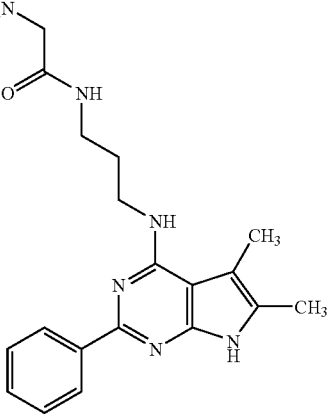 | | | | * |
| 1702 | 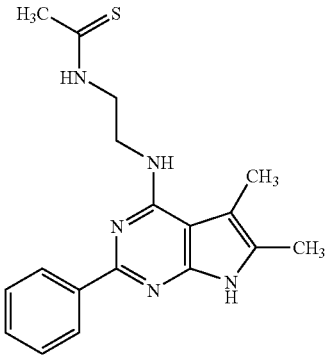 | | | | * |
| 1703 | 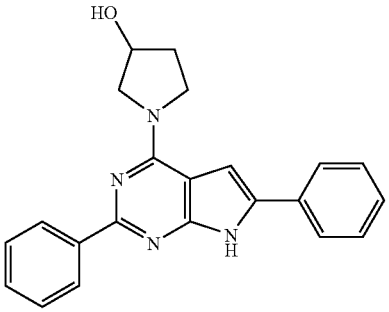 | | | | * |

TABLE 9-continued
Adenosine A₃ Receptor Selective Compounds
| Compound | Structure | Ki-A1 | Ki-A2a | Ki-A2b | Ki-A3 |
|---|---|---|---|---|---|
| 1704 | 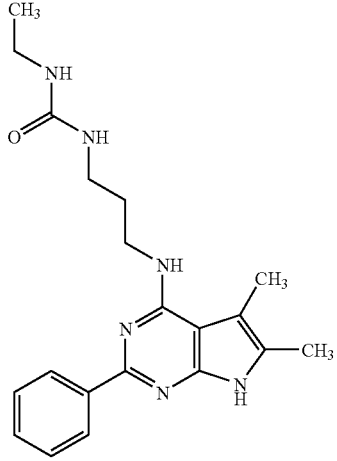 | | | | * |
| 1705 | 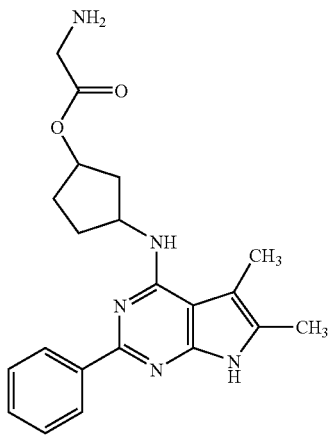 | | | | * |
| 1706 | 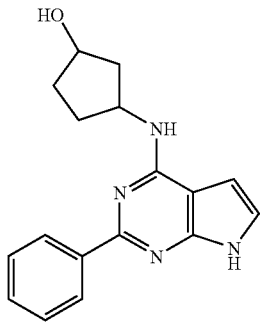 | | | | * |

TABLE 9-continued

Adenosine A₃ Receptor Selective Compounds

| Compound | Structure | Ki-A1 | Ki-A2a | Ki-A2b | Ki-A3 |
|---|---|---|---|---|---|
| 1707 | 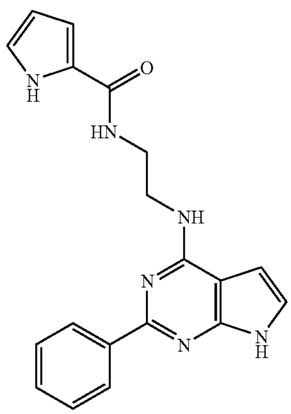 | | | | * |
| 1708 | 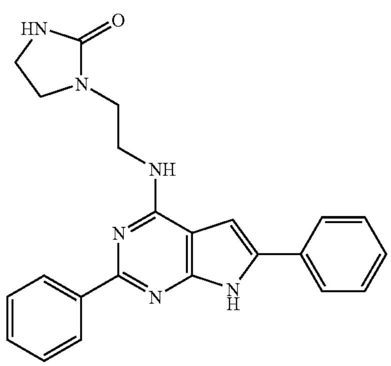 | | | | * |
| 1709 | 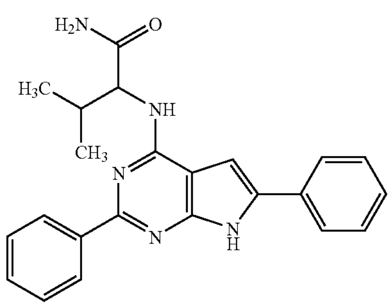 | | | | * |
| 1710 | 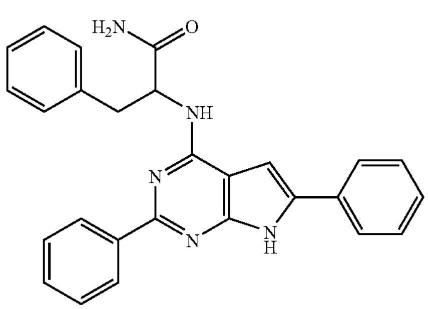 | | | | * |

TABLE 9-continued

Adenosine A₃ Receptor Selective Compounds

| Compound | Structure | Ki-A1 | Ki-A2a | Ki-A2b | Ki-A3 |
|----------|-----------|-------|--------|--------|-------|
| 1711 | 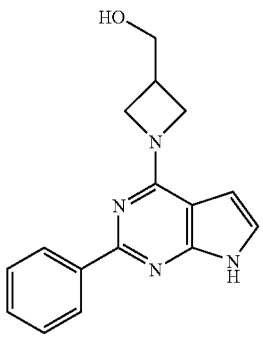 | | | | * |
| 1712 | 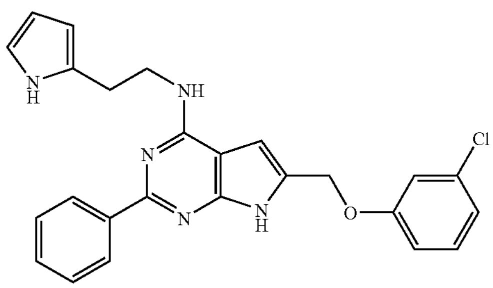 | | | | * |
| 1713 | 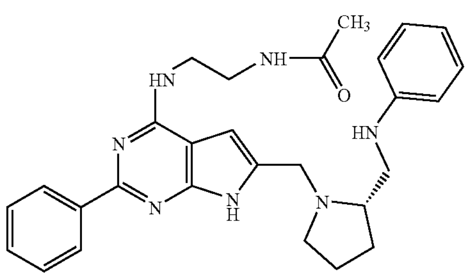 | | | | * |
| 1714 | 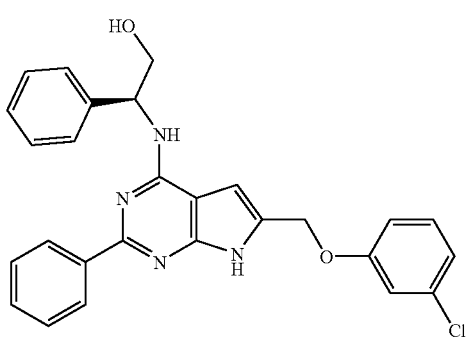 | | | | * |

TABLE 9-continued

Adenosine A₃ Receptor Selective Compounds

| Compound | Structure | Ki-A1 | Ki-A2a | Ki-A2b | Ki-A3 |
|---|---|---|---|---|---|
| 1715 | | | | | * |
| 1716 | | | | | * |
| 1717 | | | | | * |
| 1718 | | | | | * |

TABLE 9-continued

Adenosine A₃ Receptor Selective Compounds

| Compound | Structure | Ki-A1 | Ki-A2a | Ki-A2b | Ki-A3 |
|---|---|---|---|---|---|
| 1719 | 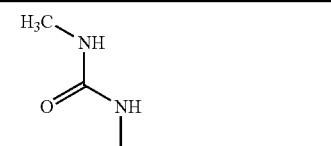 | | | | * |

\* at least 10 times more selective than other three subtypes.

INCORPORATION BY REFERENCE

All patents, published patent applications and other references disclosed herein are hereby expressly incorporated herein by reference.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A compound having the structure:

wherein
m is 0, 1, 2, or 3;
$R_2$ is a substituted or unsubstituted imidazole or pyrazole wherein the point of attachment of $R_2$ to the alkyl chain is not N;
$R_5$ is a hydrogen atom or a substituted or unsubstituted alkyl, aryl, or alkylaryl moiety; and
$R_7$ is a halogen atom, $C_1$-$C_4$ alkyl, OH, O-alkyl ($C_1$-$C_4$), $NH_2$, or NH-alkyl ($C_1$-$C_4$)
wherein the substituent, if present, is halogen, hydroxyl, alkoxy, alkylcarbonyloxy, arylcarbonyloxy, alkoxycarbonyloxy, aryloxycarbonyloxy, alkylcarbonyl, alkoxycarbonyl, aminocarbonyl, alkylthiocarbonyl, alkoxyl, cyano, amino, alkyl amino, dialkylamino, arylamino, diarylamino, alkylarylamino, acylamino, alkylcarbonylamino, arylcarbonylamino, ureido, amidino, imino, sulfhydryl, alkylthio, arylthio, sulfamoyl, nitro, trifluoromethyl, cyano, azido, heterocyclyl, alkylaryl, or an aromatic or heteroaromatic moiety, or
a pharmaceutically acceptable salt thereof.

2. The compound of claim 1, wherein $R_7$ is chlorine.

3. The compound of claim 1, having the structure:

or a pharmaceutically acceptable salt thereof.

4. The compound of claim 1, having the structure:

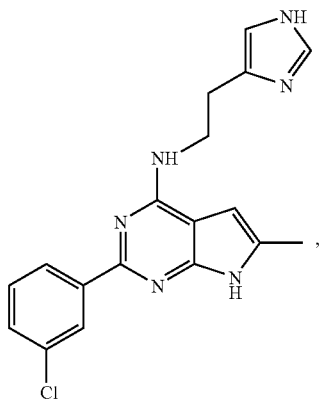

or a pharmaceutically acceptable salt thereof.

5. A compound having the structure:

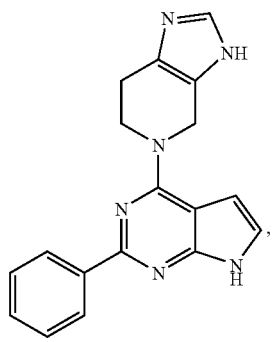

or a pharmaceutically acceptable salt thereof.

6. The compound of claim 1, having the structure:

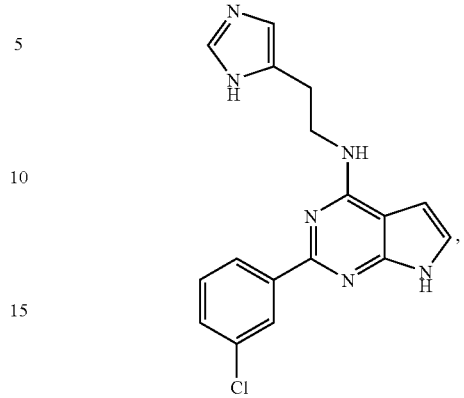

or a pharmaceutically acceptable salt thereof.

7. A pharmaceutical composition comprising the compound of claim 1 or 3 and a pharmaceutically acceptable carrier.

8. A process of making a composition which comprises the compound of claim 1 or 3, comprising admixing the compound with a suitable carrier.

9. The pharmaceutically acceptable salt of claim 1 or 3.

10. The pharmaceutically acceptable salt of claim 9, wherein the pharmaceutically acceptable salt contains an anion selected from the group consisting of maleic, fumaric, tartaric, acetate, phosphate and mesylate.

11. The pharmaceutical composition of claim 7, wherein the pharmaceutical composition is a periocular, retrobulbar or intraocular injection formulation.

12. The pharmaceutically acceptable salt of the compound of claim 2.

* * * * *